US010285992B2

(12) United States Patent
Wennogle et al.

(10) Patent No.: US 10,285,992 B2
(45) Date of Patent: May 14, 2019

(54) COMBINATIONS OF PDE1 INHIBITORS AND NEP INHIBITORS AND ASSOCIATED METHODS

(71) Applicant: Intra-Cellular Therapies, Inc., New York, NY (US)

(72) Inventors: Lawrence P. Wennogle, Hillsborough, NJ (US); Peng Li, New Milford, NJ (US)

(73) Assignee: INTRA-CELLULAR THERAPIES, INC., New York, NY (US)

( * ) Notice: Subject to any disclaimer, the term of this patent is extended or adjusted under 35 U.S.C. 154(b) by 0 days.

(21) Appl. No.: 14/820,323

(22) Filed: Aug. 6, 2015

(65) Prior Publication Data
US 2016/0038494 A1 Feb. 11, 2016

Related U.S. Application Data

(60) Provisional application No. 62/034,665, filed on Aug. 7, 2014.

(51) Int. Cl.
*A61K 31/519* (2006.01)
*A61K 31/197* (2006.01)
*A61K 31/216* (2006.01)
*A61K 45/06* (2006.01)
*A61K 31/198* (2006.01)
*A61K 31/341* (2006.01)

(52) U.S. Cl.
CPC .......... *A61K 31/519* (2013.01); *A61K 31/197* (2013.01); *A61K 31/198* (2013.01); *A61K 31/216* (2013.01); *A61K 31/341* (2013.01); *A61K 45/06* (2013.01)

(58) Field of Classification Search
CPC .... A61K 31/519; A61K 45/06; A61K 31/198; A61K 31/341; A61K 31/216; A61K 31/197
See application file for complete search history.

(56) References Cited

U.S. PATENT DOCUMENTS

| | | | |
|---|---|---|---|
| 5,202,328 A | 4/1993 | de Laszlo et al. |
| 5,294,612 A | 3/1994 | Bacon et al. |
| 5,393,755 A | 2/1995 | Neustadt et al. |
| 5,824,683 A | 10/1998 | McKittrick et al. |
| 5,849,770 A | 12/1998 | Head et al. |
| 5,939,419 A | 8/1999 | Tulshian et al. |
| 5,962,492 A | 10/1999 | Warrellow et al. |
| 6,013,621 A | 1/2000 | Nishi et al. |
| 6,133,273 A | 10/2000 | Gilbert et al. |
| 6,235,742 B1 | 5/2001 | Bell et al. |
| 6,235,746 B1 | 5/2001 | Davis et al. |
| 6,316,444 B1 | 11/2001 | Hunt et al. |
| 6,423,716 B1 | 7/2002 | Matsuno et al. |
| 6,492,371 B2 | 12/2002 | Roylance |
| 6,498,165 B1 | 12/2002 | Armstrong et al. |
| 6,552,029 B1 | 4/2003 | Davis et al. |
| 6,586,423 B2 | 7/2003 | Bilodeau et al. |
| 6,599,908 B1 | 7/2003 | Davis et al. |
| 6,649,608 B2 | 11/2003 | Pease et al. |
| 6,670,368 B1 | 12/2003 | Breault et al. |
| 6,693,099 B2 | 2/2004 | Degenhardt et al. |
| 6,756,373 B1 | 6/2004 | Allerton et al. |
| 6,969,719 B2 | 11/2005 | Asberom et al. |
| 7,153,824 B2 | 12/2006 | Palmer et al. |
| 7,157,451 B2 | 1/2007 | Atwal et al. |
| 8,273,750 B2 | 9/2012 | Li et al. |
| 8,273,751 B2 | 9/2012 | Li et al. |
| 8,513,244 B2 | 8/2013 | Gendron et al. |
| 8,536,159 B2 | 9/2013 | Li et al. |
| 8,633,180 B2 | 1/2014 | Li et al. |
| 8,664,207 B2 | 3/2014 | Li et al. |
| 8,697,710 B2 | 4/2014 | Li et al. |
| 8,829,008 B2 | 9/2014 | Li et al. |
| 8,846,693 B2 | 9/2014 | Li et al. |
| 8,859,564 B2 | 10/2014 | Li et al. |
| 8,927,556 B2 | 1/2015 | Li et al. |
| 9,000,001 B2 | 4/2015 | Li et al. |
| 9,006,258 B2 | 4/2015 | Fienberg et al. |
| 9,073,936 B2 | 7/2015 | Li et al. |

(Continued)

FOREIGN PATENT DOCUMENTS

| | | |
|---|---|---|
| DE | 19931206 A1 | 1/2001 |
| DE | 102005042877 | 3/2007 |

(Continued)

OTHER PUBLICATIONS

Abstract of DE102005042877, date of publication of application Mar. 22, 2007, 1 page.
Adamo, et al. "Molecular targets for PDE inhibitor-mediated improvement of cardiac dysfunction in the mdx mouse?" *BMC Pharmacology*, 2011, 11(Suppl 1):O20, 1 page.
Ahn, H. et al., "Potent Tetracyclic Guanine Inhibitors of PDE1 and Pdes Cyclic Guanosine Monophosphate Phosphodiesterases with Oral Antihypertensive Activity," Journal of Medicinal Chemistry, 1997, 40 (14), 2196-2210.
Al-Afaleq, E. et al., "Heterocyclic o-Aminonitriles: Preparation of Pyrazolo[3,4-d]-pyrimidines with Modification of the Substituents at the 1-Position," Molecules, 2001, 6, 621-638.
"Anxiety," [retrieved on May 14, 2008]. Retrieved online via Internet, URL: http://www.nlm.nih.gov/medlineplus/anxiety.html, 5 pages.

(Continued)

*Primary Examiner* — Sarah Pihonak
*Assistant Examiner* — Jason Deck
(74) *Attorney, Agent, or Firm* — Hoxie & Associates LLC

(57) ABSTRACT

The invention relates to the combination of inhibitors of phosphodiesterase 1 (PDE1) and inhibitors of Neprilysin (NEP) useful for the treatment of certain cardiovascular diseases or related disorders, e.g., hypertension, congestive heart disease, and post-myocardial infarction. In another embodiment, the invention relates to the combination of inhibitors of PDE1 and inhibitors of NEP for the treatment of diseases or disorders characterized by disruption of or damage to various cGMP/PKG mediated pathways in the cardiovascular system (e.g., in cardiac tissue or in arterial smooth muscle).

16 Claims, 2 Drawing Sheets

(56) References Cited

U.S. PATENT DOCUMENTS

| | | |
|---|---|---|
| 9,198,924 B2 | 12/2015 | Mates et al. |
| 9,255,099 B2 | 2/2016 | Li et al. |
| 9,546,175 B2 | 1/2017 | Li et al. |
| 2003/0069246 A1 | 4/2003 | Darrow et al. |
| 2003/0092908 A1 | 5/2003 | Pitts et al. |
| 2003/0162782 A1 | 8/2003 | Grossman et al. |
| 2004/0087517 A1 | 5/2004 | Burnet et al. |
| 2004/0259792 A1 | 12/2004 | Palmer et al. |
| 2005/0075795 A1 | 4/2005 | Pandit |
| 2005/0113379 A1 | 5/2005 | Ge et al. |
| 2006/0041014 A1 | 2/2006 | Naylor et al. |
| 2006/0252790 A1 | 11/2006 | Allen et al. |
| 2008/0176961 A1 | 7/2008 | Greengard et al. |
| 2008/0188492 A1 | 8/2008 | Li et al. |
| 2008/0193964 A1 | 8/2008 | Greengard et al. |
| 2008/0194592 A1 | 8/2008 | Mates et al. |
| 2010/0087450 A1 | 4/2010 | Mates et al. |
| 2010/0173878 A1 | 7/2010 | Li et al. |
| 2011/0190373 A1 | 8/2011 | Yan et al. |
| 2011/0237561 A1 | 9/2011 | Li et al. |
| 2011/0312978 A1 | 12/2011 | Davis et al. |
| 2012/0053190 A1 | 3/2012 | Fienberg et al. |
| 2012/0070443 A1 | 3/2012 | Movsesian |
| 2012/0136013 A1 | 5/2012 | Li et al. |
| 2012/0201754 A1 | 8/2012 | Li |
| 2013/0085123 A1 | 4/2013 | Li et al. |
| 2013/0149309 A1 | 6/2013 | Greengard et al. |
| 2013/0239234 A1 | 9/2013 | Greengard et al. |
| 2013/0324565 A1 | 12/2013 | Li et al. |
| 2013/0331363 A1 | 12/2013 | Li et al. |
| 2013/0338124 A1 | 12/2013 | Li et al. |
| 2014/0005155 A1 | 1/2014 | Li et al. |
| 2014/0011783 A1 | 1/2014 | Li et al. |
| 2014/0148421 A1 | 5/2014 | Li et al. |
| 2014/0194396 A1 | 7/2014 | Li et al. |
| 2014/0315868 A1 | 10/2014 | Li et al. |
| 2014/0357606 A1 | 12/2014 | Li et al. |
| 2015/0038474 A1 | 2/2015 | Li et al. |
| 2015/0072965 A1 | 3/2015 | Li et al. |
| 2015/0080357 A1 | 3/2015 | Li et al. |
| 2015/0119370 A1 | 4/2015 | Li et al. |
| 2015/0197524 A1 | 7/2015 | Li et al. |
| 2015/0197528 A1 | 7/2015 | Li et al. |
| 2015/0353556 A1 | 12/2015 | Li et al. |
| 2015/0374699 A1 | 12/2015 | Wennogle et al. |
| 2016/0031895 A1 | 2/2016 | Li et al. |
| 2016/0039835 A1 | 2/2016 | Li et al. |
| 2016/0083390 A1 | 3/2016 | Li et al. |
| 2017/0226117 A1 | 8/2017 | Li et al. |

FOREIGN PATENT DOCUMENTS

| | | | |
|---|---|---|---|
| EP | 0 063 381 A1 | 10/1982 | |
| EP | 0 095 289 A2 | 11/1983 | |
| EP | 0 201 188 A2 | 12/1986 | |
| EP | 0 636 626 A1 | 2/1995 | |
| EP | 0 911 333 A1 | 4/1999 | |
| EP | 1097719 B1 | 12/2004 | |
| JP | 53031694 A | 3/1978 | |
| KR | 10-1991-0006866 | 9/1991 | |
| WO | WO 91/19717 | 12/1991 | |
| WO | WO 94/19351 | 9/1994 | |
| WO | WO 98/46606 | 10/1998 | |
| WO | WO 98/52568 | 11/1998 | |
| WO | WO 01/27113 | 4/2001 | |
| WO | WO 02/074312 | 9/2002 | |
| WO | WO 03/002567 | 1/2003 | |
| WO | WO 03/020702 | 3/2003 | |
| WO | WO 03/020724 | 3/2003 | |
| WO | WO 03/042216 | 5/2003 | |
| WO | WO 2006/133261 | 12/2006 | |
| WO | WO 2006133261 A2 * | 12/2006 | ........... C07D 487/14 |
| WO | WO 2007045663 A2 * | 4/2007 | ........... A61K 31/215 |
| WO | WO 2007/143568 | 12/2007 | |
| WO | WO 2007/143705 | 12/2007 | |
| WO | WO 2008/063505 | 5/2008 | |
| WO | WO 2008/070095 | 6/2008 | |
| WO | WO 2009/073210 | 6/2009 | |
| WO | WO 2009/075784 | 6/2009 | |
| WO | WO 2009/137465 | 11/2009 | |
| WO | WO 2010/065147 | 6/2010 | |
| WO | WO 2010/065148 | 6/2010 | |
| WO | WO 2010/065149 | 6/2010 | |
| WO | WO 2010/065151 | 6/2010 | |
| WO | WO 2010/065153 | 6/2010 | |
| WO | WO 2010/098839 | 9/2010 | |
| WO | WO 2011/016861 | 2/2011 | |
| WO | WO 2011/043816 | 4/2011 | |
| WO | WO 2011/153129 | 12/2011 | |
| WO | WO 2011/153135 | 12/2011 | |
| WO | WO 2011/153136 | 12/2011 | |
| WO | WO 2011/153138 | 12/2011 | |
| WO | WO 2012/171016 | 12/2012 | |
| WO | WO 2013/039985 | 3/2013 | |
| WO | WO 2013/192556 | 12/2013 | |
| WO | WO 2014/151409 | 9/2014 | |
| WO | WO 2016/022893 | 2/2016 | |

OTHER PUBLICATIONS

Aswar, M. et al., "Anti-Cataleptic Activity of Various Extracts of *Ocimum sanctum*," International Journal of Pharmaceutical Research and Development, 2010, 2 (6), 7 pages.

"Autism," [retrieved on May 14, 2008]. Retrieved online via Internet, URL: http://www.nlm.nih.gov/medlineplus/autism.html, 6 pages.

Banker, Gilbert S. et al., Eds., Modern Pharmaceutics, Third Edition, Marcel Dekker Inc., New York, 1996.

Bastia, E. et al., "Effect of $A_1$ and $A_{2A}$ Adenosine Receptor Ligands in Mouse Acute Models of Pain," Neuroscience Letters, 2002, 328, 241-244.

Bender, A. et al., "Cyclic Nucleotide Phosphodiesterases: Molecular Regulation to Clinical Use," Pharmacological Reviews, 2006, 58 (3), 488-520.

Bender et al., *PNAS* 102(2):497-502 (2005).

Blokland, A. et al., "PDE Inhibition and Cognition Enhancement," 2012, 22 (4), 349-354 (abstract only).

Boyd, K. et al., "Dopamine Receptor Signaling and Current and Future Antipsychotic Drugs" in Current Antipsychotics, Handbook of Experimental Pharmacology, 212, Gross, G. et al., Eds., doi:10. 1007/978-3-642-25761-2_3, Springer-Verlag, Berlin, 2012, pp. 53-86.

Burnouf, C. et al., "Synthesis, Structure-Activity Relationships, and Pharmacological Profile of 9-Amino-4-oxo-1-phenyl-3,4,6,7-tetrahydro[1,4]diazepino[6,7,1-hi]indoles: Discovery of Potent, Selective Phosphodiesterase Type 4 Inhibitors," Journal of Medicinal Chemistry, 2000, 43 (25), 4850-4867.

Chalimoniuk, M. et al., "Upregulation of Guanylyl Cyclase Expression and Activity in Striatum of MPTP-induced Parkinsonism in Mice," Biochemical and Biophysical Research Communications, 2004, 324, 118-126.

Chebib, M. et al., "1-Phenylpyrazolo[3,4-d]pyrimidines; Structure-Activity Relationships for C6 Substituents at $A_1$ and $A_{2A}$ Adenosine Receptors," Bioorganic & Medicinal Chemistry, 2000, 8, 2581-2590.

Chen, M. et al., "Effects of Bimatoprost 0.03% on Ocular Hemodynamics in Normal Tension Glaucoma," Journal of Ocular Pharmacology and Therapeutics, 2006, 22 (3), 188-193.

Chermat, R. et al., "Adaptation of the Tail Suspension Test to the Rat," Journal de Pharmacologie (Paris), 1986, 17 (3), 348-350.

Deshmukh, R. et al., "Amelioration of Intracerebroventricular Streptozotocin Induced Cognitive Dysfunction and Oxidative Stress by Vinpocetine—A PDE1 Inhibitor," European Journal of Pharmacology, 2009, 620 (1-3), 49-56.

Dewald, H. et al., "Synthesis and Potential Antipsychotic Activity of 1H-Imidazo[1,2-c]pyrazolo[3,4-e]pyrimidines," Journal of Medicinal Chemistry, 1988, 31, 454-461.

Ehrman, L. et al., "Phosphodiesterase 1B Differentially Modulates the Effects of Methamphetamine on Locomotor Activity and Spatial

(56) References Cited

OTHER PUBLICATIONS

Learning Through DARPP32-Dependent Pathways: Evidence from PDE1B-DARPP32 Double-Knockout Mice," Genes, Brain and Behavior, 2006, 5 (7), 540-551.
Ennaceur, A. et al., "A New One-Trial Test for Neurobiological Studies of Memory in Rats. 1:Behavioral Data," Behavioral Brain Research, 1998, 31, 47-59.
Evgenov, et al., *Am. J. Physiol. Lung Cell Mol. Physiol.*, 290(4):L723-L729 (2006).
Fienberg, A. et al., "DARPP-32: Regulator of the Efficacy of Dopaminergic Neurotransmission," Science, 1998, 281, 838-842.
Filgueiras, C. et al., "Phosphodiesterase Type 1 Inhibition Improves Learning in Rats Exposed to Alcohol During the Third Trimester Equivalent of Human Gestation," Neuroscience Letters, 2010, 473 (3), 202-207.
Gelbin, M. et al., "Ketene-S,N-acetals as Synthons for Heterocycles, New Synthesis of Pyrimidinones," Journal Für Praktische Chemie, 1987, 329 (5), 753-766.
Ghorab, M.M. et al, Synthesis, anticancer and radioprotective activities of some new pyrazolo[3,4-d]pyrimidines containing amino acid moieties, Arzneimittel Forschung, 2009, vol. 59, No. 2, pp. 96-103.
Goodman & Gilman, Las bases farmacológicas de la terapéutica (The Pharmacological Basis of Therapeutics), McGraw-Hill Interamericana, 2007, p. 892, cited within text of Opposition to Letters Patent in Costa Rican Patent Application No. 2011-0313, 7 pages.
Greengard, P. et al., "Beyond the Dopamine Receptor: The DARPP-32/Protein Phosphatase-1 Cascade," Neuron, 1999, 23, 435-447.
Han, P. et al., "The Calcium/Calmodulin-dependent Phosphodiesterase PDE1C Down-regulates Glucose-induced Insulin Secretion," The Journal of Biological Chemistry, 1999, 274 (32), 22337-22344.
Hulley, P. et al., "Cyclic AMP Promotes the Survival of Dopaminergic Neurons in vitro and Protects Them from the Toxic Effects of MPP+," Journal of Neural Transmission [Supplemental], 1995, 46, 217-228.
Japanese Patent Office, Patent Abstracts of Japan, Abstract for JP 53031694 A, Date of publication of application Mar. 25, 1978, 1 page.
Jiang, M. et al., "Chemoenzymatic Asymmetric Total Synthesis of Phosphodiesterase Inhibitors: Preparation of a Polycyclic Pyrazolo[3,4-d]pyrimidine from an Acylnitroso Diels-Alder Cycloadduct-Derived Aminocyclopentenol," Journal of Organic Chemistry, 2005, 70, 2824-2827.
Kakkar, R. et al., "Inhibition of Bovine Brain Calmodulin-Dependent Cyclic Nucleotide Phosphodiesterase Isozymes by Deprenyl," Life Sciences, 1996, 59 (21), 337-341.
Kakkar, R. et al. "Amantadine: An Antiparkinsonian Agent Inhibits Bovine Brain 60 kDa Calmodulin-Dependent Cyclic Nucleotide Phosphodiesterase Isozyme," Brain Research, 1997, 749 (2), 290-294.
Kakkar, R. et al. "Calmodulin-dependent Cyclic Nucleotide Phosphodiesterase (PDE1)," CMLS Cellular and Molecular Life Sciences, 1999, 55 (8-9), 1164-1186.
Kim, et al., *Circulation*, 104, 19:2338-2343, 2001.
Klaissle, P. et al., "Physical Activity and Environmental Enrichment Regulate the Generation of Neural Precursors in the Adult Mouse Substantia Nigra in a Dopamine-dependent Manner," BMC Neuroscience, 2012, 13, 132, doi:10.1186/1471-2202-13-132, 15 pages.
Kleppisch, T., "Phosphodiesterases in the Central Nervous System" in cGMP: Generators, Effectors and Therapuetic Implications, Handbook of Experimental Pharmacology, 191, Schmidt, H. et al., Eds., Springer-Verlag, Berlin, 2009, pp. 71-92.
Laddha, S. et al., "A New Therapeutic Approach in Parkinson's Disease: Some Novel Quinazoline Derivatives as Dual Selective Phosphodiesterase 1 Inhibitors and Anti-inflammatory Agents" Bioorganic & Medicinal Chemistry, 2009, 17 (19), 6796-6802.
Lundqvist, T. et al., "Exploitation of Structural and Regulatory Diversity in Glutamate Racemases," Nature, 2007, 447, 817-822.

Mani, S. et al., "Requirement for DARPP-32 in Progesterone Facilitated Sexual Receptivity in Female Rats and Mice," Science, 2000, 287, 1053-1056.
Medina, A., "Therapeutic Utility of Phosphodiesterase Type 1 Inhibitors in Neurological Conditions," Frontiers in Neuroscience, 2011, 5, 21, 6 pages.
Miller, et al. "Cyclic nucleotide phosphodiesterase 1A: a key regulator of cardiac fibroblast activation and extracellular matrix remodeling in the heart," Basic Res Cardiol, 2011, 106(6): 1023-1039, doi:10.1007/s00395-011-0228-2.
Miller, et al., *Circ. Res.*, 105(10):956-964 (2009).
Mokni, et al., *Plos. One.* 5(12):e14227 (2010).
Murray, T. et al., "LY503430, A Novel □-Amino-3-hydroxy-5-methylisoxazole-4-propionic Acid Receptor Potentiator with Functional, Neuroprotective and Neurotrophic Effects in Rodent Models of Parkinson's Disease," The Journal of Pharmacology and Experimental Therapeutics, 2003, 306 (2), 752-762.
Murray "Expression and activity of cAMP phosphodiesterase isoforms in pulmonary artery smooth muscle cells from patients with pulmonary hypertension: role for PDE1," *AM J Physiol Lung Cell Mol Physiol*, 292: L294-L303 (2007).
Nishi, A. et al., "Advanced Research on Dopamine Signaling to Develop Drugs for the Treatment of Mental Disorders: Biochemical and Behavioral Profiles of Phosphodiesterase Inhibition in Dopaminergic Neurotransmission," Journal of Pharmacological Sciences, 2010, 114, 6-16.
Noguchi, M. et al., "A Facile Preparation of 7-(Substituted Amino-)-6H-pyrrolo[3,4-d]-pyrimidine Derivatives," Bulletin of the Chemical Society of Japan, 1989, 62 (9), 3043-3045.
Pardo, C. et al., "Synthesis of 1-(p-Nitrobenzyl)Azoles and 1-(p-Nitrobenzyl)Benzazoles," OPPI Briefs, 2000, 32 (4), 385-390.
Park, E, et al., "Traumatic Brain Injury: Can the Consequences Be Stopped?" CMAJ, 2008, 178 (9), 1163-1170.
Patani et al., "Bioisosterism: A Rational Approach in Drug Design", Chem. Rev. 1996, 96, 3147-3176.
Polli, J. et al., "Expression of a Calmodulin-dependent Phosphodiesterase Isoform (PDE1B1) Correlates With Brain Regions Having Extensive Dopaminergic Innervation," The Journal of Neuroscience, 1994, 14 (3), 1251-1261.
Porsolt, R. et al., "Depression: A New Animal Model Sensitive to Antidepressant Treatments," Nature, 1977, 266, 730-732.
Poulsen, S. et al., "High-Pressure Synthesis of Enantiomerically Pure C-6 Substituted Pyrazolo[3,4-d]pyrimidines," Biorganic & Medicinal Chemistry Letters, 2001, 11, 191-193.
Prickaerts, J. et al., "Possible Role of Nitric Oxide-Cyclic GMP Pathway in Object Recognition Memory: Effects of 7-Nitroindazole and Zaprinast," European Journal of Pharmacology, 1997, 337, 125-136.
Reed, T. et al., "Phosphodiesterase 1B Knock-Out Mice Exhibit Exaggerated Locomotor Hyperactivity and DARPP-32 Phosphorylation in Response to Dopamine Agonists and Display Impaired Spatial Learning," The Journal of Neuroscience, 2002, 22 (12), 5188-5197.
Rybalkin, S. et al., "Cyclic GMP Phosphodiesterases and Regulation of Smooth Muscle Function," Circulation Research, 2003, 93, 280-291.
Schmidt, C., "Phosphodiesterase Inhibitors as Potential Cognition Enhancing Agents," Current Topics in Medicinal Chemistry, 2010, 10 (2), 222-230.
Schermuly, *Circulation*, 115(17) 2331-2339 (2007).
Sharma, R. et al., "Regulation of Calmodulin-Stimulated Cyclic Nucleotide Phosphodiesterase (PDE1): Review," International Journal of Molecular Medicine, 2006, 18, 95-105.
Shimizu, K. et al., "Calmodulin-Dependent Cyclic Nucleotide Phosphodiesterase (PDE1) Is a Pharmacological Target of Differentiation-Inducing Factor-1, an Antitumor Agent Isolated from *Dictyostelium*," Cancer Research, 2004, 64, 2568-2571.
Shook, B. et al., "Design and Characterization of Optimized Adenosine $A_{2A}/A_1$ Receptor Antagonists for the Treatment of Parkinson's Disease," Journal of Medicinal Chemistry, doi:10.1021/jm201640m, 2012, 47 pages.
Sonnenberg, et al. "Identification of Protease 3.4.24.11 as the Major Atrial Natriuretic Facto Degrading Enzyme in the Rat Kidney," *Peptides*, vol. 9, pp. 173-180, 1988.

(56) References Cited

OTHER PUBLICATIONS

Takimoto, E., "Controlling Myocyte cGMP: Phosphodiesterase 1 Joins the Fray," Circ Res., 2009, 105(10):931-933.
Turko, I. et al., "Inhibition of Cyclic GMP-Binding Cyclic GMP-Specific Phosphodiesterase (Type 5) by Sildenafil and Related Compounds," Molecular Pharmacology, 1999, 56, 124-130.
Ungerstedt, U. et al., "Quantitative Recording of Rotational Behavior in Rats After 6-Hydroxy-dopamine Lesions of the Nigrostriatal Dopamine System," Brain Research, 1970, 24, 485-493.
Ungerstedt, U., "Stereotaxic Mapping of the Monoamine Pathways in the Rat Brain," Acta Physiologica Scandinavica, Supplementum 367, 1971, 1-48.
Vatter, S. et al., "Differential Phosphodiesterase Expression and Cytosolic $Ca^{2+}$ in Human CNS Tumour Cells and in Non-Malignant and Malignant Cells of Rat Origin," Journal of Neurochemistry, 2005, 93, 321-329.
Willerson et al., *Circulation* 109:11-2-11-10 (2004).
Wolff, Burger's Medicinal Chemistry and Drug Discovery, Fifth Edition, vol. I: Principles and Practice, John Wiley & Sons, New York, 1995, 975-977.
Xia et al., "Synthesis and Evaluation of Polycyclic Pyrazolo[3,4-d]pyrimidines as PDE1 and PDE5 cGMP Phosphodiesterase Inhibitors," Journal of Medicinal Chemistry, 1997, 40, 4372-4377.
Youdim et al., "The Path from Anti Parkinson Drug Selegiline and Rasagiline to Multi-functional Neuroprotective Anti Alzheimer Drugs Ladostigil and M30," Current Alzheimer Research, 2006, 3, 541-550.
Zhang, et al. "Phosphodiesterases and cardiac cGMP: evolving roles and controversies," *Trends in Pharmacological Sciences*, 2011, vol. 32, No. 6, 360-365.

\* cited by examiner

COMBINATIONS OF PDE1 INHIBITORS AND NEP INHIBITORS AND ASSOCIATED METHODS

CROSS-REFERENCE TO RELATED APPLICATIONS

This application claims priority to and the benefit of U.S. Provisional Application No. 62/034,665, filed on Aug. 7, 2014, the contents of which are hereby incorporated by reference in its entirety.

FIELD OF THE INVENTION

The field relates to the combination of inhibitors of phosphodiesterase 1 (PDE1) and inhibitors of Neprilysin (neutral endopeptidase or NEP) useful for the treatment of certain cardiovascular diseases and related disorders, e.g., hypertension, congestive heart disease, and post-myocardial infarction. The field further relates to the administration of inhibitors of phosphodiesterase 1 (PDE1) in combination with inhibitors of NEP for the treatment of diseases or disorders characterized by disruption of or damage to certain cGMP/PKG mediated pathways in the cardiovascular system (e.g., in cardiac tissue or in vascular smooth muscle).

BACKGROUND OF THE INVENTION

Heart disease is a chronic and progressive illness that kills more than 2.4 million Americans each year. There are approximately 500,000 new cases of heart failure per year, with an estimated 5 million patients in the United States alone having this disease. Early intervention is likely to be most effective in preserving cardiac function. It would be most desirable to prevent as well to reverse the morphological, cellular, and molecular remodeling that is associated with heart disease. Some of the most important indicators of cardiac risk are age, hereditary factors, weight, smoking, blood pressure, exercise history, and diabetes. Other indicators of cardiac risk include the patient's lipid profile, which is typically assayed using a Hood test, or any other biomarker associated with heart disease or hypertension. Other methods for assaying cardiac risk include, but are not limited to, an EKG stress test, thallium stress test, EKG, computed tomography scan, echocardiogram, magnetic resonance imaging study, non-invasive and invasive arteriogram, and cardiac catheterization.

Pulmonary hypertension (PH or PHT) is an increase in blood pressure in the pulmonary artery, pulmonary vein, and/or pulmonary capillaries. It is a very serious condition, potentially leading to shortness of breath, dizziness, fainting, decreased exercise tolerance, heart failure, pulmonary edema, and death. It can be one of five different groups, classified by the World Health Organization as follows:

WHO Group I—Pulmonary arterial hypertension (PAH)
a. Idiopathic (IPAH)
b. Familial (FPAH)
c. Associated with other diseases (APAH): collagen vascular disease (e.g. scleroderma), congenital shunts between the systemic and pulmonary circulation, portal hypertension, HIV infection, drugs, toxins, or other diseases or disorder.
d. Associated with venous or capillary disease Pulmonary arterial hypertension involves the vasoconstriction or tightening of blood vessels connected to and within the lungs. This makes it harder for the heart to pump blood through the lungs, much as it is harder to make water flow through a narrow pipe as opposed to a wide one. Over time, the affected blood vessels become both stiffer and thicker, in a process known as fibrosis. This further increases the blood pressure within the lungs and impairs pulmonary blood flow. In addition, the increased workload of the heart causes thickening and enlargement of the right ventricle, making the heart less able to pump blood through the lungs, causing right heart failure. As the blood flow through the lungs decreases, the left side of the heart receives less blood. This blood may also carry less oxygen than normal. Therefore it becomes more and more difficult for the left side of the heart to pump to supply sufficient oxygen to the rest of the body, especially during physical activity.

WHO Group II—Pulmonary hypertension associated with left heart disease
a. Atrial or ventricular disease
b. Valvular disease (e.g. mitral stenosis)

In WHO Group II pulmonary hypertension there may not be any obstruction to blood flow in the lungs. Instead, the left heart fails to pump blood efficiently out of the heart into the body, leading to pooling of blood in veins leading from the lungs to the left heart (congestive heart failure or CHF). This causes pulmonary edema and pleural effusions. The fluid build-up and damage to the lungs may also lead to hypoxia and consequent vasoconstriction of the pulmonary arteries, so that the pathology may come to resemble that of Group I or III.

WHO Group III—Pulmonary hypertension associated with lung diseases and/or hypoxemia
a. Chronic obstructive pulmonary disease (COPD), interstitial lung disease (ILD)
b. Sleep-disordered breathing, alveolar hypoventilation
c. Chronic exposure to high altitude
d. Developmental lung abnormalities In hypoxic pulmonary hypertension (WHO Group III), the low levels of oxygen may cause vasoconstriction or tightening of pulmonary arteries. This leads to a similar pathophysiology as pulmonary arterial hypertension.

WHO Group IV—Pulmonary hypertension due to chronic thrombotic and/or embolic disease
a. Pulmonary embolism in the proximal or distal pulmonary arteries
b. Embolization of other matter, such as tumor cells or parasite In chronic thromboembolic pulmonary hypertension (WHO Group IV), the blood vessels are blocked or narrowed with blood clots. Again, this leads to a similar pathophysiology as pulmonary arterial hypertension.

WHO Group V—Miscellaneous

Treatment of pulmonary hypertension has proven very difficult.

Antihypertensive drugs that work by dilating the peripheral arteries are frequently ineffective on the pulmonary vasculature. For example, calcium channel blockers are effective in only about 5% of patients with IPAH. Left ventricular function can often be improved by the use of diuretics, beta blockers, ACE inhibitors, etc., or by repair/replacement of the mitral valve or aortic valve. Where there is pulmonary arterial hypertension, treatment is more challenging. Lifestyle changes, digoxin, diuretics, oral anticoagulants, and oxygen therapy are conventional, but not highly effective. Newer drugs targeting the pulmonary arteries include endothelin receptor antagonists (e.g., bosentan, sitaxentan, ambrisentan), phosphodiesterase type 5 inhibitors (e.g., sildenafil, tadalafil), prostacyclin derivatives (e.g., epoprostenol, treprostinil, iloprost, beraprost), and soluble guanylate cyclase (sGC) activators (e.g., cinaciguat and riociguat). Surgical approaches to PAH include atrial septostomy to create a communication between the right and left atria, thereby relieving pressure on the right side of the heart, but at the cost of lower oxygen levels in blood (hypoxia); lung transplantation; and pulmonary thromboendarterectomy (PTE) to remove large clots along with the lining of the pulmonary artery. Heart failure and acute myocardial infarction are common and serious conditions frequently associated with thrombosis and/or plaque build-up in the coronary arteries.

Hypertension accounts for 9.4 million cardiovascular deaths annually worldwide. The disease affects more than two-thirds of people 65 years of age or older. The effective treatment of hypertension has been shown to reduce the risk of morbidity and mortality associated with elevated blood pressure, including stroke, ischemic heart disease, heart failure, and chronic kidney disease. Despite the availability of multiple drug classes of diverse mechanisms of action to treat hypertension, hypertension remains an inadequately controlled disease, especially systolic hypertension.

In young people, hypertension is predominantly due to increased diastolic blood pressure and increased mean arterial pressure, whereas in older patients, hypertension is primarily due to increased systolic blood pressure due to a loss of elasticity in large arteries such as the aorta. In older patients, the diastolic blood pressure may also drop, resulting in increased pulse pressure, independent of changes in mean arterial pressure. Control of systolic blood pressure remains the most important unmet need in the clinical management of hypertension.

The final common pathway of cardiovascular disease is heart failure, which is often mediated by progressive uncontrolled hypertension. The recent ALLHAT study found that the development of heart failure in hypertensive patients was a powerful predictor for increased mortality.

Cardiovascular disease or dysfunction may also be associated with diseases or disorders typically thought of as affecting skeletal muscle. One such disease is Duchenne muscular dystrophy (DMD), which is a disorder that primarily affects skeletal muscle development but can also result in cardiac dysfunction and cardiomyopathy. DMD is a recessive X-linked form of muscular dystrophy, affecting around 1 in 3,600 boys, which results in muscle degeneration and eventual death. The disorder is caused by a mutation in the dystrophin gene, located on the human X chromosome, which codes for the protein dystrophin, an important structural component within muscle tissue that provides structural stability to the dystroglycan complex (DGC) of the cell membrane. While both sexes can carry the mutation, females rarely exhibit signs of the disease.

Patients with DMD either lack expression of the protein dystrophin or express inappropriately spliced dystrophin, as a result of mutations in the X-linked dystrophin gene. Additionally, the loss of dystrophin leads to severe skeletal muscle pathologies as well as cardiomyopathy, which manifests as congestive heart failure and arrhythmias. The absence of a functional dystrophin protein is believed to lead to reduced expression and mis-localization of dystrophin-associated proteins including Neuronal Nitric Oxide (NO) Synthase (nNOS). Disruption of nNOS signaling may result in muscle fatigue and unopposed sympathetic vasoconstriction during exercise, thereby increasing contraction-induced damage in dystrophin-deficient muscles. The loss of normal nNOS signaling during exercise is central to the vascular dysfunction proposed to be an important pathogenic mechanism in DMD. Eventual loss of cardiac function often leads to heart failure in DMD patients.

Currently, there is a largely unmet need for an effective way of treating cardiovascular disease and disorders (e.g. congestive heart disease, hypertension and post-myocardial infarction) and diseases and disorders which may result in cardiac dysfunction or cardiomyopathy (e.g., Duchenne Muscular Dystrophy). Improved therapeutic compositions and methods for the treatment of cardiac conditions and dysfunction are urgently required. Effective treatments for heart failure with preserved ejection fraction (HF-PEF) are particularly needed.

Eleven families of phosphodiesterases (PDEs) have been identified but only PDEs in Family I, the $Ca^{2+}$/calmodulin-dependent phosphodiesterases (CaM-PDEs), which are activated by $Ca^{2+}$/calmodulin and have been shown to mediate the calcium and cyclic nucleotide (e.g. cGMP and cAMP) signaling pathways. The three known CaM-PDE genes, PDE1A, PDE1B, and PDE1C, are all expressed in central nervous system tissue, as well as in heart, lung, and smooth muscle to varying degrees. PDE1A is expressed in the brain, lung and heart. PDE1B is primarily expressed in the central nervous system, but it also detected in the heart, is present in neutrophils and has been shown to be involved in inflammatory responses of this cell. PDE1C is expressed in olfactory epithelium, cerebellar granule cells, striatum, heart, and vascular smooth muscle. PDE1C is a major phosphodiesterase in the human cardiac myocyte.

Of all of the PDE families, the major PDE activity in the human cardiac ventricle is PDE1. Generally, there is a high abundance of PDE1 isoforms in: cardiac myocytes, vascular endothelial cells, smooth muscle cells, fibroblasts and motor neurons. Upregulation of phosphodiesterase 1A expression is associated with the development of nitrate tolerance. Kim et al., *Circulation* 104(19:2338-2343 (2001). Cyclic nucleotide phosphodiesterase 1C promotes human arterial smooth muscle cell proliferation. Rybalkin et al., *Circ. Res.* 90(2): 151-157 (2002). The cardiac ischemia-reperfusion rat model also shows an increase in PDE1 activity. Kakkar et al., *can. J. Physiol. Pharmacol.* 80(1):59-66 (2002). $Ca^{2+}$/CaM-stimulated PDE1, particularly PDE1A has been shown to be involved in regulating pathological cardiomyocyte hypertrophy. Millet et al., *Circ. Res.* 105(10):956-964 (2009). Early cardiac hypertrophy induced by angiotensin II is accompanied by 140% increases in PDE1A in a rat model of heart failure. Mokni et al., *Plos. One.* 5(12):e14227 (2010). Inhibition of phosphodiesterase 1 augments the pulmonary vasodilator response to inhaled nitric oxide in awake lambs with acute pulmonary hypertension. Evgenov et al., *Am. J. Physiol. Lung Cell. Mol. Physiol.* 290(4):L723-L729 (2006). Strong upregulation of the PDE1 family in pulmonary artery smooth muscle cells is also noted in human idiopathic PAH lungs and lungs from animal models of PAH. Schermuly et al., *Circulation* 115(17)2331-2339 (2007). PDE1B2, which is present in neutrophils, is up-regulated during the process of differentiation from neutrophils to macrophases. Bender et al., *PNAS* 102(2):497-502 (2005). The differentiation of monocytes to macrophage, in turn, is involved in the inflammatory component of heart disease, particularly athero-thrombosis, the underlying cause of approximately 80% of all sudden cardiac death. Willerson et al., *Circulation* 109: II-2-II-10 (2004).

Cyclic nucleotide phosphodiesterases down-regulate intracellular cAMP and cGMP signaling by hydrolyzing these cyclic nucleotides to their respective 5'-monophosphates (5'AMP and 5'GMP), which are inactive. PDE1A and PDE1B preferentially hydrolyze cGMP over cAMP, while PDE1C shows approximately equal cGMP and cAMP hydrolysis. cAMP and cGMP are both central intracellular second-messengers and they play roles in regulating numerous cellular functions. In the cardiac myocyte, cGMP mediates the effects of nitric oxide and atrial natriuretic peptide (ANP). Each cyclic nucleotide has a corresponding primary targeted protein kinase, PKA for cAMP, and PKG for cGMP. PKG acts as a brake in the heart, and is capable of countering cAMP-PKA mediated contractile stimulation and inhibiting hypertrophy. Importantly, the duration and magnitude of these signaling cascades are determined not only by generation of cyclic nucleotides, but also by their hydrolysis catalyzed by phosphodiesterases (PDEs). PDE regulation is quite potent—often suppressing an acute rise in a given cyclic nucleotide back to baseline within seconds. It is also compartmentalized within the cell, so that specific targeted proteins can be regulated by the same "generic" cyclic nucleotide. By virtue of its modulation of cGMP in the myocyte, PDE1 participates in hypertrophy regulation. (Circ Res. 2009 Nov. 6; 105(10): 931.)

PDE1 has been shown to be up-regulated in early cardiac hypertrophy induced by the pro-hypertensive hormone angiotensin II (Ang-II), and to be up-regulated in pulmonary smooth muscle cells in animal models of pulmonary hypertension and in human patients. The reasonably selective PDE1 inhibitor dioclein has also been shown to induce PKG-dependent vasodilation, while other PDE1 inhibitors have been shown to reduce lung vascular remodeling and right heart hypertrophy in animal models.

Neutral endopeptidase, also known as Neprilysin or NEP (EC 3.4.24.11), is a type II integral membrane zinc-dependent metalloendoprotease that cleaves a variety of short peptide substrates. In mammals, NEP is widely expressed, including in the kidney, lung, endothelial cells, vascular smooth muscle cells, cardiac myocytes, fibroblasts, adipocytes and brain. The highest concentrations are found in the proximal renal tubules of the kidney. Among its natural targets are cardiac atrial natriuretic peptide (ANP), B-type natriuretic peptide (BNP), C-type natriuretic peptide (CNP), angiotensin I (Ang-I), angiotensin II (Ang-II), bradykinin (BK), and endothelin (ET). Cleavage of these peptides by NEP results in their inactivation, attenuating the peptides' natural biological effects.

ANP, BNP and CNP are all part of the natriuretic peptide (NP) system, which, along with the renin-angiotensin system, is a major component of mammalian blood pressure homeostasis. While the renin-angiotensin system is primarily responsible for increasing blood pressure (e.g., by promoting vasoconstriction and water retention), the natriuretic peptide system is primarily responsible for decreasing blood pressure (e.g., by promoting vasodilation and natriuresis). ANP and BNP are both powerful vasodilators and strong promoters of decreased renal reabsorption of sodium and water in a potassium-sparing manner. These dual effects exert a powerful blood pressure lowering effect. BNP and CNP also exert an anti-fibrotic effect and an anti-hypertrophic effect in the heart. CNP shares the vasodilatory effects of ANP/BNP but without the renal effects. In addition, both hypertension and obesity have been shown to be associated with reduced ANP and BNP levels, and a specific genetic variant of ANP (rs5068), which increases ANP levels, has been shown to protect against hypertension and metabolic syndrome. Thus, ANP, BNP and CNP play an important role in blood pressure homeostasis and cardiovascular health.

Inhibition of NEP results in an increase in the half-lives of circulating ANP, BNP and CNP. This is expected to prolong their blood-pressure lowering and cardiac health improving effects. Urine cAMP levels are significantly elevated after systemic administration of NEP inhibitors.

Inhibition of NEP also results in higher levels of bradykinin, angiotensin I, angiotensin II and endothelin. Importantly, endothelin and angiotensin II are strongly pro-hypertensive peptides. Thus, NEP inhibition alone results in both vasodilatory effects (from the NPs) and vasoconstrictive effects (from increased Ang-II and ET). These pro-hypertensive peptides all operate via binding to G-protein coupled receptors (GPCRs). The major contributor to this vasoconstrictive effect is Angiotensin-II, which operates via binding to the G-protein coupled receptors $AT_1$ and $AT_2$. These receptors exert their physiological effects through activation of phospholipase C (PLC) and protein kinase C (PKC) signaling cascades. Bradykinin is inactivated to a large extent by angiotensin converting enzyme, and ACE inhibitors cause congestion as a major side effect that is not seen with NEP inhibitors.

ANP, BNP and CNP all function via the second messenger cGMP. ANP and BNP bind to membrane-bound guanylyl cyclase-A, while CNP binds to guanylyl cyclase B. Both of these enzymes increase intracellular cGMP in response to receptor binding. The increased cGMP concentration activates protein kinase G (PKG) which is responsible for exerting the downstream biological effects of the natriuretic peptides.

Several NEP inhibitors are known, including candoxatril, candoxatrilat, omapatrilat, gempatrilat, and sampatrilat. Candoxatril had been shown to produce a dose-dependent increase in both plasma ANP and cGMP levels, and although it is safe, it does not produce a stable blood-pressure lowering effect. This is thought to be due to the effects of NEP inhibition on BK, ET and Ang-II breakdown. Candoxatril treatment in patients with heart failure has been shown to increase levels of endothelin significantly, thus cancelling out the blood pressure effects caused by increased ANP.

In contrast to candoxatril and candoxatrilat, omapatrilat is considered a vasopeptidase inhibitor (VPI), because it functions to an equal extent as both an NEP inhibitor and an ACE (angiotensin converting enzyme) inhibitor. ACE is the enzyme that is responsible for converting Ang-I to Ang-II, which is the major pro-hypertensive hormone of the renin-angiotensin system. By inhibiting both NEP and ACE, it was thought that the increase in Ang-II caused by NEP inhibition would be negated, resulting in a highly effective antihypertensive treatment. Clinical studies, however, showed that omapatrilat was associated with a severe incidence of angioedema (a known side effect of ACE inhibitors). Later research has indicated that this may be due to concomitant inhibition of aminopeptidase P (APP). ACE, APP and NEP all contribute to the breakdown of bradykinin, which is another anti-hypertensive peptide, and the over-accumulation of bradykinin resulting from simultaneous inhibition of three of its degradation pathways may be a strong factor leading to angioedema.

The combination of a PDE1 inhibitor with an NEP inhibitor has been disclosed for the treatment of female sexual dysfunction (see European application publication EP 1 097 719 B1). The combination of the non-selective inhibitor vinpocetine (which also inhibits I-kappaB kinase) with an NEP inhibitor has been disclosed for treatment of serine protease-associated diseases, e.g., cardiac hypertrophy, hypertension, etc. (see WO 2013/039985). The combination of certain NEP inhibitors with phosphodiesterase inhibitors generally, and PDE5 inhibitors particularly, has been disclosed for the treatment of certain diseases including hypertension and heart failure (see U.S. Pat. No. 8,513,244). The combination of PDE1 inhibitors with dual NEP/ACE inhibitors (VPI's, such as omapatrilat) has been disclosed for the treatment of pathologic cardiac remodeling and heart failure (See US Patent Application Publication 2011/0190373). The use of a selective PDE5 inhibitor with an NEP inhibitor has been disclosed for the treatment of male sexual dysfunction (see US Patent Application Publication 2006/0041014).

Recently, the combination use of NEP inhibitors with angiotensin-II receptor blockers (ARBs) has been suggested for the treatment of hypertension. LCZ696 is a combination product containing the ARB valsartan with the NEP inhibitor AHU-377. This is another effort to get around the angiotensin-II mediated blood pressure effects caused by NEP inhibition, and the combination is currently undergoing clinical trials.

SUMMARY OF THE INVENTION

The present invention relates to the use of a PDE1 inhibitor in combination with a NEP inhibitor for the treatment of cardiac diseases and disorders, including, e.g., hypertension, heart failure, post-myocardial infarction management, cardiac hypertrophy and Duchenne Muscular Dystrophy (DMD). In a preferred embodiment, either the PDE1 inhibitor or the NEP inhibitor is selective. In a more preferred embodiment, both the PDE1 inhibitor and the NEP inhibitor are selective. Without being bound by theory, it is believed that the PDE1 inhibitors described are involved in regulating cGMP/PKG involvement in cardiac hypertrophy. Previous studies have demonstrated that intracellular $Ca^{2+}$/CaM-dependent signaling promotes maladaptive hypertrophic gene expression in cardiomyocytes through various effectors such as the protein phosphatase calcineurin, $Ca^{2+}$/CaM-dependent kinase II (CaMKII). Without being bound by any theory, endogenous cGMP/PKG-dependent signaling may be able to negatively regulate cardiac hypertrophy, by suppressing Gq/11 activation and normalizing $Ca^{2+}$ signaling. $Ca^{2+}$/CaM, by activating PDE1, may decrease cGMP levels and PKG activity. In turn, this process may lead to potentiated cardiomyocyte hypertrophy. Additionally, upregulation of PDE1 expression upon neurohormonal or biomechanical stress during cardiac hypertrophy may further enhance PDE1 activity and attenuates cGMP/PKG signaling. In addition, the natriuretic peptides, and in particular C-type natriuretic peptide (CNP), are known to also exert anti-hypertrophic effects in cardiac tissues. These effects exerted by the natriuretic peptides are exerted via a cGMP signaling cascade. Accordingly, without being bound by any theory, it is believed that inhibition of PDE1, for example, could reverse or prevent the attenuation of cGMP/PKG signaling that contributes to cardiomyocyte hypertrophy. Such reversal or prevention of the attenuation of cGMP signaling would concomitantly and synergistically increase the anti-hypertrophic effects of the natriuretic peptides. Therefore, administration of a PDE1 inhibitor as described herein in combination with an NEP inhibitor, could provide a potential means to regulate cardiac hypertrophy, and by extension provide a treatment for various cardiovascular diseases and disorders.

In another embodiment, without being bound by theory, it is believed that PDE1 inhibitors, through their regulation of cGMP signaling cascades in vascular smooth muscle cells (e.g., induction of cGMP-mediated vasodilation), in combination with the effects of circulating ANP, BMP and/or CMP on the same smooth muscle cells, potentiated by the effects of NEP inhibition, will synergistically improve blood pressure. In a further embodiment, it is systolic blood pressure in particular that is improved. In yet a further embodiment, blood pressure and pulse pressure are both improved.

Without being bound by theory, the combination of a PDE1 inhibitor with a selective NEP inhibitor (not a VPI) should realize the full positive effects of NEP inhibition (increased ANP, BNP and CNP half-life), further enhanced by the potentiation of the NP signaling cascades (mediated by cGMP) caused by PDE1 inhibition, without the negative effects of NEP inhibition that can lead to decreased efficacy.

Accordingly, in one embodiment, the invention provides a new method of treatment or prophylaxis of a cardiovascular disease or disorder comprising administering to a patient in need thereof, an effective amount of an inhibitor of phosphodiesterase type 1 (e.g., PDE1 inhibitor, e.g., a PDE1A, PDE1B or PDE1C inhibitor) and an inhibitor of neutral endopeptidase (NEP or Neprilysin), in free or pharmaceutically acceptable salt form.

In one embodiment, the cardiovascular disease or disorder may selected from the group consisting of: atherosclerosis, hypertension, heart failure, congestive heart failure, angina, essential hypertension, pulmonary hypertension, secondary pulmonary hypertension, pulmonary arterial hypertension, isolated systolic hypertension, hypertension associated with diabetes, hypertension associated with atherosclerosis, renovascular hypertension, myocardial infarction and post-myocardial infarction. In certain embodiments, the cardiovascular disease or disorder to be treated may also relate to impaired cGMP/PKG-dependent signaling.

In a further embodiment, the invention also provides a method for the treatment or prophylaxis of cardiovascular disease or disorder that is associated with a muscular dystrophy (e.g, Duchenne, Becker, limb-girdle, myotonic, and Emery-Dreifuss Muscular Dystrophy) comprising administering to a patient in need thereof an effective amount of the compound of a PDE1 inhibitor and an NEP inhibitor as described herein, each in free or pharmaceutically acceptable salt form. As noted above, DMD is caused by the absence of a functional dystrophin protein, which in turn leads to reduced expression and mis-localization of dystrophin-associated proteins; which can include neuronal nitric oxide (NO) synthase. Disruption of nNOS signaling may result in muscle fatigue and unopposed sympathetic vasoconstriction during exercise, thereby increasing contraction-induced damage in dystrophin-deficient muscles. Without being bound by theory, the loss of normal nNOS signaling during exercise may be central to the vascular dysfunction proposed to be an important pathogenic mechanism in DMD. It is contemplated that by inhibiting phosphodiesterase 1 (e.g. PDE1A, PDE1C) and neutral endopeptidase, the invention described herein may circumvent defective nNOS signaling in dystrophic skeletal and/or cardiac muscle; thereby potentially improving cardiac outcomes in DMD patients.

In a further embodiment, the present invention provides for the use of a PDE1 inhibitor in combination with a selective NEP inhibitor, each in free or pharmaceutically acceptable salt form, in the manufacture of a medicament for the treatment or prophylaxis of a cardiovascular disease or disorder. In a further embodiment, the present invention also provides for the use of a PDE1 inhibitor in combination with a selective NEP inhibitor, each in free or pharmaceutically acceptable salt form, for the treatment of a cardiovascular disease or disorder. In a further embodiment, the present invention provides a PDE1 inhibitor in combination with a selective NEP inhibitor for use in the treatment or prophylaxis of a cardiovascular disease or disorder. In a further embodiment, the aforementioned cardiovascular disease or disorder is selected from the group consisting of: atherosclerosis, hypertension, heart failure, congestive heart failure, angina, essential hypertension, pulmonary hypertension, secondary pulmonary hypertension, pulmonary arterial hypertension, isolated systolic hypertension, hypertension associated with diabetes, hypertension associated with atherosclerosis, renovascular hypertension, myocardial infarction and post-myocardial infarction; or is a cardiovascular disease or disorder that is associated with a muscular dystrophy (e.g, Duchenne, Becker, limb-girdle, myotonic, and Emery-Dreifuss Muscular Dystrophy).

In another aspect, the present invention also includes a PDE1 inhibitor of Formula I, II, III, IV, V, VI, VII, VIII, IX, X, or XI described hereinbelow in free or salt form, in combination with a selective NEP inhibitor. In a preferred embodiment, the PDE1 inhibitor is a selective PDE1 inhibitor. In another embodiment, the invention further provides a pharmaceutical composition comprising a PDE1 inhibitor in combination with an NEP inhibitor, each in free or pharmaceutically acceptable salt form, in admixture with a pharmaceutically acceptable carrier.

DETAILED DESCRIPTION OF THE INVENTION

Figure 1:
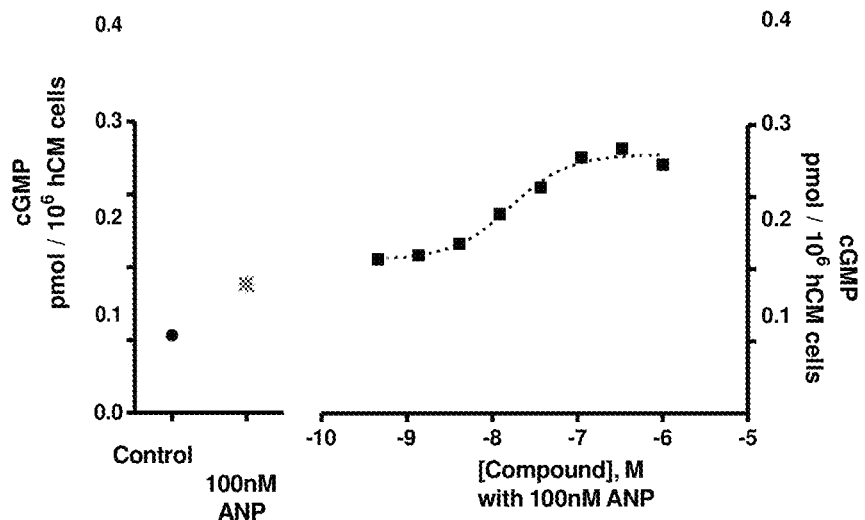
FIG. 1 shows PDE1 inhibition assay results for the compound of Example 20 of U.S. Pat. No. 8,273,750, obtained using the cellular screening assay method described herein with human cardiomyocytes.

Compounds for Use in the Methods of the Invention

In one embodiment, the PDE1 inhibitors for use in the methods of treatment and prophylaxis described herein are selective PDE1 inhibitors.

In another embodiment, the NEP inhibitors for use in the methods of treatment and prophylaxis described herein are selective NEP inhibitors.

PDE1 Inhibitors

In another embodiment, the PDE1 inhibitors are optionally substituted 4,5,7,8-tetrahydro-2H-imidazo[1,2-a]pyrrolo[3,4-e]pyrimidine or 4,5,7,8,9-pentahydro-2H-pyrimido[1,2-a]pyrrolo[3,4-e]pyrimidine, e.g., a Compound of Formula II, e.g., II-A or II-B:

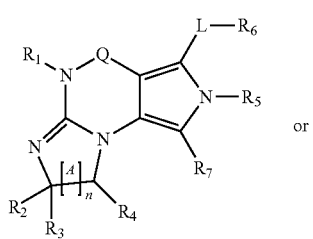

Formula II-A

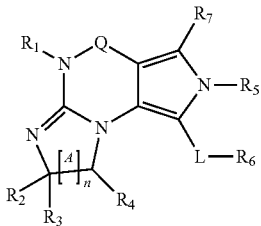

Formula II-B wherein
(i) Q is C(=O), C(=S), C(=N($R_{20}$)) or $CH_2$;
(ii) L is a single bond, —N(H)—, —$CH_2$—, —S—, —S(O)— or —S($O_2$)—;
(iii) $R_1$ is H or $C_{1-4}$ alkyl (e.g., methyl);
(iv) $R_4$ is H or $C_{1-6}$ alkyl (e.g., methyl or isopropyl) and $R_2$ and $R_3$ are, independently,
  H
  $C_{1-6}$alkyl (e.g., methyl, isopropyl) optionally substituted with halo or hydroxy (e.g., $R_2$ and $R_3$ are both methyl, or $R_2$ is H and $R_3$ is methyl, ethyl, isopropyl or hydroxyethyl),
  aryl,
  heteroaryl,
  (optionally hetero)arylalkoxy,
  (optionally hetero)aryl$C_{1-6}$alkyl; or
  $R_2$ and $R_3$ together form a 3- to 6-membered ring;
  or
  $R_2$ is H and $R_3$ and $R_4$ together form a di-, tri- or tetramethylene bridge
  (pref. wherein the $R_3$ and $R_4$ together have the cis configuration, e.g., where the carbons carrying $R_3$ and $R_4$ have the R and S configurations, respectively);
  or
(v) $R_5$ is
  a) —D—E—F, wherein:
    D is $C_{1-4}$alkylene (e.g., methylene, ethylene or prop-2-yn-1-ylene);
    E is a single bond, $C_{2-4}$ alkynylene (e.g., —C≡C—), arylene (e.g., phenylene) or heteroarylene (e.g., pyridylene);
    F is
      H,
      aryl (e.g., phenyl),
      heteroaryl (e.g., pyridyl, diazolyl, triazolyl, for example, pyrid-2-yl, imidazol-1-yl, 1,2,4-triazol-1-yl),
      halo (e.g., F, Br, Cl),
      halo$C_{1-4}$alkyl (e.g., trifluoromethyl),
      —C(O)—$R_{15}$,
      —N($R_{16}$)($R_{17}$), or
      $C_{3-7}$ cycloalkyl optionally containing at least one atom selected from a group consisting of N or O (e.g., cyclopentyl, cyclohexyl, pyrrolidinyl (e.g., pyrrolidin-3-yl), tetrahydro-2H-pyran-4-yl, or morpholinyl);
    wherein D, E and F are independently and optionally substituted with one or more halo (e.g., F, Cl or Br), $C_{1-4}$alkyl (e.g., methyl), halo$C_{1-4}$alkyl (e.g., trifluoromethyl), $C_{1-4}$alkoxy (e.g., methoxy), hydroxy, $C_{1-4}$carboxy, or an additional aryl or heteroaryl (e.g., biphenyl or pyridylphenyl),
    for example, F is heteroaryl, e.g., pyridyl substituted with one or more halo (e.g., 6-fluoropyrid-2-yl, 5-fluoropyrid-2-yl, 6-fluoropyrid-2-yl, 3-fluoropyrid-2-yl, 4-fluoropyrid-2-yl, 4,6-dichloropyrid-2-yl), haloC$_{1-4}$alkyl (e.g., 5-trifluoromethylpyrid-2-yl) or C$_{1-4}$alkyl (e.g., 5-methylpyrid-2-yl), or F is aryl, e.g., phenyl, substituted with one or more halo (e.g., 4-fluorophenyl) or F is a C$_{3-7}$ heterocycloalkyl (e.g., pyrrolidinyl) optionally substituted with a C$_{1-6}$alkyl (e.g., 1-methylpyrrolidin-3-yl); or b) a substituted heteroarylalkyl, e.g., substituted with haloC$_{1-4}$alkyl;

c) attached to the nitrogen on the pyrrolo portion of Formula II-A or II-B and is a moiety of Formula A

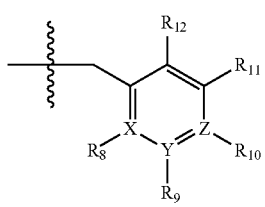

Formula A wherein X, Y and Z are, independently, N or C, and R$_8$, R$_9$, R$_{11}$ and R$_{12}$ are independently H or halogen (e.g., Cl or F), and R$_{10}$ is halogen,
C$_{1-4}$alkyl,
haloC$_{1-4}$alkyl (e.g., triflouromethyl)
C$_{1-4}$alkoxy (e.g. methoxy),
C$_{3-7}$cycloalkyl,
heteroC$_{3-7}$cycloalkyl (e.g., pyrrolidinyl or piperidinyl),
C$_{1-4}$haloalkyl (e.g., trifluoromethyl),
aryl (e.g., phenyl),
heteroaryl (e.g., pyridyl (for example pyrid-2-yl or pyrid-4-yl), or thiadiazolyl (e.g., 1,2,3-thiadiazol-4-yl)), diazolyl (e.g., imidazol-1-yl), triazolyl (e.g., 1,2,4-triazol-1-yl), tetrazolyl,
arylcarbonyl (e.g., benzoyl),
alkylsulfonyl (e.g., methylsulfonyl),
heteroarylcarbonyl, or
alkoxycarbonyl;
wherein the aryl, heteroaryl, cycloalkyl or heterocycloalkyl is independently, optionally substituted with one or more C$_{1-4}$alkyl (e.g., methyl), halogen (e.g., chloro or fluoro), haloC$_{1-4}$alkyl (e.g., trifluoromethyl), hydroxy, C$_{1-4}$ carboxy, —SH or an additional aryl, heteroaryl (e.g., biphenyl or pyridylphenyl) or C$_{3-8}$cycloalkyl,
preferably R$_{10}$ is phenyl, pyridyl, piperidinyl or pyrrolidinyl optionally substituted with the substituents previously defined, e.g. optionally substituted with halo or alkyl
provided that when X, Y, or Z is nitrogen, R$_8$, R$_9$, or R$_{10}$, respectively, is not present;

(vi) R$_6$ is
H,
C$_{1-4}$alkyl (e.g., methyl, ethyl, n-propyl, isobutyl),
C$_{3-7}$cycloalkyl (e.g., cyclopentyl or cyclohexyl),
heteroC$_{3-7}$cycloalkyl (e.g., pyrrolidinyl, piperidinyl, morpholinyl),
aryl (e.g., phenyl),
heteroaryl (e.g., pyrid-4-yl),
arylC$_{1-4}$alkyl (e.g., benzyl),
arylamino (e.g., phenylamino),
heteroarylamino,
N,N-diC$_{1-4}$alkylamino,
N,N-diarylamino,
N-aryl-N-(arylC$_{1-4}$alkyl)amino (e.g., N-phenyl-N-(1,1'-biphen-4-ylmethyl)amino), or
—N(R$_{18}$)(R$_{19}$),
wherein the aryl and heteroaryl are optionally substituted with one or more C$_{1-4}$alkyl (e.g., methyl), halogen (e.g., chloro or fluoro), haloC$_{1-4}$alkyl (e.g., trifluoromethyl), hydroxy, C$_{1-4}$carboxy, or an additional aryl, heteroaryl (e.g., biphenyl or pyridylphenyl) or C$_{3-8}$cycloalkyl;

(vii) R$_7$ is H, C$_{1-6}$alkyl (e.g., methyl or ethyl), halogen (e.g., Cl), —N(R$_{18}$)(R$_{19}$), hydroxy or C$_{1-6}$alkoxy;

(viii) n=0 or 1;

(ix) when n=1, A is —C(R$_{13}$R$_{14}$)—, wherein R$_{13}$ and R$_{14}$, are, independently, H or C$_{1-4}$alkyl, aryl, heteroaryl, (optionally hetero)arylC$_{1-4}$alkoxy, (optionally hetero)arylC$_{1-4}$alkyl or R$_{14}$ can form a bridge with R$_2$ or R$_4$;

(x) R$_{15}$ is C$_{1-4}$alkyl, haloC$_{1-4}$alkyl, —OH or —OC$_{1-4}$alkyl (e.g., —OCH$_3$)

(xi) R$_{16}$ and R$_{17}$ are independently H or C$_{1-4}$alkyl;

(xii) R$_{18}$ and R$_{19}$ are independently
H,
C$_{1-4}$alky (e.g., methyl, ethyl, n-propyl, isobutyl),
C$_{3-8}$cycloalky (e.g., cyclohexyl or cyclopenyl),
heteroC$_{3-8}$cycloalky (e.g., pyrrolidinyl, piperidinyl, morpholinyl),
aryl (e.g., phenyl) or
heteroaryl (e.g., pyridyl),
wherein said aryl and heteroaryl are optionally substituted with one or more
halo (e.g., fluorophenyl, e.g., 4-fluorophenyl),
hydroxy (e.g., hydroxyphenyl, e.g., 4-hydroxyphenyl or 2-hydroxyphenyl),
C$_{1-4}$alkyl (e.g., methyl),
haloC$_{1-4}$alkyl (e.g., trifluoromethyl),
C$_{1-4}$carboxy, or
an additional aryl, heteroaryl (e.g., biphenyl or pyridylphenyl) or C$_{3-8}$cycloalkyl, (xiii) R$_{20}$ is H, C$_{1-4}$alkyl or C$_{3-7}$cycloalkyl;
in free or salt form.

In another embodiment, the PDE1 inhibitors for use in the methods of treatment and prophylaxis described herein are Compound of Formula I, e.g. Formula I-A and I-B:

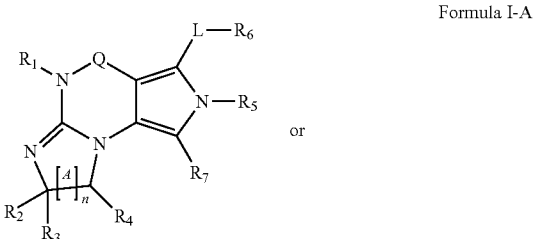

Formula I-A or

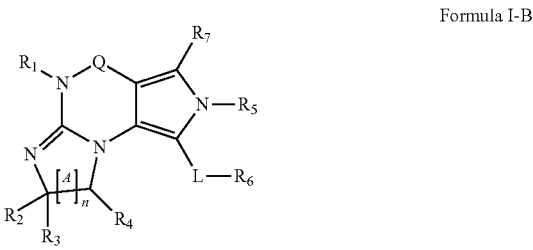

Formula I-B wherein
- (i) Q is C(=O), C(=S), C(=N(R$_{20}$)) or CH$_2$;
- (ii) L is a single bond, —N(H)—, —CH$_2$—, —S—, —S(O)— or —S(O$_2$)—;
- (iii) R$_1$ is H or C$_{1-4}$ alkyl (e.g., methyl);
- (iv) R$_4$ is H or C$_{1-6}$ alkyl (e.g., methyl or isopropyl) and R$_2$ and R$_3$ are, independently,
    H or C$_{1-6}$alkyl (e.g., methyl, isopropyl) optionally substituted with halo or hydroxy (e.g., R$_2$ and R$_3$ are both methyl, or R$_2$ is H and R$_3$ is methyl, ethyl, isopropyl or hydroxyethyl),
    aryl,
    heteroaryl,
    (optionally hetero)arylalkoxy, or
    (optionally hetero)arylC$_{1-6}$alkyl;
    or
    R$_2$ is H and R$_3$ and R$_4$ together form a di-, tri- or tetramethylene bridge (pref. wherein the R$_3$ and R$_4$ together have the cis configuration, e.g., where the carbons carrying R$_3$ and R$_4$ have the R and S configurations, respectively);
- (v) R$_5$ is
    a) —D—E—F, wherein:
        D is C$_{1-4}$alkylene (e.g., methylene, ethylene or prop-2-yn-1-ylene);
        E is a single bond, C$_{2-4}$alkynylene (e.g., —C≡C—), arylene (e.g., phenylene) or heteroarylene (e.g., pyridylene);
        F is
            H,
            aryl (e.g., phenyl),
            heteroaryl (e.g., pyridyl, diazolyl, triazolyl, for example, pyrid-2-yl, imidazol-1-yl, 1,2,4-triazol-1-yl),
            halo (e.g., F, Br, Cl),
            haloC$_{1-4}$alkyl (e.g., trifluoromethyl),
            —C(O)—R$_{15}$,
            —N(R$_{16}$)(R$_{17}$), or
            C$_{3-7}$cycloalkyl optionally containing at least one atom selected from a group consisting of N or O (e.g., cyclopentyl, cyclohexyl, pyrrolidinyl (e.g., pyrrolidin-3-yl), tetrahydro-2H-pyran-4-yl, or morpholinyl);
        wherein D, E and F are independently and optionally substituted with one or more halo (e.g., F, Cl or Br), C$_{1-4}$alkyl (e.g., methyl), haloC$_{1-4}$alkyl (e.g., trifluoromethyl), for example, F is heteroaryl, e.g., pyridyl substituted with one or more halo (e.g., 6-fluoropyrid-2-yl, 5-fluoropyrid-2-yl, 6-fluoropyrid-2-yl, 3-fluoropyrid-2-yl, 4-fluoropyrid-2-yl, 4,6-dichloropyrid-2-yl), haloC$_{1-4}$alkyl (e.g., 5-trifluoromethylpyrid-2-yl) or C$_{1-4}$alkyl (e.g., 5-methylpyrid-2-yl), or F is aryl, e.g., phenyl, substituted with one or more halo (e.g., 4-fluorophenyl) or F is a C$_{3-7}$heterocycloalkyl (e.g., pyrrolidinyl) optionally substituted with a C$_{1-6}$alkyl (e.g., 1-methylpyrrolidin-3-yl); or
    b) a substituted heteroarylalkyl, e.g., substituted with haloalkyl;
    c) attached to the nitrogen on the pyrrolo portion of Formula I-A or I-B and is a moiety of Formula A

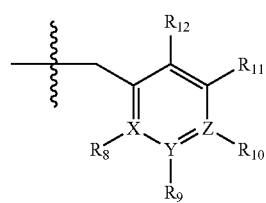

Formula A wherein X, Y and Z are, independently, N or C, and R$_8$, R$_9$, R$_{11}$ and R$_{12}$ are independently H or halogen (e.g., Cl or F), and R$_{10}$ is halogen,
    C$_{1-4}$alkyl,
    C$_{3-7}$cycloalkyl,
    C$_{1-4}$haloalkyl (e.g., trifluoromethyl),
    aryl (e.g., phenyl),
    heteroaryl (e.g., pyridyl (for example pyrid-2-yl), or thiadiazolyl (e.g., 1,2,3-thiadiazol-4-yl)), diazolyl, triazolyl, tetrazolyl,
    arylcarbonyl (e.g., benzoyl),
    alkylsulfonyl (e.g., methylsulfonyl),
    heteroarylcarbonyl, or
    alkoxycarbonyl;
    provided that when X, Y, or Z is nitrogen, R$_8$, R$_9$, or R$_{10}$, respectively, is not present;
- (vi) R$_6$ is
    H,
    C$_{1-4}$alkyl,
    C$_{3-7}$cycloalkyl (e.g., cyclopentyl),
    aryl (e.g., phenyl),
    heteroaryl (e.g., pyrid-4-yl),
    arylC$_{1-4}$alkyl (e.g., benzyl),
    arylamino (e.g., phenylamino),
    heteroarylamino,
    N,N-diC$_{1-4}$alkylamino,
    N,N-diarylamino,
    N-aryl-N-(arylC$_{1-4}$alkyl)amino (e.g., N-phenyl-N-(1,1'-biphen-4-ylmethyl)amino), or
    —N(R$_{18}$)(R$_{19}$);
    wherein the aryl or heteroaryl is optionally substituted with one or more halo (e.g., F, Cl), hydroxy or C$_{1-6}$alkoxy;
- (vii) R$_7$ is H, C$_{1-6}$alkyl, halogen (e.g., Cl), —N(R$_{18}$)(R$_{19}$);
- (viii) n=0 or 1;
- (ix) when n=1, A is —C(R$_{13}$R$_{14}$)—, wherein R$_{13}$ and R$_{14}$ are, independently, H or C$_{1-4}$alkyl, aryl, heteroaryl, (optionally hetero)arylC$_{1-4}$alkoxy or (optionally hetero)arylC$_{1-4}$alkyl;
- (x) R$_{15}$ is C$_{1-4}$alkyl, haloC$_{1-4}$alkyl, —OH or —OC$_{1-4}$alkyl (e.g., —OCH$_3$)
- (xi) R$_{16}$ and R$_{17}$ are independently H or C$_{1-4}$alkyl;
- (xii) R$_{18}$ and R$_{19}$ are independently H, C$_{1-4}$alky or aryl (e.g., phenyl) wherein said aryl is optionally substituted with one or more halo (e.g., fluorophenyl, e.g., 4-fluorophenyl) or hydroxy (e.g., hydroxyphenyl, e.g., 4-hydroxyphenyl or 2-hydroxyphenyl)
- (xiii) R$_{20}$ is H, C$_{1-4}$alkyl or C$_{3-7}$cycloalkyl;
in free or salt form.
1.1 any of the preceding formulae wherein the compounds inhibit phosphodiesterase-mediated (e.g., PDE1-mediated, especially PDE1B-mediated) hydrolysis of cGMP, e.g., with an 1050 of less than 1 μM, preferably less than 750 nM, more preferably less than 500 nM, more preferably less than 50 nM in an immobilized-metal affinity particle reagent PDE assay,
in free or salt form.

The invention further provides optionally substituted 4,5, 7,8-tetrahydro-(optionally 4-thioxo or 4-imino)-(1H or 2H)-imidazo[1,2-a]pyrazolo[4,3-e]pyrimidine or 4,5,7,8,9-pentahydro-(1H or 2H)-pyrimido[1,2-a]pyrazolo[4,3-e]pyrimidine compounds, in free or salt form, e.g., (1 or 2 and/or 3 and/or 5)-substituted 4,5,7,8-tetrahydro-1H-imidazo[1,2-a]pyrazolo[4,3-e]pyrimidine, 4,5,7,8-tetrahydro-2H-imidazo[1,2-a]pyrazolo[4,3-e]pyrimidine, 4,5,7,8-tetrahydro-(1H or 2H)-pyrimido[1,2-a]pyrazolo[4,3-e]pyrimidine-4(5H)-imine, 7,8-dihydro-1H-imidazo[1,2-a]pyrazolo[4,3-e]pyrimidine-4(5H)-thione or 7,8-dihydro-2H-imidazo[1,2-a]pyrazolo[4,3-e]pyrimidine-4(5H)-thione compounds, e.g., a Compound of Formula III:

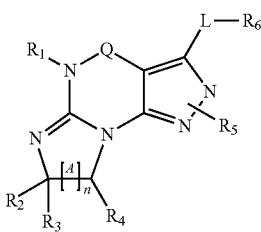

Formula III wherein
(i) Q is C(=S), C(=N($R_{20}$)) or $CH_2$;
(ii) L is a single bond, —N(H)—, —$CH_2$—;
(iii) $R_1$ is H or $C_{1-4}$ alkyl (e.g., methyl or ethyl);
(iv) $R_4$ is H or $C_{1-6}$ alkyl (e.g., methyl, isopropyl) and $R_2$ and $R_3$ are, independently:
  H or $C_{1-6}$alkyl (e.g., methyl or isopropyl) optionally substituted with halo or hydroxy (e.g., $R_2$ and $R_3$ are both methyl, or $R_2$ is H and $R_3$ is methyl, ethyl, isopropyl or hydroxyethyl),
  aryl,
  heteroaryl,
  (optionally hetero)arylalkoxy,
  (optionally hetero)aryl$C_{1-6}$alkyl, or
  $R_2$ and $R_3$ together form a 3- to 6-membered ring;
or
$R_2$ is H and $R_3$ and $R_4$ together form a di-, tri- or tetramethylene bridge (pref. wherein the $R_3$ and $R_4$ together have the cis configuration, e.g., where the carbons carrying $R_3$ and $R_4$ have the R and S configurations, respectively);
(v) $R_5$ is
  d) —D—E—F, wherein:
    D is $C_{1-4}$alkylene (e.g., methylene, ethylene or prop-2-yn-1-ylene);
    E is a single bond, $C_{2-4}$alkynylene (e.g., —C≡C—), arylene (e.g., phenylene) or heteroarylene (e.g., pyridylene);
    F is
      H,
      aryl (e.g., phenyl),
      heteroaryl (e.g., pyridyl, diazolyl, triazolyl, for example, pyrid-2-yl, imidazol-1-yl, 1,2,4-triazol-1-yl),
      halo (e.g., F, Br, Cl),
      halo$C_{1-4}$alkyl (e.g., trifluoromethyl),
      —C(O)—$R_{15}$,
      —N($R_{16}$)($R_{17}$),
      —S(O)$_2R_{21}$ or
      $C_{3-7}$cycloalkyl optionally containing at least one atom selected from a group consisting of N or O (e.g., cyclopentyl, cyclohexyl, pyrrolidinyl (e.g., pyrrolidin-3-yl), tetrahydro-2H-pyran-4-yl, or morpholinyl);
    wherein D, E and F are independently and optionally substituted with one or more:
      halo (e.g., F, Cl or Br),
      $C_{1-4}$alkyl (e.g., methyl),
      halo$C_{1-4}$alkyl (e.g., trifluoromethyl),
      $C_{1-4}$alkoxy) or
      $C_{1-4}$alkyl (e.g., 5-methylpyrid-2-yl),
    for example, F is heteroaryl, e.g., pyridyl substituted with one or more halo (e.g., 6-fluoropyrid-2-yl, 5-fluoropyrid-2-yl, 6-fluoropyrid-2-yl, 3-fluoropyrid-2-yl, 4-fluoropyrid-2-yl, 4,6-dichloropyrid-2-yl),
    or F is aryl, e.g., phenyl, substituted with one or more halo (e.g., 4-fluorophenyl)
    or F is a $C_{3-7}$ heterocycloalkyl (e.g., pyrrolidinyl) optionally substituted with a $C_{1-6}$alkyl (e.g., 1-methylpyrrolidin-3-yl);
  or
  e) a substituted heteroarylalkyl, e.g., substituted with haloalkyl;
  f) attached to one of the nitrogens on the pyrazolo portion of Formula III and is a moiety of Formula A

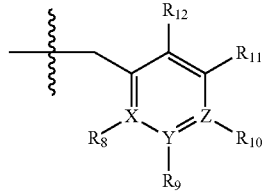

Formula A wherein X, Y and Z are, independently, N or C, and $R_8$, $R_9$, $R_{11}$ and $R_{12}$ are independently H or halogen (e.g., Cl or F), and $R_{10}$ is:
halogen,
  $C_{1-4}$alkyl,
    $C_{3-7}$cycloalkyl,
    het$C_{3-7}$cycloalkyl (e.g., pyrrolidinyl or piperidinyl),
    $C_{1-4}$haloalkyl (e.g., trifluoromethyl),
    aryl (e.g., phenyl),
    heteroaryl (e.g., pyridyl (for example pyrid-2-yl), or thiadiazolyl (e.g., 1,2,3-thiadiazol-4-yl)), diazolyl, triazolyl, tetrazolyl,
    arylcarbonyl (e.g., benzoyl),
    alkylsulfonyl (e.g., methylsulfonyl),
    heteroarylcarbonyl, or
    alkoxycarbonyl;
  wherein the aryl, heteroaryl, cycloalkyl or heterocycloalkyl is independently and optionally substituted with one or more halo (e.g., F or Cl), $C_{1-4}$alkyl, $C_{1-4}$alkoxy, $C_{1-4}$haloalkyl (e.g., trifluoromethyl), —SH;
  preferably $R_{10}$ is phenyl, pyridyl, piperidinyl or pyrrolidinyl optionally substituted with the substituents previously defined, e.g. optionally substituted with halo or alkyl
  provided that when X, Y, or Z is nitrogen, $R_8$, $R_9$, or $R_{10}$, respectively, is not present;

(vi) $R_6$ is
H,
$C_{1-4}$alkyl,
$C_{3-7}$cycloalkyl (e.g., cyclopentyl),
aryl (e.g., phenyl),
heteroaryl (e.g., pyridyl, for example, pyrid-4-yl),
aryl$C_{1-4}$alkyl (e.g., benzyl),
arylamino (e.g., phenylamino),
heterarylamino,
N,N-di$C_{1-4}$alkylamino,
N,N-diarylamino,
N-aryl-N-(aryl$C_{1-4}$alkyl)amino (e.g., N-phenyl-N-(1,1'-biphen-4-ylmethyl)amino), or
—N($R_{18}$)($R_{19}$);
wherein the aryl or heteroaryl is optionally substituted with one or more halo (e.g., F, Cl), hydroxy, $C_{1-6}$alkyl, $C_{1-6}$alkoxy, $C_{3-8}$cycloalkyl, for example, $R_6$ is 4-hydroxyphenyl or 4-fluorophenyl,
(vii) n=0 or 1;
(viii) when n=1, A is —C($R_{13}R_{14}$)—, wherein $R_{13}$ and $R_{14}$, are, independently, H or $C_{1-4}$alkyl, aryl, heteroaryl, (optionally hetero)aryl$C_{1-4}$alkoxy, (optionally hetero)aryl$C_{1-4}$alkyl or $R_{13}$ or $R_{14}$ can form a bridge with $R_2$ or $R_4$;
(ix) $R_{15}$ is $C_{1-4}$alkyl, halo$C_{1-4}$alkyl, —OH or —O$C_{1-4}$alkyl (e.g., —OCH$_3$)
(x) $R_{16}$ and $R_{17}$ are independently H or $C_{1-4}$alkyl;
(xi) $R_{18}$ and $R_{19}$ are independently
H,
$C_{1-4}$alky,
$C_{3-8}$cycloalkyl,
hetero$C_{3-8}$cycloalkyl,
aryl (e.g., phenyl), or
heteroaryl,
wherein said aryl or heteroaryl is optionally substituted with one or more
halo (e.g., fluorophenyl, e.g., 4-fluorophenyl),
hydroxy (e.g., hydroxyphenyl, e.g., 4-hydroxyphenyl or 2-hydroxyphenyl),
$C_{1-6}$alkyl,
halo$C_{1-6}$alkyl,
$C_{1-6}$alkoxy,
aryl,
heteroaryl, or
$C_{3-8}$cycloalkyl;
(xii) $R_{20}$ is H, $C_{1-4}$alkyl (e.g., methyl) or $C_{3-7}$cycloalkyl,
(xiii) $R_{21}$ is $C_{1-6}$alkyl;
in free or salt form.

In yet another embodiment, the invention also provides a Compound of Formula IV:

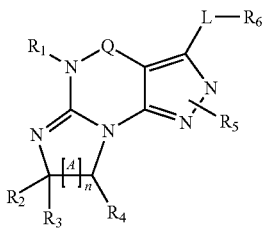

Formula IV wherein
(i) Q is C(=S), C(=N($R_{20}$)) or CH$_2$;
(ii) L is a single bond, —N(H)—, —CH$_2$—;
(iii) $R_1$ is H or $C_{1-4}$ alkyl (e.g., methyl or ethyl);

(iv) $R_4$ is H or $C_{1-6}$ alkyl (e.g., methyl, isopropyl) and $R_2$ and $R_3$ are, independently, H or $C_{1-6}$alkyl (e.g., methyl or isopropyl) optionally substituted with halo or hydroxy (e.g., $R_2$ and $R_3$ are both methyl, or $R_2$ is H and $R_3$ is methyl, ethyl, isopropyl or hydroxyethyl), aryl, heteroaryl, (optionally hetero)arylalkoxy, or (optionally hetero)aryl$C_{1-6}$alkyl; or
$R_2$ is H and $R_3$ and $R_4$ together form a di-, tri- or tetramethylene bridge (pref. wherein the $R_3$ and $R_4$ together have the cis configuration, e.g., where the carbons carrying $R_3$ and $R_4$ have the R and S configurations, respectively);
(v) $R_5$ is
a) —D—E—F, wherein:
D is $C_{1-4}$alkylene (e.g., methylene, ethylene or prop-2-yn-1-ylene);
E is a single bond, $C_{2-4}$alkynylene (e.g., —C≡C—), arylene (e.g., phenylene) or heteroarylene (e.g., pyridylene);
F is H, aryl (e.g., phenyl), heteroaryl (e.g., pyridyl, diazolyl, triazolyl, for example, pyrid-2-yl, imidazol-1-yl, 1,2,4-triazol-1-yl), halo (e.g., F, Br, Cl), halo$C_{1-4}$alkyl (e.g., trifluoromethyl), —C(O)—$R_{15}$, —N($R_{16}$)($R_{17}$), —S(O)$_2R_{21}$ or $C_{3-7}$cycloalkyl optionally containing at least one atom selected from a group consisting of N or O (e.g., cyclopentyl, cyclohexyl, pyrrolidinyl (e.g., pyrrolidin-3-yl), tetrahydro-2H-pyran-4-yl, or morpholinyl);
wherein D, E and F are independently and optionally substituted with one or more:
halo (e.g., F, Cl or Br),
$C_{1-4}$alkyl (e.g., methyl),
halo$C_{1-4}$alkyl (e.g., trifluoromethyl),
for example, F is heteroaryl, e.g., pyridyl substituted with one or more halo (e.g., 6-fluoropyrid-2-yl, 5-fluoropyrid-2-yl, 6-fluoropyrid-2-yl, 3-fluoropyrid-2-yl, 4-fluoropyrid-2-yl, 4,6-dichloropyrid-2-yl), halo$C_{1-4}$alkyl (e.g., 5-trifluoromethylpyrid-2-yl) or $C_{1-4}$alkyl (e.g., 5-methylpyrid-2-yl),
or F is aryl, e.g., phenyl, substituted with one or more halo (e.g., 4-fluorophenyl)
or F is a $C_{3-7}$heterocycloalkyl (e.g., pyrrolidinyl) optionally substituted with a $C_{1-6}$alkyl (e.g., 1-methylpyrrolidin-3-yl);
or
b) a substituted heteroarylalkyl, e.g., substituted with haloalkyl;
c) attached to one of the nitrogens on the pyrazolo portion of Formula IV and is a moiety of Formula A

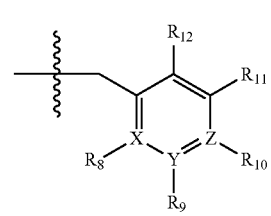

Formula A wherein X, Y and Z are, independently, N or C, and $R_8$, $R_9$, $R_{11}$ and $R_{12}$ are independently H or halogen (e.g., Cl or F), and $R_{10}$ is:

halogen,
C$_{1-4}$alkyl,
C$_{3-7}$cycloalkyl,
C$_{1-4}$haloalkyl (e.g., trifluoromethyl),
aryl (e.g., phenyl),
heteroaryl (e.g., pyridyl (for example pyrid-2-yl), or
thiadiazolyl (e.g., 1,2,3-thiadiazol-4-yl)), diazolyl, triazolyl, tetrazolyl,
arylcarbonyl (e.g., benzoyl),
alkylsulfonyl (e.g., methylsulfonyl),
heteroarylcarbonyl, or
alkoxycarbonyl;
provided that when X, Y, or Z is nitrogen, R$_8$, R$_9$, or R$_{10}$, respectively, is not present;
(vi) R$_6$ is
H,
C$_{1-4}$alkyl,
C$_{3-7}$cycloalkyl (e.g., cyclopentyl),
aryl (e.g., phenyl),
heteroaryl (e.g., pyridyl, for example, pyrid-4-yl),
arylC$_{1-4}$alkyl (e.g., benzyl),
arylamino (e.g., phenylamino),
heterarylamino,
N,N-diC$_{1-4}$alkylamino,
N,N-diarylamino,
N-aryl-N-(arylC$_{1-4}$alkyl)amino (e.g., N-phenyl-N-(1,1'-biphen-4-ylmethyl)amino), or
—N(R$_{18}$)(R$_{19}$);
wherein the aryl or heteroaryl is optionally substituted with one or more halo (e.g., F, Cl), hydroxy or C$_{1-6}$alkoxy, for example, R$_6$ is 4-hydroxyphenyl or 4-fluorophenyl,
(vii) n=0 or 1;
(viii) when n=1, A is —C(R$_{13}$R$_{14}$)—, wherein R$_{13}$ and R$_{14}$, are, independently, H or C$_{1-4}$alkyl, aryl, heteroaryl, (optionally hetero)arylC$_{1-4}$alkoxy or (optionally hetero)arylC$_{1-4}$alkyl;
(ix) R$_{15}$ is C$_{1-4}$alkyl, haloC$_{1-4}$alkyl, —OH or —OC$_{1-4}$alkyl (e.g., —OCH$_3$)
(x) R$_{16}$ and R$_{17}$ are independently H or C$_{1-4}$alkyl;
(xi) R$_{18}$ and R$_{19}$ are independently H, C$_{1-4}$alky or aryl (e.g., phenyl) wherein said aryl is optionally substituted with one or more halo (e.g., fluorophenyl, e.g., 4-fluorophenyl) or hydroxy (e.g., hydroxyphenyl, e.g., 4-hydroxyphenyl or 2-hydroxyphenyl)
(xii) R$_{20}$ is H, C$_{1-4}$alkyl (e.g., methyl) or C$_{3-7}$cycloalkyl,
(xiii) R$_{21}$ is C$_{1-6}$alkyl;
in free or salt form.

In still yet another embodiment, the invention provides that the PDE1 inhibitors for use in the methods of treatment and prophylaxis which are described herein are selected from any of the following: US 2008-0188492 A1, US 2010-0173878 A1, US 2010-0273754 A1, US 2010-0273753 A1, WO 2010/065153, WO 2010/065151, WO 2010/065151, WO 2010/065149, WO 2010/065147, WO 2010/065152, WO 2011/153129, WO 2011/133224, WO 2011/153135, WO 2011/153136, and WO 2011/153138, the contents of each of which are incorporated herein by reference in their entireties.

In yet another embodiment the invention provides that the PDE1 inhibitors for use in the methods of treatment and prophylaxis described herein are compounds of Formula V:

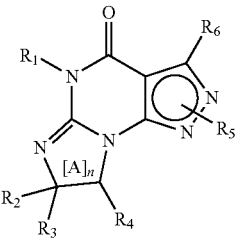

Formula V wherein
(i) R$_1$ is H or C$_{1-4}$ alkyl (e.g., methyl);
(ii) R$_4$ is H or C$_{1-4}$ alkyl and R$_2$ and R$_3$ are, independently, H or C$_{1-4}$ alkyl (e.g., R$_2$ and R$_3$ are both methyl, or R$_2$ is H and R$_3$ is isopropyl), aryl, heteroaryl, (optionally hetero)arylalkoxy, or (optionally hetero)arylalkyl;
or
R$_2$ is H and R$_3$ and R$_4$ together form a di-, tri- or tetramethylene bridge (pref. wherein the R$_3$ and R$_4$ together have the cis configuration, e.g., where the carbons carrying R$_3$ and R$_4$ have the R and S configurations, respectively);
(iii) R$_5$ is a substituted heteroarylalkyl, e.g., substituted with haloalkyl or
R$_5$ is attached to one of the nitrogens on the pyrazolo portion of Formula V and is a moiety of Formula A

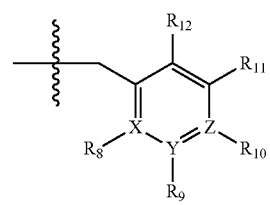

Formula A wherein X, Y and Z are, independently, N or C, and R$_8$, R$_9$, R$_{11}$ and R$_{12}$ are independently H or halogen (e.g., Cl or F), and R$_{10}$ is halogen, alkyl, cycloalkyl, haloalkyl (e.g., trifluoromethyl), aryl (e.g., phenyl), heteroaryl (e.g., pyridyl (for example pyrid-2-yl), or thiadiazolyl (e.g., 1,2,3-thiadiazol-4-yl)), diazolyl, triazolyl, tetrazolyl, arylcarbonyl (e.g., benzoyl), alkylsulfonyl (e.g., methylsulfonyl), heteroarylcarbonyl, or alkoxycarbonyl; provided that when X, Y, or Z is nitrogen, R$_8$, R$_9$, or R$_{10}$, respectively, is not present; and
(iv) R$_6$ is H, alkyl, aryl, heteroaryl, arylalkyl (e.g., benzyl), arylamino (e.g., phenylamino), heterarylamino, N,N-dialkylamino, N,N-diarylamino, or N-aryl-N-(arylakyl)amino (e.g., N-phenyl-N-(1,1'-biphen-4-ylmethyl)amino); and
(v) n=0 or 1;
(vi) when n=1, A is —C(R$_{13}$R$_{14}$)—
wherein R$_{13}$ and R$_{14}$, are, independently, H or C$_{1-4}$ alkyl, aryl, heteroaryl, (optionally hetero)arylalkoxy or (optionally hetero)arylalkyl;
in free, salt or prodrug form, including its enantiomers, diastereoisomers and racemates.

In one embodiment the invention provides that the PDE1 inhibitors for use in the methods of treatment and prophylaxis described herein are compounds of Formula VI:

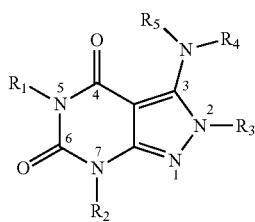

Formula VI wherein:
(i) R₁ is H or alkyl;
(ii) R₂ is H, alkyl, cycloalkyl, haloalkyl, alkylaminoalkyl, hydroxyalkyl, arylalkyl, heteroarylalkyl, or alkoxyarylalkyl;
(iii) R₃ is heteroarylmethyl or formula A

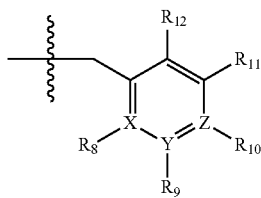

Formula A wherein X, Y and Z are, independently, N or C, and R₈, R₉, R₁₁ and R₁₂ are independently H or halogen; and R₁₀ is halogen, alkyl, cycloalkyl, haloalkyl, aryl, heteroaryl, alkyl sulfonyl, arylcarbonyl, heteroarylcarbonyl, alkoxycarbonyl, or aminocarbonyl;
(iv) R₄ is aryl or heteroaryl; and
(v) R₅ is H, alkyl, cycloalkyl, heteroaryl, aryl, p-benzylaryl;
provided that when X, Y or X is nitrogen, R₈, R₉ or R₁₀, respectively, is not present; wherein "alk" or "alkyl" refers to $C_{1-6}$ alkyl and "cycloalkyl" refers to $C_{3-6}$ cycloalkyl, in free, salt or physiologically hydrolysable and acceptable ester prodrug form.

In one embodiment the invention provides that the PDE1 inhibitors for use in the methods of treatment and prophylaxis described herein are compounds of Formula VII:

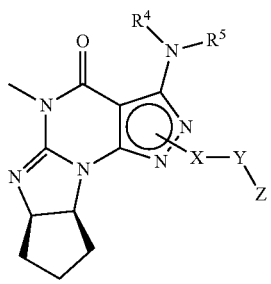

Formula VII (i) X is $C_{1-6}$alkylene (e.g., methylene, ethylene or prop-2-yn-1-ylene);
(ii) Y is a single bond, alkynylene (e.g., —C≡C—), arylene (e.g., phenylene) or heteroarylene (e.g., pyridylene);
(iii) Z is H, aryl (e.g., phenyl), heteroaryl (e.g., pyridyl, e.g., pyrid-2-yl), halo (e.g., F, Br, Cl), halo$C_{1-6}$alkyl (e.g., trifluoromethyl), —C(O)—R¹, —N(R²)(R³), or $C_{3-7}$cycloalkyl optionally containing at least one atom selected from a group consisting of N or O (e.g., cyclopentyl, cyclohexyl, tetrahydro-2H-pyran-4-yl, or morpholinyl);
(iv) R¹ is $C_{1-6}$alkyl, halo$C_{1-6}$alkyl, —OH or —O$C_{1-6}$alkyl (e.g., —OCH₃);
(v) R² and R³ are independently H or $C_{1-6}$alkyl;
(vi) R⁴ and R⁵ are independently H, $C_{1-6}$alky or aryl (e.g., phenyl) optionally substituted with one or more halo (e.g., fluorophenyl, e.g., 4-fluorophenyl), hydroxy (e.g., hydroxyphenyl, e.g., 4-hydroxyphenyl or 2-hydroxyphenyl) or $C_{1-6}$alkoxy;
(vii) wherein X, Y and Z are independently and optionally substituted with one or more halo (e.g., F, Cl or Br), $C_{1-6}$alkyl (e.g., methyl), halo$C_{1-6}$alkyl (e.g., trifluoromethyl), for example, Z is heteroaryl, e.g., pyridyl substituted with one or more halo (e.g., 6-fluoropyrid-2-yl, 5-fluoropyrid-2-yl, 6-fluoropyrid-2-yl, 3-fluoropyrid-2-yl, 4-fluoropyrid-2-yl, 4,6-dichloropyrid-2-yl), halo$C_{1-6}$-alkyl (e.g., 5-trifluoromethylpyrid-2-yl) or $C_{1-6}$-alkyl (e.g., 5-methylpyrid-2-yl), or Z is aryl, e.g., phenyl, substituted with one or more halo (e.g., 4-fluorophenyl),
in free, salt or prodrug form.

In further embodiment, the invention provides that the PDE1 inhibitor of Formula VII is:

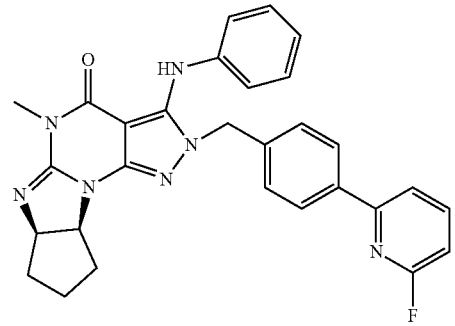 [SMILES: CN1C(=O)c2c(nn(Cc3ccc(-c4cccc(F)n4)cc3)c2Nc2ccccc2)N2C1=N[C@@H]1CCC[C@@H]12]

in free, salt (e.g., pharmaceutically acceptable salt) or prodrug form.

In one embodiment, the invention provides that the PDE1 inhibitors for use in the methods of treatment and prophylaxis described herein are compounds of Formula VIII:

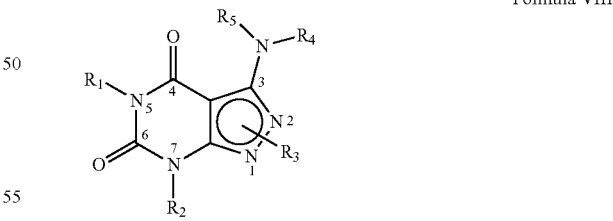

Formula VIII wherein
(i) R₁ is H or $C_{1-6}$alkyl;
(ii) R₂ is
H,
$C_{1-6}$alkyl,
$C_{3-8}$cycloalkyl optionally substituted with one or more amino,
$C_{3-8}$heterocycloalkyl optionally substituted with $C_{1-6}$alkyl,
$C_{3-8}$cycloalkyl-$C_{1-6}$alkyl, $C_{1-6}$haloalkyl,
$C_{0-6}$alkylamino$C_{0-6}$alkyl,
hydroxy$C_{1-6}$alkyl,
aryl$C_{0-6}$alkyl,
heteroarylalkyl,
$C_{1-6}$alkoxyaryl$C_{1-6}$alkyl, or
—G—J wherein:
  G is a single bond or, alkylene;
  J is cycloalkyl or heterocycloalkyl optionally substituted with alkyl;
(iii) $R_3$ is
a) —D—E—F wherein
  1. D is single bond, $C_{1-6}$alkylene or aryl$C_{1-6}$alkylene;
  2. E is a $C_{1-6}$alkylene, arylene, $C_{1-6}$alkylarylene, amino$C_{1-6}$alkylene- or amino; and
  3. F is hetero$C_{3-8}$cycloalkyl optionally substituted with $C_{1-6}$alkyl;
(iv) $R_4$ is aryl optionally substituted with one or more halo, hydroxy or $C_{1-6}$alkoxy; heteroaryl; or hetero$C_{3-6}$cycloalkyl; and
(v) $R_5$ is H, $C_{1-6}$alkyl, $C_{3-8}$cycloalkyl, heteroaryl, aryl or p-benzylaryl;
wherein "alk", "alkyl", "haloalkyl" or "alkoxy" refers to $C_{1-6}$alkyl and "cycloalkyl" refers to $C_{3-8}$cycloalkyl;
in free or salt form.

In another embodiment the invention provides that the PDE1 inhibitors for use in the methods of treatment and prophylaxis described herein are compounds of Formula IX:

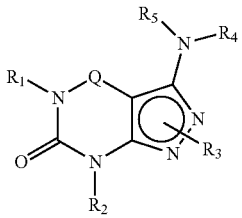

Formula IX wherein
(i) Q is —C(=S)—, —C(=N($R_6$))— or —C($R_{14}$)($R_{15}$)—;
(ii) $R_1$ is H or $C_{1-6}$alkyl (e.g., methyl or ethyl);
(iii) $R_2$ is
H,
$C_{1-6}$alkyl (e.g., isopropyl, isobutyl, 2-methylbutyl or 2,2-dimethylpropyl) wherein said alkyl group is optionally substituted with one or more halo (e.g., fluoro) or hydroxy (e.g., hydroxy$C_{1-6}$alkyl, for example 1-hydroxyprop-2-yl or 3-hydroxy-2-methylpropyl),
halo$C_{1-6}$alkyl (e.g., trifluoromethyl or 2,2,2-trifluoroethyl),
N($R_{14}$)($R_{15}$)—$C_{1-6}$alkyl (e.g., 2-(dimethylamino)ethyl or 2-aminopropyl),
aryl$C_{0-6}$alkyl (e.g., phenyl or benzyl), wherein said aryl is optionally substituted with one or more $C_{1-6}$alkoxy, for example, $C_{1-6}$alkoxyaryl$C_{0-6}$alkyl (e.g., 4-methoxybenzyl),
heteroaryl$C_{0-6}$alkyl (e.g., pyridinylmethyl), wherein said heteroaryl is optionally substituted with one or more $C_{1-6}$alkoxy (e.g., $C_{1-6}$alkoxyheteroaryl$C_{1-6}$alkyl);
—G—J wherein G is a single bond or $C_{1-6}$alkylene (e.g., methylene) and J is $C_{3-8}$cycloalkyl or hetero$C_{3-8}$cycloalkyl (e.g., oxetan-2-yl, pyrrolidin-3-yl, pyrrolidin-2-yl) wherein the cycloalkyl and heterocycloalkyl group are optionally substituted with one or more $C_{1-6}$ alkyl or amino, for example,
—$C_{0-4}$alkyl-$C_{3-8}$cycloalkyl (e.g., —$C_{0-4}$alkyl-cyclopentyl, —$C_{0-4}$alkyl-cyclohexyl or —$C_{0-4}$alkyl-cyclopropyl), wherein said cycloalkyl is optionally substituted with one or more $C_{1-6}$ alkyl or amino (for example, 2-aminocyclopentyl or 2-aminocyclohexyl),
—$C_{0-4}$alkyl-$C_{3-8}$heterocycloalkyl (e.g., —$C_{0-4}$alkyl-pyrrolidinyl, for example, —$C_{0-4}$alkylpyrrolidin-3-yl) wherein said heterocycloalkyl is optionally substituted with $C_{1-6}$alkyl (e.g., methyl), for example, 1-methylpyrrolidin-3-yl, 1-methyl-pyrrolindin-2-yl, 1-methyl-pyrrolindin-2-yl-methyl or 1-methyl-pyrrolindin-3-yl-methyl);
(iv) $R_3$ is
1) —D—E—F wherein:
D is a single bond, $C_{1-6}$alkylene (e.g., methylene), or aryl$C_{1-6}$alkylene (e.g., benzylene or —$CH_2C_6H_4$—);
E is
  a single bond,
  $C_{1-4}$alkylene (e.g., methylene, ethynylene, prop-2-yn-1-ylene),
  $C_{0-4}$alkylarylene (e.g., phenylene or —$C_6H_4$—, -benzylene- or —$CH_2C_6H_4$—), wherein the arylene group is optionally substituted with halo (e.g., Cl or F),
  heteroarylene (e.g., pyridinylene or pyrimidinylene),
  amino$C_{1-6}$alkylene (e.g., —$CH_2N(H)$—),
  amino (e.g., —N(H)—);
  $C_{3-8}$cycloalkylene optionally containing one or more heteroatom selected from N or O (e.g., piperidinylene),
F is
  H,
  halo (e.g., F, Br, Cl),
  $C_{1-6}$alkyl (e.g., isopropyl or isobutyl),
  halo$C_{1-6}$alkyl (e.g., trifluoromethyl),
  aryl (e.g., phenyl),
  $C_{3-8}$cycloalkyl optionally containing one or more atom selected from a group consisting of N, S or O (e.g., cyclopentyl, cyclohexyl, piperidinyl, pyrrolidinyl, tetrahydro-2H-pyran-4-yl, or morpholinyl), and optionally substituted with one or more $C_{1-6}$alkyl (e.g., methyl or isopropyl), for example, 1-methylpyrrolidin-2-yl, pyrrolidin-1-yl, pyrrolidin-2-yl, piperidin-2-yl, 1-methylpiperidin-2-yl, 1-ethylpiperidin-2-yl,
  heteroaryl (e.g., pyridyl (for example, pyrid-2-yl), pyrimidinyl (for example, pyrimidin-2-yl), thiadiazolyl (for example, 1,2,3-thiadiazol-4-yl), diazolyl (e.g., pyrazolyl (for example, pyrazol-1-yl) or imidazolyl (for example, imidazol-1-yl, 4-methylimidazolyl, 1-methylimidazol-2-yl)), triazolyl (e.g., 1,2,4-triazol-1-yl), tetrazolyl (e.g., tetrazol-5-yl), alkyloxadiazolyl (e.g., 5-methyl-1,2,4-oxadiazol), wherein said heteroaryl is optionally substituted with one or more $C_{1-6}$alkyl, halo (e.g., fluoro) or halo$C_{1-6}$alkyl;

$C_{1-6}$alkoxy,

—O-halo$C_{1-6}$ alkyl (e.g., —O—CF$_3$), $C_{1-6}$alkylsulfonyl (for example, methylsulfonyl or —S(O)$_2$CH$_3$), —C(O)—R$_{13}$, wherein R$_{13}$ is —N(R$_{14}$)(R$_{15}$), $C_{1-6}$alkyl (e.g., methyl), —OC$_{1-6}$alkyl (e.g., —OCH$_3$), halo$C_{1-6}$alkyl (trifluoromethyl), aryl (e.g., phenyl), or heteroaryl;

—N(R$_{14}$)(R$_{15}$);

or 2) a substituted heteroaryl$C_{1-6}$aklyl, e.g., substituted with halo$C_{1-6}$alkyl;

or 3) attached to one of the nitrogens on the pyrazolo portion of Formula I and is a moiety of Formula A

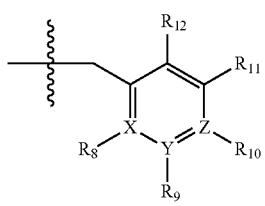

Formula A wherein:

X, Y and Z are, independently, N or C,

R$_8$, R$_9$, R$_{11}$ and R$_{12}$ are independently H or halogen (e.g., Cl or F); and R$_{10}$ is halogen (e.g., fluoro or chloro), $C_{1-6}$alkyl, $C_{3-8}$cycloalkyl, hetero$C_{3-8}$cycloalkyl (e.g., pyrrolidinyl or piperidinyl), halo$C_{1-6}$alkyl (e.g., trifluoromethyl), aryl (e.g., phenyl) or heteroaryl (e.g., pyridyl, (for example, pyrid-2-yl) or e.g., thiadiazolyl (for example, 1,2,3-thiadiazol-4-yl), diazolyl, triazolyl (e.g., 1,2,4-triazol-1-yl), tetrazolyl (e.g., tetrazol-5-yl), alkyloxadiazolyl (e.g., 5-methyl-1,2,4-oxadiazol), pyrazolyl (e.g., pyrazol-1-yl), wherein said aryl, heteroaryl, cycloalkyl or heterocycloalkyl is optionally substituted with one or more $C_{1-6}$alkyl (e.g., methyl), halogen (e.g., chloro or fluoro), halo$C_{1-6}$alkyl (e.g., trifluoromethyl), hydroxy, carboxy, —SH, or an additional aryl or heteroaryl (e.g., biphenyl or pyridylphenyl), $C_{1-6}$alkyl sulfonyl (e.g., methyl sulfonyl), arylcarbonyl (e.g., benzoyl), heteroarylcarbonyl, $C_{1-6}$alkoxycarbonyl, (e.g., methoxycarbonyl), Aminocarbonyl,

—N(R$_{14}$)(R$_{15}$);

preferably R$_{10}$ is phenyl, pyridyl, piperidinyl or pyrrolidinyl optionally substituted with the substituents previously defined, e.g. optionally substituted with halo or alkyl;

provided that when X, Y or X is nitrogen, R$_8$, R$_9$ or R$_{10}$, respectively, is not present;

(v) R$_4$ and R$_5$ are independently:

H, $C_{1-6}$alkyl (e.g., methyl, isopropyl, isobutyl, n-propyl), $C_{3-8}$cycloalkyl (e.g., cyclopentyl or cyclohexyl), $C_{3-8}$heterocycloalkyl (e.g., pyrrolidinyl (for example pyrrolidin-3-yl or pyrrolidin-1-yl), piperidinyl (for example, piperidin-1-yl), morpholinyl), —$C_{0-6}$alkylaryl (e.g., phenyl or benzyl) or —$C_{0-6}$alkylheteroaryl (e.g., pyrid-4-yl, pyrid-2-yl or pyrazol-3-yl)

wherein said aryl or heteroaryl is optionally substituted with one or more halo (e.g., 4-fluorophenyl), hydroxy (e.g., 4-hydroxyphenyl), $C_{1-6}$alkyl, $C_{1-6}$alkoxy or another aryl group (e.g., biphenyl-4-ylmethyl);

(vi) R$_6$ is H, $C_{1-6}$alkyl (e.g., methyl or ethyl) or $C_{3-8}$cycloalkyl; (vii) R$_{14}$ and R$_{15}$ are independently H or $C_{1-6}$alkyl, in free or salt form.

In still another embodiment, the invention provides that the PDE1 inhibitors for use in the methods of treatment and prophylaxis described herein are Formula X, e.g.:

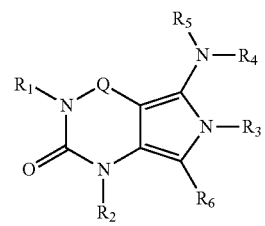

Formula X-A

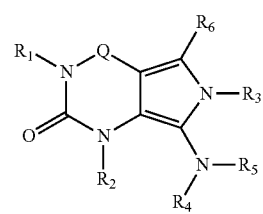

Formula X-B wherein (i) Q is —C(=S)—, —C(=O)—, —C(=N(R$_7$))— or —C(R$_{14}$)(R$_{15}$)—;

(ii) R$_1$ is H or $C_{1-6}$alkyl (e.g., methyl or ethyl);

(iii) R$_2$ is H, $C_{1-6}$alkyl (e.g., isopropyl, isobutyl, 2-methylbutyl, 2,2-dimethylpropyl) wherein said alkyl group is optionally substituted with halo (e.g., fluoro) or hydroxy (e.g., 1-hydroxypropan-2-yl, 3-hydroxy-2-methylpropyl), for example, R$_2$ may be a trifluoromethyl or 2,2,2-trifluoroethyl, N(R$_{14}$)(R$_{15}$)— $C_{1-6}$ alkyl (e.g., 2-(dimethylamino)ethyl or 2-aminopropyl), aryl$C_{1-6}$ alkyl (e.g., phenyl or benzyl), heteroaryl $C_{1-6}$alkyl (e.g., pyridinylmethyl), $C_{1-6}$alkoxyaryl-$C_{1-6}$ alkyl (e.g., 4-methoxybenzyl); —G—J wherein:

G is a single bond or, alkylene (e.g., methylene); J is cycloalkyl or heterocycloalkyl (e.g., oxetan-2-yl, pyrolyin-3-yl, pyrolyin-2-yl) optionally substituted with one or more $C_{1-6}$alkyl (e.g., (1-methylpyrolidin-2-yl)), amino (e.g., —NH$_2$), for example, —G—J may be —$C_{0-4}$alkyl-$C_{3-8}$cycloalkyl (e.g., cyclopentyl, cyclohexyl or cyclopropylmethyl) optionally substituted with one or more $C_{1-6}$alkyl, amino (e.g., —NH$_2$), for example, 2-aminocyclopentyl or 2-aminocyclohexyl, wherein said cycloalkyl optionally contains one or more heteroatom selected from N and O (e.g., pyrrolidinyl, for example, pyrrolidin-3-yl or pyrrolidin-2-yl, 1-methyl-pyrrolindin-2-yl, 1-methyl-pyrrolindin-3-yl, 1-methyl-pyrrolindin-2-yl-methyl or 1-methyl-pyrrolindin-3-yl-methyl);

(iv) $R_3$ is
1) —D—E—F wherein:
D is a single bond, $C_{1-6}$alkylene (e.g., methylene), or arylalkylene
(e.g., p-benzylene or —$CH_2C_6H_4$—);
E is a single bond,
$C_{1-6}$alkylene (e.g., methylene) $C_{2-6}$ alkynylene (e.g., ethynylene, prop-2-yn-1-ylene),ethynylene, prop-2-yn-1-ylene), —$Co_{-4}$alkylarylene (e.g., phenylene or —$C_6H_4$—, -benzylene- or —$CH_2C_6H_4$—), wherein the arylene group is optionally substituted with halo (e.g., Cl or F), heteroarylene
(e.g., pyridinylene or pyrimidinylene), amino$Ci_{-6}$alkylene (e.g., —$CH_2N(H)$—), amino (e.g., —N(H)—);
$C_{3-8}$cycloalkylene optionally containing one or more heteroatom selected from N or O (e.g., piperidinylene),
F is
H,
halo (e.g., F, Br, Cl), $C_{1-6}$alkyl (e.g., isopropyl or isobutyl), halo$C_{1-6}$alkyl (e.g., trifluoromethyl),
aryl (e.g., phenyl),
$C_{3-8}$cycloalkyl optionally containing at least one atom selected from a group consisting of N or O (e.g., cyclopentyl, N cyclohexyl, piperidinyl, pyrrolidinyl, tetrahydro-2H-pyran-4-yl, or morpholinyl), said cycloalkyl is optionally substituted with $C_{1-6}$alkyl (e.g., methyl or isopropyl), for example, 1-methyl-pyrrolidin-2-yl, pyrrolidin-1-yl, pyrrolidin-2-yl, piperidin-2-yl, 1-methyrpiperidin-2-yl, 1-ethylpiperidin-2-yl, heteroaryl optionally substituted with $C_{1-6}$alkyl, (e.g., pyridyl, (for example, pyrid-2-yl), pyrimidinyl (for example, pyrimidin-2-yl), thiadiazolyl (for example, 1,2,3-thiadiazol-4-yl), diazolyl (e.g., pyrazolyl (for example, pyrazol-1-yl) or imidazolyl (for example, imidazol-1-yl, 4-methylimidazolyl, 1-methylimidazol-2-yl,), triazolyl (e.g., 1,2,4-triazol-1-yl), tetrazolyl (e.g., tetrazol-5-yl), alkoxadiazolyl (e.g., 5-methyl-1,2,4-oxadiazol), pyrazolyl (e.g., pyrazol-1-yl), wherein said heteroaryl is optionally substituted with halo (e.g., fluoro) or halo$C_{1-6}$alkyl, for example, 6-fluoropyrid-2-yl; amino (e.g., —$NH_2$), $C_{1-6}$alkoxy, —O-halo$C_{1-6}$alkyl (e.g., -0-$CF_3$), $C_{1-6}$alkylsulfonyl (for example, methylsulfonyl or —$S(O)_2CH_3$),
—$C(O)$—$R_{13}$,
—$N(R_{14})(R_{15})$; or
2) a substituted heteroarylaklyl, e.g., substituted with haloalkyl; or
3) attached to the nitrogen on the pyrrolo portion of Formula I and is a moiety of Formula A

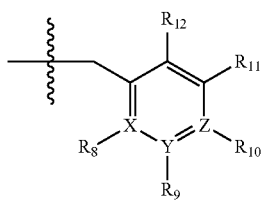

Formula A wherein X, Y and Z are, independently, N or C, and $R_8$, $R_9$, $R_{11}$ and $R_{12}$ are independently H or halogen (e.g., Cl or F); and $R_{10}$ is halogen, $C_{1-6}$alkyl,
$C_{1-6}$alkoxy (e.g., methoxy), $C_{3-8}$cycloalkyl, hetero$C_{3-8}$cycloalkyl (e.g., pyrrolidinyl) halo$C_{1-6}$alkyl (e.g., trifluoromethyl), aryl (e.g., phenyl), heteroaryl (e.g., pyridyl, (for example, pyrid-2-yl) or e.g., thiadiazolyl (for example, 1,2,3-thiadiazol-4-yl), diazolyl (e.g., imidazolyl or pyrazolyl), triazolyl (e.g., 1,2,4-triazol-1-yl), tetrazolyl (e.g., tetrazol-5-yl), alkoxadiazolyl (e.g., 5-methyl-1,2,4-oxadiazol), pyrazolyl (e.g., pyrazol-1-yl), $C_{1-6}$alkyl sulfonyl (e.g., methyl sulfonyl), arylcarbonyl (e.g., benzoyl), heteroarylcarbonyl, alkoxycarbonyl, (e.g., methoxycarbonyl), aminocarbonyl; wherein the aryl, heteroaryl, cycloalkyl or heterocycloalkyl is optionally substituted with one or more $C_{1-6}$alkyl (e.g., methyl), halogen (e.g., chloro or fluoro), halo$C_{1-6}$alkyl (e.g., trifluoromethyl), hydroxy, carboxy, —SH, or an additional aryl or heteroaryl (e.g., biphenyl or pyridylphenyl) preferably $R_{10}$ is phenyl or pyridyl, e.g., 2-pyridyl optionally substituted with the substituents previously defined;
provided that when X, Y or X is nitrogen, $R_8$, $R_9$ or $R_{10}$, respectively, is not present; (v) $R_4$ and $R_5$ are independently H, $C_{1-6}$alkyl (e.g., methyl, isopropyl),
$C_{3-8}$cycloalkyl (e.g., cyclopentyl), $C_{3-8}$heterocycloalkyl (e.g., pyrrolidin-3-yl), aryl (e.g., phenyl) or heteroaryl (e.g., pyrid-4-yl, pyrid-2-yl or pyrazol-3-yl) wherein said aryl or heteroaryl is optionally substituted with halo (e.g., 4-fluorophenyl), hydroxy (e.g., 4-hydroxyphenyl), $C_{1-6}$alkyl, $C_{1-6}$alkoxy or another aryl group (e.g., biphenyl-4-ylmethyl);
(vi) $R_6$ is H, $C_{1-6}$alkyl (e.g., methyl), hydroxy, $C_{1-6}$alkoxy, aryloxy, —$N(R_{16})(R_{17})$, oxo (e.g., =O), or $C_{3-8}$Cycloalkyl;
(vii) $R_7$ is H, $C_{1-6}$alkyl (e.g., methyl) or $C_{3-8}$cycloalkyl wherein said cycloalkyl is optionally substituted with one or more oxo (e.g., 2,5-dioxopyrrolidin-1-yl);
(viii) $R_{13}$ is —$N(R_{14})(R_{15})$, $C_{1-6}$alkyl (e.g., methyl), —$OC_{1-6}$alkyl (e.g., —$OCH_3$), halo$C_{1-6}$alkyl (trifluoromethyl), aryl (e.g., phenyl), or heteroaryl; and
(ix) $R_{14}$ and $R_{15}$ are independently H or $C_{1-6}$alkyl;
(x) Rib and Rig are independently H, $C_{1-6}$alkyl, aryl (e.g., phenyl), heteroaryl, wherein said aryl or heteroaryl is optionally substituted with halo (e.g., fluoro), $C_{1-6}$alkoxy (e.g., methoxy); in free or salt form.

In one embodiment the invention provides that the PDE1 inhibitors for use in the methods of treatment and prophylaxis described herein are Formula XI:

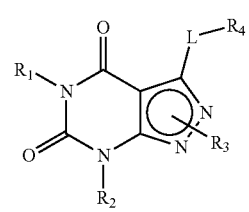

Formula XI wherein
(i) L is S, SO or $SO_2$;
(ii) $R_2$ is H or $C_{1-6}$alkyl (e.g., methyl or ethyl);
(iii) $R_2$ is
H,
$C_{1-6}$alkyl (e.g., isopropyl, isobutyl, neopentyl, 2-methylbutyl, 2,2-dimethylpropyl) wherein said alkyl group is optionally substituted with halo (e.g., fluoro) or hydroxy (e.g., 1-hydroxypropan-2-yl, 3-hydroxy-2- methylpropyl), —C$_{0-4}$alkyl-C$_{3-8}$cycloalkyl (e.g., cyclopentyl, cyclohexyl) optionally substituted with one or more amino (e.g., —NH$_2$), for example, 2-aminocyclopentyl or 2-aminocyclohexyl), wherein said cycloalkyl optionally contains one or more heteroatom selected from N and O and is optionally substituted with C$_{1-6}$alkyl (e.g., 1-methyl-pyrrolindin-2-yl, 1-methyl-pyrrolindin-3-yl, 1-methyl-pyrrolindin-2-yl-methyl or 1-methyl-pyrrolindin-3-yl-methyl), C$_{3-8}$heterocycloalkyl (e.g., pyrrolidinyl, for example, pyrrolidin-3-yl) optionally substituted with C$_{1-6}$alkyl (e.g., methyl), for example, 1-methylpyrrolidin-3-yl, C$_{3-8}$cycloalkyl-C$_{1-6}$ alkyl (e.g., cyclopropylmethyl), haloC$_{1-6}$ alkyl (e.g., trifluoromethyl, 2,2,2-trifluoroethyl), —N(R$_{14}$)(R$_{15}$)—C$_{1-6}$alkyl (e.g., 2-(dimethylamino) ethyl,2-aminopropyl), hydroxyC$_{1-6}$alkyl (e.g., (e.g., 3-hydroxy-2-methylpropyl, 1-hydroxyprop-2-yl), arylC$_{0-6}$alkyl (e.g., benzyl), heteroarylC$_{1-6}$alkyl (e.g., pyridinylmethyl), C$_{1-6}$alkoxyarylC$_{1-6}$alkyl (e.g., 4-methoxybenzyl); —G—J wherein: G is a single bond or, alkylene (e.g., methylene);

J is cycloalkyl or heterocycloalkyl (e.g., oxetan-2-yl, pyrolyin-3-yl, pyrolyin-2-yl) optionally substituted with C$_{1-6}$alkyl (e.g., (1-methylpyrolidin-2-yl));

(iv) R$_3$ is attached to one of the nitrogens on the pyrazolo portion of Formula I and is a moiety of Formula A

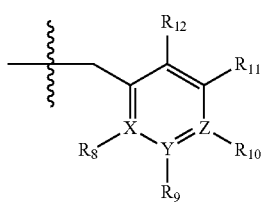

Formula A wherein X, Y and Z are, independently, N or C, and R$_8$, R$_9$, R$_{11}$ and R$_{12}$ are independently H or halogen (e.g., Cl or F); and R$_{10}$ is halogen, C$_{1-6}$alkyl, C$_{3-8}$cycloalkyl, heteroC$_{3-8}$ cycloalkyl (e.g., pyrrolidinyl or piperidinyl) haloC$_{1-6}$alkyl (e.g., trifluoromethyl), aryl (e.g., phenyl), heteroaryl (e.g., pyridyl, (for example, pyrid-2-yl) or e.g., thiadiazolyl (for example, 1,2,3-thiadiazol-4-15 yl), diazolyl, triazolyl (e.g., 1,2,4-triazol-1-yl), tetrazolyl (e.g., tetrazol-5-yl), alkoxadiazolyl (e.g., 5-methyl-1,2,4-oxadiazol), pyrazolyl (e.g., pyrazol-i-yi), alkyl sulfonyl (e.g., methyl sulfonyl), arylcarbonyl (e.g., benzoyl), or heteroarylcarbonyl, alkoxycarbonyl, (e.g., methoxycarbonyl), aminocarbonyl; preferably phenyl, pyridyl, e.g., 2-pyridyl, piperidinyl, or pyrrolidinyl; wherein the aryl, heteroaryl cycloalkyl or heterocycloalkyl is optionally substituted with one or more halo (e.g., F or Cl), C$_{1-6}$alkly, C$_{1-6}$alkoxy, C$_{1-4}$haloalkyl (e.g., trifluoromethyl), and/or —SH, provided that when X, Y or X is nitrogen, R$_8$, R$_9$ or R$_{10}$, respectively, is not present;

(v) R$_4$ is
H, C$_{1-6}$alkyl (e.g., methyl, isopropyl),
C$_{3-8}$cycloalkyl (e.g., cyclopentyl), C$_{3-8}$heterocycloalkyl (e.g., pyrrolidin-3-yl), aryl (e.g., phenyl) or heteroaryl (e.g., pyrid-4-yl, pyrid-2-yl or pyrazol-3-yl) wherein said aryl or heteroaryl is optionally substituted with halo (e.g., 4-fluorophenyl), hydroxy (e.g., 4-hydroxyphenyl), C$_{1-6}$alkyl, C$_{1-6}$alkoxy or another aryl group (e.g., biphenyl-4-ylmethyl); (vi) R$_{14}$ and R$_{15}$ are independently H or C$_{1-6}$alkyl, in free or salt form.

The invention further provides the use of PDE1 inhibitors of any of the preceding formulae (e.g., Formula I, II, III, IV, V, VI, VII, VIII, IX, X, XI), wherein the compound is selected from any of the following:

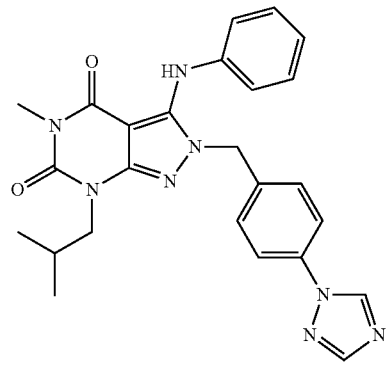

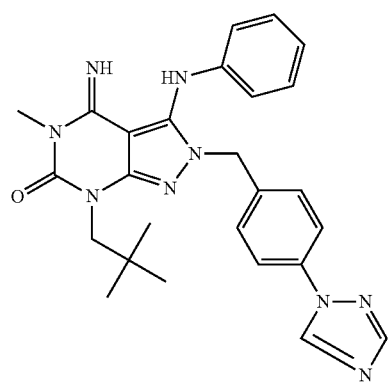

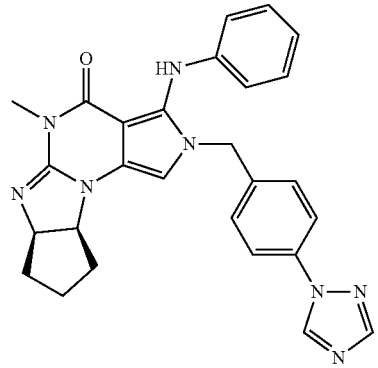

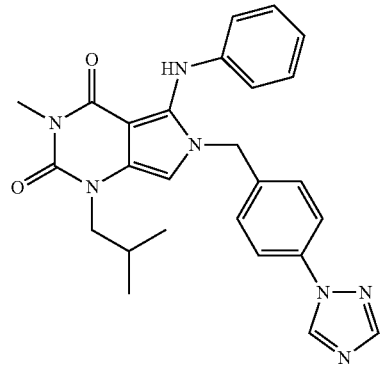

31
-continued
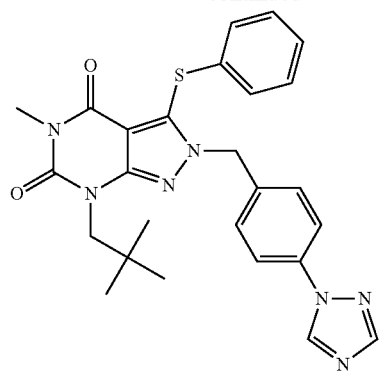
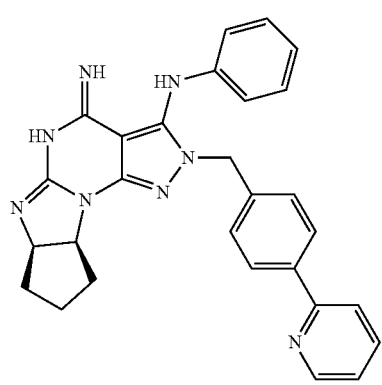
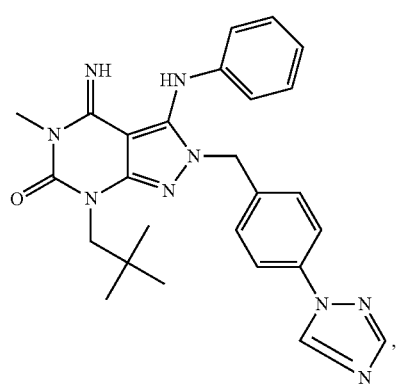
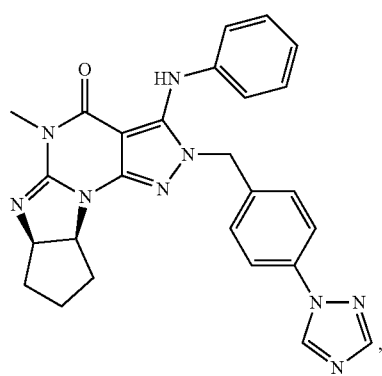
32
-continued
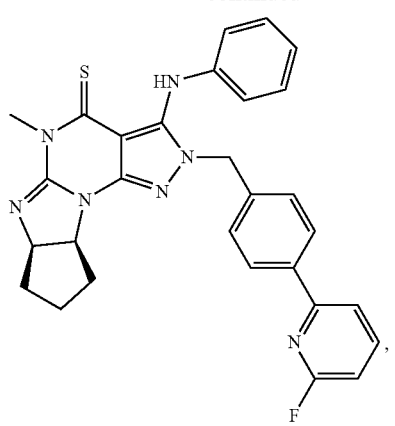
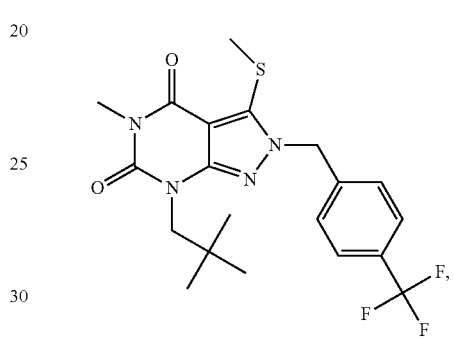
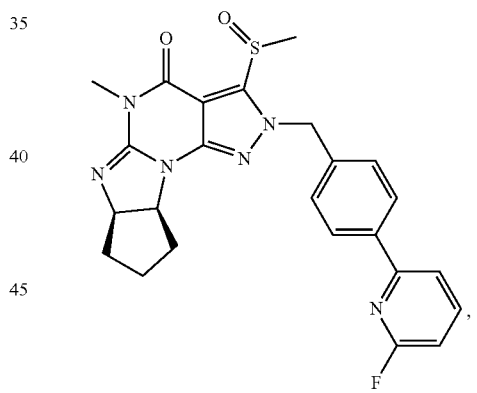
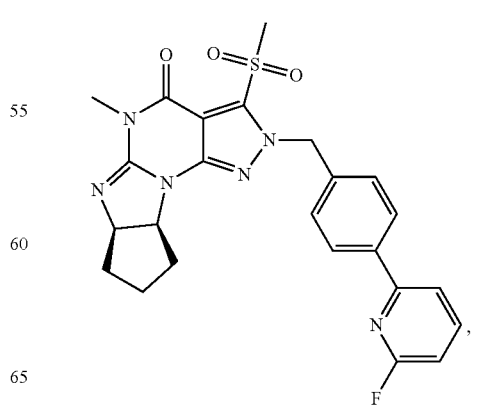

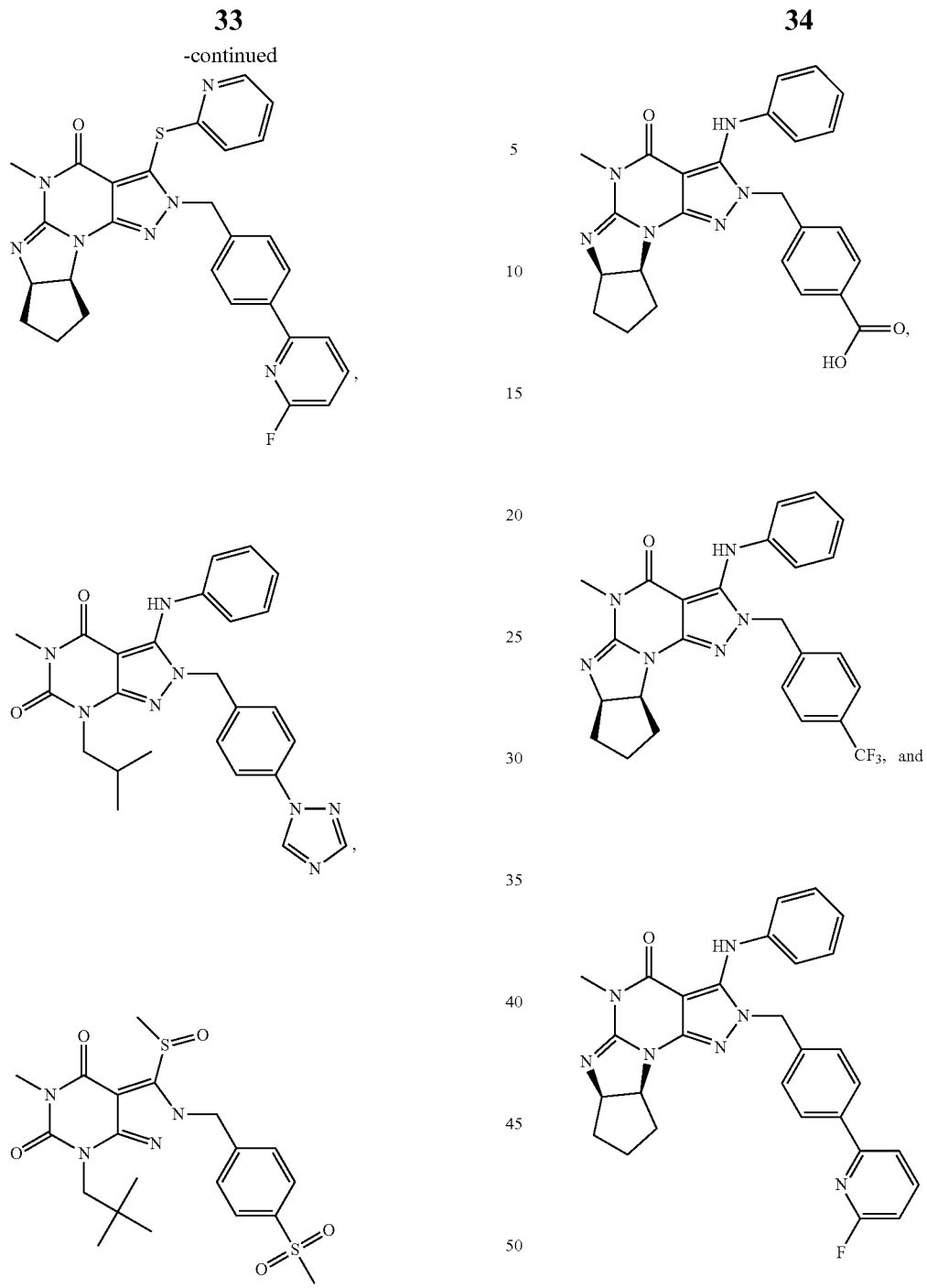

In one embodiment, preferred compounds of the any of the preceding formulae (e.g., Formula I, II, III, IV, V, VI, VII, VIII, IX, X, XI) are compounds that inhibit phosphodiesterase-mediated (e.g., PDE1-mediated, especially PDE1A or PDE1C-mediated) hydrolysis of cGMP, e.g., the preferred compounds have an $IC_{50}$ of less than 1 µM, preferably less than 500 nM, preferably less than 50 nM, and preferably less than 5 nM in an immobilized-metal affinity particle reagent PDE assay, in free or salt form.

In another embodiment, the preferred PDE1 inhibitors of any of the preceding formulae (e.g., Formula I, II, III, IV, V, VI, VII, VIII, IX, X, XI) are compounds selected from the following:

In a further embodiment, the preferred PDE1 inhibitors are selective for PDE1 (generally, off-target interactions are greater than 100× lower than affinity for PDE1), exhibit good oral bioavailability, and exhibit minimal brain penetration (e.g., blood/plasma concentration ratios of less than 0.4, more preferably less than 0.2).

In another aspect, the present invention also includes the novel combination of any of the PDE1 inhibitors of the preceding formulae (e.g., Formula I, II, III, IV, V, VI, VII, VIII, IX, X, XI) with any selective NEP inhibitor. In a preferred embodiment, the aforementioned PDE1 inhibitor is a selective PDE1 inhibitor.

In another embodiment of the present invention, the PDE1 inhibitor is a 1,3,5-substituted 6,7-dihydro-1H-pyrazolo[4,3-d]pyrimidin-7-one, of formula XV:

Formula (XV)

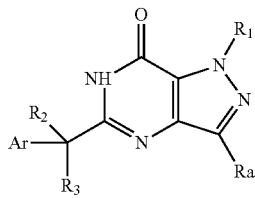

wherein:
$R_a$ is methyl or $C_2$-$C_6$ alkyl;
$R_1$ is H or $C_1$-$C_4$ alkyl; each of $R_2$ and $R_3$ is independently selected from H and $C_1$-$C_4$ alkyl, or $R_2$ is H or $C_1$-$C_4$ alkyl and $R_3$ is OH, $C_2$-$C_4$ alkanoyloxy or fluoro, or $R_2$ and $R_3$ when taken together represent $C_2$-$C_6$ alkylene, or $R_2$ and $R_3$ when taken together with the carbon atom to which they are attached represent a carbonyl group;
Ar is either (a)

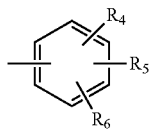

wherein each of $R_4$, $R_5$ and $R_6$ is independently selected from H
$C_1$-$C_4$ alkyl,
$C_1$-$C_4$ alkoxy,
$C_1$-$C_4$ alkoxy-Z—, halo, halo($C_1$-$C_4$)alkyl, phenoxy, optionally substituted by up to three substituents each of which substituent is independently selected from halo, $C_{1-4}$ alkyl, and $C_1$-$C_4$ alkoxy, nitro, hydroxy, hydroxy-Z—,
$C_2$-$C_4$ alkanoyl, amino, amino-Z—, ($C_1$-$C_4$ alkyl)NH, ($C_1$-$C_4$ alkyl)$_2$N—,
($C_1$-$C_4$ alkyl)NH—Z—,
($C_1$-$C_4$ alkyl)$_2$N—Z—,
—COOH, —Z—COOH,
—COO($C_1$-$C_4$ alkyl),
—Z—COO($C_1$-$C_4$ alkyl)
$C_1$-$C_4$ alkanesulfonamido,
$C_1$-$C_4$ alkanesulfonamido-Z—, halo($C_1$-$C_4$)alkanesulfonamido, halo($C_1$-$C_4$)alkanesulfonamido-Z—,
$C_1$-$C_4$ alkanamido,
$C_1$-$C_4$ alkanamido-Z—,
HOOC—Z—NH—,
HOOC—Z—NH—Z—, ($C_1$-$C_4$ alkyl)OOC—Z—NH—,
($C_1$-$C_4$ alkyl)OOC—Z—NH—Z—,
$C_1$-$C_4$ alkyl-NH—SO$_2$—NH—,
$C_1$-$C_4$ alkyl-NH—SO$_2$—NH—Z—,
($C_1$-$C_4$ alkyl)$_2$-N—SO$_2$—NH—, ($C_1$-$C_4$ alkyl)$_2$-N—SO$_2$—NH—Z—,
$C_1$-$C_4$ alkoxy CH=CH—Z—CONH—,
$C_1$-$C_4$ alkoxy CH=CHCONH
$C_1$-$C_4$ alkyl-SO$_2$—N($C_1$-$C_4$ alkyl)-,
$C_1$-$C_4$ alkyl-SO$_2$—N($C_1$-$C_4$ alkyl)-Z—, ($C_1$-$C_4$ alkyl)NH—Z—SO$_2$—NH—,
($C_1$-$C_4$ alkyl)$_2$N—Z—SO$_2$—NH—,
($C_1$-$C_4$ alkyl)NH—Z—SO$_2$—NH—Z—,
($C_1$-$C_4$ alkyl)$_2$N—Z—SO$_2$—NH—Z—, benzenesulfonamido, optionally ring substituted by up to three substituents each of which is independently selected from halo, $C_{1-4}$ alkyl, and
$C_1$-$C_4$ alkoxy,
$C_1$-$C_4$ alkanoyl-N($C_1$-$C_4$ alkyl)-,
$C_1$-$C_4$ alkanoyl-N($C_1$-$C_4$ alkyl)-Z—,
$C_1$-$C_4$ alkoxycarbonyl-CH(CH$_2$OH)NHSO$_2$—,
—SO$_3$H,
—SO$_2$NH$_2$,
H$_2$NOC—CH(CH$_2$OH)—NHSO$_2$—,
HOOC—Z—O—, and
($C_1$-$C_4$ alkyl)OOC—Z—O—, or optionally one of $R_4$, $R_5$ and $R_6$ is a G-Het group and wherein the others of $R_4$, $R_5$ and Re are independently selected from the R4, $R_5$ and $R_6$ substituents listed above;
Z is $C_1$-$C_4$ alkylene,
G is a direct link, Z, O, —SO$_2$NH—, SO$_2$, or —Z—N ($C_1$-$C_4$ alkyl)SO$_2$—,
Het is a 5- or 6-membered heterocyclic group containing 1, 2, 3 or 4 nitrogen heteroatoms; or 1 or 2 nitrogen heteroatoms and 1 sulfur heteroatom or 1 oxygen heteroatom; or the heterocyclic group is furanyl or thiophenyl; wherein the Het group is saturated or partially or fully unsaturated and optionally substituted by up to 3 substituents, wherein each substituent is independently selected from $C_1$-$C_4$ alkyl, oxo, hydroxy, halo, and halo($C_1$-$C_4$) alkyl;
or (b) any one of the following bicyclic groups:
benzodioxolanyl, benzodioxanyl, benzimidazolyl, quinolinyl, indolyl, quinazolinyl, isoquinolinyl, benzotriazolyl, benzofuranyl, benzothiophenyl, quinoxalinyl, or phthalizinyl, wherein said bicyclic Ar groups are linked to the neighboring —C($R_2R_3$)— group via the benzo ring portion,
and wherein the heterocyclic portion of said bicyclic Ar group is optionally partially or fully saturated, said group being optionally substituted by one or more of $C_1$-$C_4$ alkyl, halo, hydroxy, oxo, amino, and $C_1$-$C_4$ alkoxy;
or a pharmaceutically acceptable salt of the compound, or a pharmaceutically acceptable solvate of the compound or the salt.

In another embodiment of the present invention, the PDE1 inhibitor is a compound of Formula XV of the following formulae:
3.2 Of Formula XV wherein $R_a$ is a $C_{2-5}$ alkyl group;
3.3 Of Formula XV wherein $R_3$ is a $C_{2-4}$ alkyl group.
3.4 Of Formula XV wherein $R_3$ is a $C_3$ alkyl group.
3.5 Of Formula XV wherein $R_3$ is methyl
3.6 Of Formula XV, 3.2, 3.3, 3.4 or 3.5 wherein $R_1$ is a $C_{1-6}$ alkyl group.
3.7 Of any of the preceding formulae wherein $R_1$ is a $C_{1-3}$ alkyl group.
3.8 Of any of the preceding formulae wherein $R_1$ is a methyl group.
3.9 Of any of the preceding formulae wherein $R_2$ is H.
3.10 Of any of the preceding formulae wherein $R_3$ is H.
3.11 Of any of the preceding formulae wherein $R_4$, $R_5$ and $R_6$ are independently selected from H, ($C_{1-4}$ alkyl)$_2$N—, $C_{1-4}$ alkanesulphonamido and benzenesulfonamido.
3.12 Of any of the preceding formulae wherein $R_4$, $R_5$ and $R_6$ are independently selected from H, diethylamino, methanesulfonamido and benzenesulfonamido.
3.13 Of any of the preceding formulae wherein Ar is 4-diethylaminophenyl.
3.14 Of any of the preceding formulae wherein Ar is 2-methanesulfonamido-phenyl.

3.15 Of any of the preceding formulae wherein Ar is 4-benzenesulfonamido-phenyl
3.16 Of any of the preceding formulae wherein one of $R_4$, $R_5$ and $R_6$ is $(C_{1-4}\ alkyl)_2N-$ and wherein the other two of $R_4$, $R_5$ and $R_6$ are H.
3.17 Of any of the preceding formulae wherein one of $R_4$, $R_5$ and $R_6$ is diethylamino and wherein the other two of $R_4$, $R_5$ and $R_6$ are H.
3.18 Of any of the preceding formulae wherein $R_3$ is methyl.
3.19 Of any of the preceding formulae wherein $R_3$ is $C_2$-$C_6$ alkyl.
3.20 Of any of the preceding formulae wherein the compound is selected from the following:

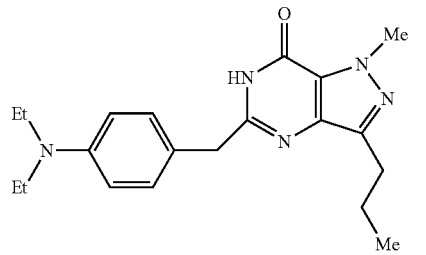

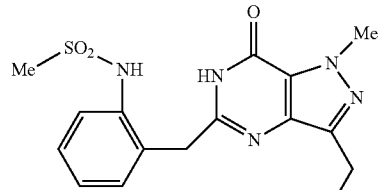

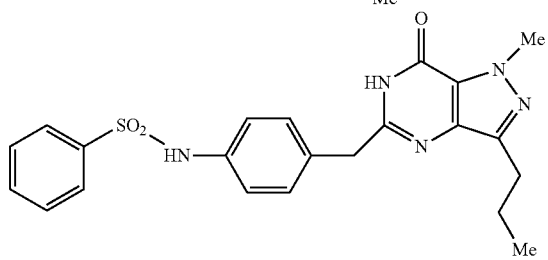

3.21 Of any of the preceding formulae wherein the compound is

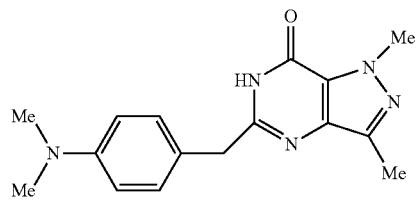 [SMILES: Cc1nn(C)c2c(=O)[nH]c(Cc3ccc(N(C)C)cc3)nc12]

3.22 A compound which is a 1,3,5,-substituted, 6,7-dihydro-1H-pyrazolo[4,3-f1f]pyrimidin-7-one, in free or pharmaceutically acceptable salt form, e.g. a compound of Formula XV or according to any of formulae 3.2-3.21, wherein the compound inhibits phosphodiesterase-mediated (e.g., PDE1-mediated) hydrolysis of cGMP, e.g., with an $IC_{50}$ of less than 1 μM, preferably less than 25 nM.

In another embodiment of the present invention, the PDE1 inhibitor is a substituted imidazo[2,1-b]purin-4-one of Formula XVII-a or XVII-b:

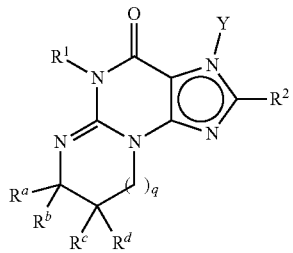
Formula XVII-a

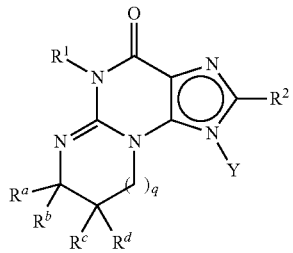
Formula XVII-b in free, salt or prodrug form, including its enantiomers, diastereomers and racemates, wherein:
  (i) q=0, 1 or 2;
  (ii) $R^1$, $R^a$, $R^b$, $R^c$ and $R^d$ are each independently H, alkyl, aryl, heteroaryl, cycloalkyl or heterocycloalkyl groups, wherein each alkyl group of $R^1$, $R^a$, $R^b$, $R^c$ and $R^d$ is independently unsubstituted or substituted with 1 to 5 independently selected $R^3$ moieties which can be the same or different, each $R^3$ moiety being independently selected from the group consisting of hydroxy, alkoxy, cycloalkoxy, aryloxy, alkylthio, arylthio, aryl, haloaryl, heteroaryl, cycloalkyl, heterocycloalkyl, amino, alkylamino, dialkylamino, cycloalkylamino and heterocycloalkylamino groups;
  wherein each of the aryl, heteroaryl, cycloalkyl and heterocycloalkyl groups of $R^1$, $R^a$, $R^b$, $R^c$ and $R^d$ is independently unsubstituted or substituted with 1 to 5 independently selected $R^4$ moieties which can be the same or different, each
  $R^4$ moiety being independently selected from the group consisting of: halo, optionally substituted aryl (e.g., phenyl, chlorophenyl, methoxyphenyl), heteroaryl (e.g., pyridyl, pyrrolyl), nitro, cyano, haloalkyl, haloalkoxy, alkyl, alkoxy, cycloalkyl, heterocycloalkyl (e.g., pyrrolidinyl, morpholin-4-yl, pyrrol-1-yl), cycloalkylalkyl, amino, alkylamino, dialkylamino, —$OCF_3$, acyloxy, —$OR^8$, —$C(O)R^9$, —$C(O)OR^8$, —$NR^{10}C(O)R^9$, —$NR^{10}C(O)OR^8$, —$NR^{10}S(O)_2R^9$, —$S(O)o_{-2}R^9$ groups, carbonyl when two hydrogens attached to the same carbon atom of the cycloalkyl or heterocycloalkyl group of R' are substituted, and =$CR^8R^9$ when two hydrogens attached to the same carbon atom of the cycloalkyl or heterocycloalkyl groups of $R^1$ are substituted,
  wherein each of the aryl, heteroaryl, cycloalkyl and heterocycloalkyl groups of the $R^3$ and $R^4$ moieties above is independently unsubstituted or substituted with 1 to 5 independently selected $R^{12}$ moieties which can be the same or different, each $R^{12}$ moiety being independently selected from the group consisting of:

halo, phenyl, nitro, cyano, haloalkyl, haloalkoxy, alkyl, cycloalkyl, cycloalkylalkyl, amino, alkylamino, —OCF$_3$, acyloxy, —OR$^8$, —C(O)R$^9$, —C(O)OR$^8$, —NR$^{10}$C(O)R$^9$, —NR$^{10}$C(O)OR$^8$, —NR$^{10}$S(O)$_2$R$^9$, —S(O)$_{0-2}$R$^9$ groups, carbonyl when two hydrogens attached to the same carbon atom of the cycloalkyl or heterocycloalkyl group of R or R$^4$ are substituted, and =CR$^8$R$^9$ when two hydrogens attached to the same carbon atom of the cycloalkyl or heterocycloalkyl group of R$^3$ or R$^4$ are substituted; or (iii) R$^a$ and R$^b$, together with the carbon to which they are both attached, form a 4- to 7-membered cycloalkyl or heterocycloalkyl ring, and R$^c$ and R$^d$ are each independently H or an alkyl group; or (iv) R$^a$ and R$^c$, together with the respective carbons to which they are attached, form a 4- to 7-membered cycloalkyl or heterocycloalkyl ring, and R$^b$ and R$^d$ are each independently H or an alkyl group, preferably R$^a$ and R$^c$ together have the cis configuration, e.g., where the carbons carrying R$^a$ and R$^c$ have the R and S configurations, respectively;

(v) R$^2$ is H, halo, alkyl, haloalkyl, alkoxy, alkylthio, amino, aminosulfonyl, monoalkylamino, dialkylamino, hydroxyalkylamino, aminoalkylamino, carboxy, alkoxycarbonyl, aminocarbonyl or alkylaminocarbonyl group, wherein each alkyl group of R is independently unsubstituted or substituted with 1 to 5 independently selected R$^{13}$ moieties which can be the same or different, each R$^{13}$ moiety being independently selected from the group consisting of halo, hydroxy, alkoxy, alkyl, aryl (e.g., phenyl, napthyl) heteroaryl (e.g., 1H-imidazol-2-yl), cycloalkyl, heterocycloalkyl (e.g., pyrolidin-1-yl), amino, monoalkylamino or dialkylamino group, wherein each aryl group of R$^{13}$ is independently unsubstituted or substituted with 1 to 5 independently selected R$^4$ moieties which can be the same or different;

(vi) Y is H or an alkyl group substituted with (i) an aryl, heteroaryl, cycloalkyl, hydroxy, alkoxy, amino, monoalkylamino or dialkylamino group, or (ii) an aryl group substituted with from one to three moieties each independently selected from the group consisting of: halo, alkyl, phenyl, hydroxy, alkoxy, phenoxy, amino, monoalkylamino and dialkylamino group;

(vii) each R$^8$ is independently H, alkyl or aryl;

(viii) each R$^9$ is independently H, alkyl, aryl or —NR$^{10}$R$^{11}$;

(ix) each R$^{10}$ is independently H, alkyl, aryl, heteroaryl, arylalkyl or heteroarylalkyl, wherein each alkyl, aryl, heteroaryl, arylalkyl or heteroarylalkyl of R$^{10}$ is unsubstituted or independently substituted with 1 to 5 R$^{14}$ moieties which can be the same or different, each R$^{14}$ moiety being independently selected from the group consisting of: halo, alkyl, aryl, cycloalkyl, —CF$_3$, —OCF$_3$, —CN, —OR$^8$, —CH$_2$OR$^8$, —C(O)OR$^8$ and —C(O)NR$^8$R$^8$; and (x) each R$^{11}$ is independently H, alkyl, aryl, heteroaryl, arylalkyl or heteroarylalkyl, wherein each alkyl, aryl, heteroaryl, arylalkyl or heteroarylalkyl of R$^{11}$ is unsubstituted or independently substituted with 1 to 5 R$^{14}$ moieties which can be the same or different;

and wherein the numbering of the ring system of the Formula XVII-a or XVII-b is, for example, as follows for q=0 and q=1, respectively:

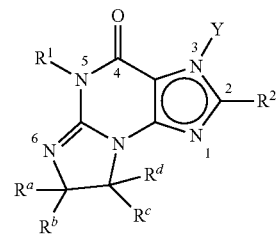

Formula XVII-a

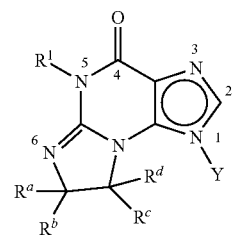

Formula XVII-b

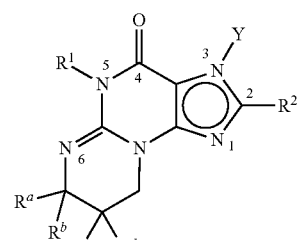

Formula XVII-a

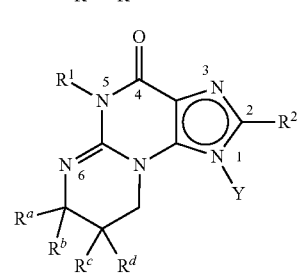

Formula XVII-b

In another embodiment of the present invention, the PDE1 inhibitor is a compound according to Formula XVII-a or XVII-b, in free or salt form, as follows:

4.1: Formula XVII-a or XVII-b, wherein q=0, 1 or 2;

4.2: Formula XVII-a or XVII-b, wherein q=0;

4.3: Formula XVII-a or XVII-b or 4.1 or 4.2, wherein R$^1$ is alkyl;

4.4: Formula XVII-a or XVII-b or 4.1-4.2, wherein R$^1$ is methyl;

4.5: Formula XVII-a or XVII-b or 4.1-4.4, wherein R$^a$ and R$^c$, together with the respective carbons to which they are attached, form a 4- to 7-membered cycloalkyl or heterocycloalkyl ring, and R$^b$ and R$^d$ are each independently H or an alkyl group;

4.6: Formula XVII-a or XVII-b or 4.1-4.4, wherein R$^a$ and R$^c$, together with the respective carbons to which they are attached, form a 5-membered heterocycloalkyl ring, and R$^b$ and R$^d$ are each independently H;

4.7: Formula XVII-a or XVII-b or 4.1-4.4, wherein R$^a$ and R$^b$, together with the respective carbons to which they are attached, form a 5-membered heterocycloalkyl ring, and R$^c$ and R$^d$ are each independently H;

4.8: Formula XVII-a or XVII-b or 4.1-4.7, wherein R$^2$ is alkyl or haloalkyl;

4.9: Formula XVII-a or XVII-b or 4.1-4.7, wherein R² is biphenyl-4-ylmethyl;
4.10: Formula XVII-a or XVII-b or 4.1-4.7, wherein R² is benzyl;
4.11: Formula XVII-a or XVII-b or 4.1-4.7, wherein R² is cyclopentylmethyl;
4.12: Formula XVII-a or XVII-b or 4.1-4.7, wherein R² is cyclopropylmethyl;
4.13: Formula XVII-a or XVII-b or 4.1-4.12, wherein Y is benzyl; and/or
4.14: Of any of the preceding formulae wherein the compound is selected from the following:

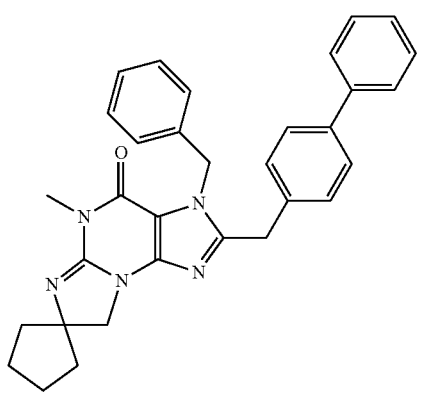

,

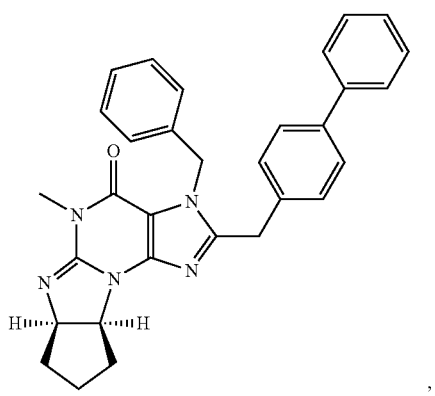

,

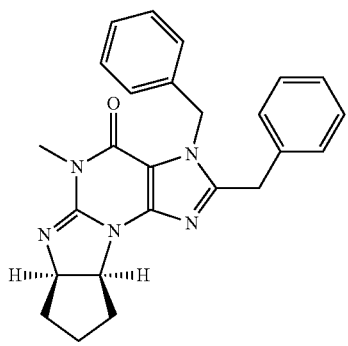

and

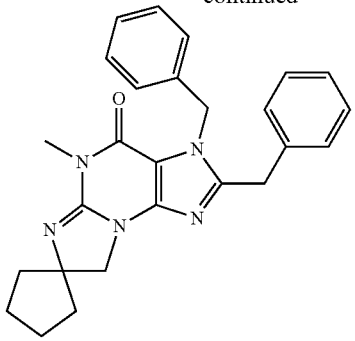

4.15: Of any of the preceding formulae wherein the compound is

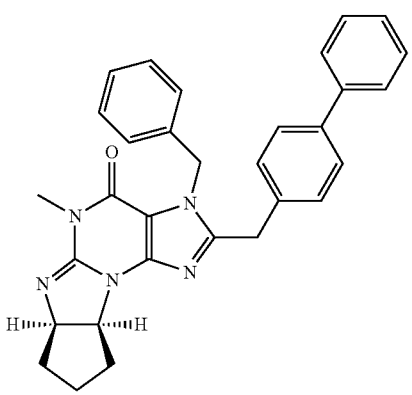 [SMILES: CN1C(=O)c2c(nc(Cc3ccc(-c4ccccc4)cc3)n2Cc2ccccc2)N2C1=N[C@@H]1CCC[C@@H]12]

4.16: A compound which is a substituted imidazo[2,1-b]purin-4-one, in free or pharmaceutically acceptable salt form, e.g. a compound of Formula XVII-a or XVII-b according to any of formulae 4.1-4.15, wherein the compound inhibits phosphodiesterase-mediated (e.g., PDE1-mediated) hydrolysis of cGMP, e.g., with an $IC_{50}$ of less than 1 μM, preferably less than 25 nM.

In another embodiment of the present invention, the PDE1 inhibitor is preferably a compound of Formula XVII-a or XVII-b are selected from a group consisting of:

(6aR,9aS)-5,6a,7,8,9,9a-hexahydro-5-methyl-2,3-bis(phenylmethyl)cyclopent[4,5]imidazo[2,1-b]purin-4(3H)-one, (6aR,9aS)-2-(biphenyl-4-ylmethyl)-5,6a,7,8,9,9a-hexahydro-5-methyl-3-(phenylmethyl)cyclopent[4,5]imidazo[2,1-b]purin-4(3H)-one, 5'-methyl-2',3'-bis(phenylmethyl)spiro[cyclopentane-1,7'(8'H)-[3H]imidazo[2,1b]-purin]-4' (5'H)-one, and 5'-methyl-2'-(biphenyl-4-ylmethyl)-3'-(phenylmethyl)spiro-[cyclopentane-1,7'(8'H)-[3H]imidazo[2,1-b]purin]-4 (5'H)-one, in free or pharmaceutically acceptable salt form. In an especially preferred embodiment, compound of Formula XVII-a is (6aR,9aS)-2-(biphenyl-4-ylmethyl)-5,6a,7,8,9,9a-hexahydro-5-methyl-3-(phenylmethyl)cyclopent-[4,5]imidazo[2,1-b]purin-4(3H)-one, in free or salt form.

In another embodiment of the present invention, the PDE1 inhibitor is a compound of Formula XVIII-a or XVIII-b:

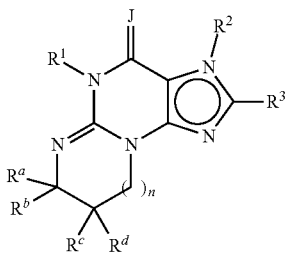

Formula XVIII-a

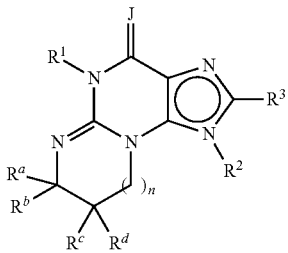

Formula XVIII-b in free or salt form, wherein:
(i) J is oxygen or sulfur,
(ii) $R^1$ is hydrogen, alkyl or alkyl substituted with aryl or hydroxy;
(iii) $R^2$ is hydrogen, aryl, heteroaryl, cycloalkyl, alkyl or alkyl substituted with aryl, heteroaryl, hydroxy, alkoxy, amino, monoalkyl amino or dialkylamino, or —$(CH_2)_m$TCOR$^{20}$ wherein m is an integer from 1 to 6, T is oxygen or —NH— and $R^{20}$ is hydrogen, aryl, heteroaryl, alkyl or alkyl substituted with aryl or heteroaryl;
(iv) $R^3$ is hydrogen, halo, trifluoromethyl, alkoxy, alkylthio, alkyl, cycloalkyl, aryl, aminosulfonyl, amino, monoalkylamino, dialkylamino, hydroxyalkylamino, aminoalkylamino, carboxy, alkoxycarbonyl or aminocarbonyl or alkyl substituted with aryl, hydroxy, alkoxy, amino, monoalkylamino or dialkylamino;
(v) $R^a$, $R^b$, $R^c$ and $R^d$ independently represent hydrogen, alkyl, cycloalkyl or aryl; or ($R^a$ and $R^b$) or ($R^c$ and $R^d$) or ($R^b$ and $R^c$) can complete a saturated ring of 5- to 7-carbon atoms, or ($R^a$ and $R^b$) taken together and ($R^b$ and $R^c$) taken together, each complete a saturated ring of 5- to 7-carbon atoms, wherein each ring optionally can contain a sulfur or oxygen atom and whose carbon atoms may be optionally substituted with one or more or the following: alkenyl, alkynyl, hydroxy, carboxy, alkoxycarbonyl, alkyl or alkyl substituted with hydroxy, carboxy or alkoxycarbonyl; or such saturated ring can have two adjacent carbon atoms which are shared with an adjoining aryl ring; and
(vi) n is zero or one.

In another embodiment of the present invention, the PDE1 inhibitor is a compound of Formula XVIII-a or XVIII-b, in free or salt form, as follows:
5.1: Formula XVIII-a or XVIII-b, wherein J=O.
5.2: Formula XVIII-a or XVIII-b or 5.1, wherein $R^1$ is alkyl.
5.3: Formula XVIII-a or XVIII-b, 5.1 or 5.2, wherein $R^2$ is hydrogen, benzyl, 4-chlorobenzyl, cyclohexylmethyl or trimethylacetoxymethyl.
5.4: Formula XVIII-a or XVIII-b, 5.1, 5.2 or 5.3, wherein $R^3$ is hydrogen, or alkyl such as methyl or ethyl.
5.5: Formula XVIII-a or XVIII-b, 5.1, 5.2, 5.3 or 5.4, wherein n is zero; and
5.6: Formula XVIII-a or XVIII-b, 5.1, 5.2, 5.3, 5.4 or 5.5, wherein $R^a$ and $R^b$ form a saturated 5 membered ring, or (R and $R^c$) form a saturated 5, 6 or 7 membered ring, or ($R^a$ and $R^b$) and ($R^b$ and $R^c$) each complete a saturated ring and each ring contains 5 or 6 carbon atoms.

In another embodiment of the present invention, the PDE1 inhibitor is a compound of Formula XVIII-a or XVIII-b, in free or salt form, selected from the following:
cis-5,6a,7,8,9,9a-Hexahydro-5-methyl-3-(phenylmethyl)cyclopenta[4,5]imidazo-[2,1-b]purin-4-one;
7,8-Dihydro-5-methyl-3-(phenylmethyl)-3H-imidazo[2,1-b]purin-4(5H)-one;
cis-6a,7,8,9,10,10a-Hexahydro-5-methyl-3-(phenylmethyl)-3H-benzimidazo[2,1-b]purin-4(5H)-one;
5,7,8,9-Tetrahydro-5-methyl-3-(phenylmethyl)pyrimido[2,1-b]purin-4(3H)-one;
7,8-Dihydro-8-phenyl-5-methyl-3-(phenylmethyl)-3H-imidazo[2,1-b]purin-4(5H)-one;
5',7'-Dihydro-5'-methyl-3'-(phenylmethyl)spiro[cyclohexane-1,8'-(8H)imidazo-[2,1-b]purin]4'(3H)-one;
cis-5,6a,11,11a-Tetrahydro-5-methyl-3-(phenylmethyl)indeno[1',2':4,5]imidazo-[2,1-b]purin-4(3H)-one;
5',7'-Dihydro-2',5'dimethyl-3'-(phenylmethyl)spiro{cyclohexane-1,7'(8'H)-imidazo[2,1-b]purin}-4'-(3'H)-one;
7,8-Dihydro-2,5,7,7,8(R,S)-pentamethyl-3H-imidazo[2,1-b]purin-4(5H)-one;
cis-5,6a,7,11b-Tetrahydro-5-methyl-3-(phenylmethyl)indeno[2',1':4,5]imidazo[2,1-b]purin-4(3H)-one;
cis-5,6a,7,8,9,9a-Hexahydro-2,5-dimethyl-3-(phenylmethyl)cyclopent[4,5]-imidazo[2,1-b]purin-4-(3H)-one;
5'-Methyl-3'-(phenylmethyl)-spiro[cyclopentane-1,7'-(8'H)-(3'H)imidazo[2,1-b]purin]-4-(5'H)-one;
7,8-Dihydro-2,5,7,7-tetramethyl-3-(phenylmethyl)-3H-imidazo[2,1-b]purin-4(5H)-one;
7,8-Dihydro-7(R)-phenyl-2,5-dimethyl-3-(phenylmethyl)-3H-imidazo[2,1-b]purin-4(5H)-one;
7,8-Dihydro-2,5-dimethyl-3,7(R)-bis(phenylmethyl)-3H-imidazo[2,1-b]purin-4(5H)-one;
(±)-7,8-Dihydro-2,5-dimethyl-7-ethyl-3-(phenylmethyl)-3H-imidazo[2,1-b]purin-4(5H)-one;
6a(S)-7,8,9,10,10a(R)-Hexahydro-2,5-dimethyl-3-(phenylmethyl)-3H-benzimidazo[2,1-b]purin-4(5H)-one;
6a(R)-7,8,9,10,10a(S)-hexahydro-2,5-dimethyl-3-(phenylmethyl)-3H-benzimidazo-[2,1 b]purin-4(5H)-one;
7,8-Dihydro-2,5-dimethyl-7(R)-isopropyl-3-(phenylmethyl)-3H-imidazo[2,1-b]purin-4(5H)-one;
7,8-Dihydro-2,5,7(R)-trimethyl-3-(phenylmethyl)-3H-imidazo[2,1-b]purin-4(5H)-one;
cis-7,7a,8,9,10,10a-Hexahydro-2,5-dimethyl-3-(phenylmethyl)-3H-cyclopenta-[5,6]pyrimido[2,1-b]purin-4(5H)-one;
7,8-Dihydro-2,5-dimethyl-7(S)-(1-methylpropyl)-3-(phenylmethyl)-3H-imidazo-[2,1-b]purin-4(5H)-one;
7,8-Dihydro-2,5-dimethyl-7(R)-(2-methylpropyl)-3-(phenylmethyl)-3H-imidazo-[2,1-b]purin-4(5H)-one;
7,8-Dihydro-2,5-dimethyl-7(R,S)-(methoxycarbonyl)-3-(phenylmethyl)-3H-imidazo[2,1-b]purin-4(5H)-one;
7,8-Dihydro-2,5-dimethyl-7(R,S)-(1-propyl)-3-(phenylmethyl)-3H-imidazo[2,1-b]purin-4(5H)-one;
7,8-Dihydro-2,5-dimethyl-7(S)-(1-methylethyl)-3-(phenylmethyl)-3H-imidazo[2,1-b]purin-4(5H)-one;
7,8-Dihydro-2,5,7,7,8(R,S)-pentamethyl-3H-imidazo[2,1-b]purin-4(5H)-one;
5,7,8,9-Tetrahydro-2,5,7,9(R,S)-pentamethyl-3-(phenylmethyl)-pyrimido[2,1-b]purin-4(3H)-one;

5,6a(R),7,8,9,9a(S)-Hexahydro-2,5-dimethyl-3-(phenylmethyl)cyclopent-[4,5]imidazo[2,1-b]purin-4(3H)-one;

5,6a(S),7,8,9,9a(R)-Hexahydro-2,5-dimethyl-3-(phenylmethyl)cyclopent-[4,5]imidazo[2,1-b]purin-4(3H)-one;

cis-6a,7,8,9,10,10a-Hexahydro-2,5-dimethyl-3-(phenylethyl)-3H-benzimidazo[2,1-b]purin-4(5H)-one;

5¹,7'-Dihydro-2¹,5¹-dimethyl-3'-(phenylmethyl)spiro[cyclohexane-1,8-(8H)-imidazo[2,1-b]purin]-4-(3H)-one;

cis-5,6a,7,8,9,9a-Hexahydro-2,5-dimethyl-3-(phenylmethyl)cyclohept-[6,7]imidazo[2,1-b]purin-4(3H)-one;

cis-5,6a,7,8,9,9a-Hexahydro-5-methyl-2-ethyl-3-(phenylmethyl)cyclopent-[4,5]imidazo[2,1-b]purin-4(3H)-one;

cis-6a,7,8,9,10,10a-Hexahydro-5-methyl-2-ethyl-3-(phenylmethyl)-3H-benzimidazo[2,1-b]purin-4-(5H)-one;

cis-5,6a,7,8,9,9a-Hexahydro-5-methyl-2-ethyl-3-(phenylmethyl)cyclopent-[4,5]imidazo[2,1-b]purin-4(3H)-one;

cis-5,6a,7,8,9,9a-Hexahydro-5-methyl-2-phenyl-3-(phenylmethyl)cyclopent-[4,5]imidazo[2,1-b]purin-4(3H)-one;

cis-6a,7,8,9, 10, 10a-Hexahydro-5-methyl-2-phenyl-3-(phenylmethyl)-3H-benzimidazo[2,1-b]purin-4(5H)-one;

cis-5,6a,7,8.9,9a-Hexahydro-5-methylcyclopenta[4,5]imidazo[2,1-b]purin-4(3H)-one;

cis-5,6a,7,8,9,9a-Hexahydro-2,5-dimethylcyclopenta[4,5]imidazo[2,1-b]purin-4(3H)-one;

cis-5,6a(R), 7,8,9,9a(S)-Hexahydro-2,5-dimethylcyclopent[4,5]imidazo[2,1-b]purin-4(3H)-one;

2',5'-dimethyl-spiro{cyclopentane-1,7'-(8'H)-(3'H)-imidazo[2,1-b]purin}-4' (5'H)-one;

7,8-Dihydro-2,5-dimethyl-7(R)-(1-methylethyl)-3H-imidazo[2,1-b]purin-4(5H)-one;

7,8-Dihydro-2,5,7,7-tetramethyl-3H-imidazo[2,1-b]purin-4(5H)-one;

7,8-Dihydro-2,5-dimethyl-7(S)-(1-methylethyl)-3H-imidazo[2,1-b]purin-4(5H)-one;

6a(R),7,8,9,10,10a(S)-Hexahydro-2,5-dimethyl-3H-benzimidazo[2,1-b]purin-4(5H)-one;

5',7'-Dihydro-2',5'-dimethylspiro{cyclohexane-1,7-(8'H)-imidazo[2,1-b]purin}-4'(3'H)-one;

cis-5,6a,7,8,9,9a-Hexahydro-5-methyl-3-(phenylmethyl)cyclopenta[4,5]-imidazo[2,1-b]purin-4(3H)-thione;

5,6a(R),7,8,9,9a(S)-Hexahydro-2,5-dimethyl-3-(phenylmethyl)cyclopent-[4,5]imidazo[2,1-b]purin-4(3H)-thione;

cis-5,6a,7,8,9,9a-Hexahydro-5-methyl-3-(4-chlorophenylmethyl)cyclopenta[4,5]-imidazo[2,1-b]purin-4(3H)-one;

cis-5,6a,7,8,9,9a-Hexahydro-5-methyl-3-(cyclohexylmethyl)cyclopent[4,5]imidazo[2,1-b]purin-4(3H)-one;

cis-5,6a,7,8,9,9a-Hexahydro-5-methyl-3-(2-naphthylmethyl)cyclopent[4,5]imidazo[2,1-b]purin-4(3H)-one;

5,6a(R),7,8,9,9a(S)-Hexahydro-2,5-dimethyl-3-(4-bromophenylmethyl)-cyclopent[4,5]imidazo[2,1-b]purin-4(3H)-one;

5,6a(R)-7,8,9,9a(S)-Hexahydro-2,5-dimethyl-3-(4-methoxyphenylmethyl)-cyclopent[4,5]imidazo[2,1-b]purin-4(3H)-one;

cis-5,6a,7,8,9,9a-Hexahydro-2,3,5-trimethylcyclopent[4,5]imidazo[2,1-b]purin-4(3H)-one;

cis-5,6a,7,8,9,9a-Hexahydro-2-(hydroxymethyl)-5-methyl-3-(phenylmethyl)-cyclopent[4,5]imidazo[2,1-b]purin-4(3H)-one;

cis-5,6a,7,8,9,9a-Hexahydro-2-methylthio-5-methyl-3-(phenylmethyl)cyclopent-[4,5]imidazo[2,1-b]purin-4(3H)-one;

cis-3,4,5,6a,7,8,9,9a-Octahydro-5-methyl-4-oxo-3-(phenylmethyl)cyclopent-[4,5]imidazo[2,1-b]purin-2-carboxylic acid;

cis-3,4,5,6a,7,8,9,9a-Octahydro-5-methyl-4-oxo-3-(phenylmethyl)cyclopent-[4,5]imidazo[2,1-b]purin-2-carboxylic acid, methyl ester;

cis-5,6a,7,8,9,9a-Hexahydro-2-bromo-5-methyl-3-(phenylmethyl)cyclopent[4,5]imidazo[2,1-b]purin-4(3H)one;

cis-5,6a,7,8,9,9a-Hexahydro-2-(methylaminosulfonyl)-5-methyl-3-(phenylmethyl)cyclopent[4,5]imidazo[2,1-b]purin-4(3H)one;

cis-1-Cyclopentyl-5,6a,7,8,9,9a-hexahydro-5-methylcyclopent[4,5]imidazo[2,1-b]purin-4-(1H)one;

cis-5,6a,7,8,9,9a-Hexahydro-3,5-bis-(phenylmethyl)cyclopent(4,5)imidazo (2,1-b)purin-4(3H)one;

cis-6a,7,8,9,10,10a-Hexahydro-3,5-bis-(phenylmethyl)-3H-benzimidazo[2,1-b]purin-4(5H)one;

cis-3-Cyclopentyl-5,6a,7,8,9,9a-hexahydro-5-methylcyclopent[4,5]imidazo(2,1-b)purin-4(3H)one;

5'-Methyl-3'-(phenylmethy)spiro[cyclopentane-1,7-(8'H)-(3'H)imidazo[2,1-b]purin]-4-(5H)one;

2¹,5'-Dimethyl-3'-(phenylmethyl)-Spiro[cyclopentane-1,7-(8'H)-(3'H)imidazo[2,1-b]purin]-4-(5' H)one;

cis-5,6a,(R)7,8,9,9a(S)-Hexahydro-5-methyl-3-(phenylmethyl)cyclopent[4,5]-imidazo(2,1-b)purin-4(3H)one;

cis-3-Cyclopentyl-5,6a,7,8,9,9a-Hexahydro-2,5-dimethyl-cyclopent[4,5]imidazo-[2,1-b]purin-4(3H)one;

5'-Methyl-2'-trifluoromethyl-3'-(phenylmethyl)spiro{cyclopentane-1,7'(8'H)-(3'H)imidazo[2,1-b]purin}-4-(5'H)-one;

7,8-Dihydro-5,7,7-trimethyl-2-trifluoromethyl-3-(phenylmethyl)-3H-imidazo[2,1-b]purin-4(5H)-one;

(+/−)-cis-5,6a,7,8,9,9a-Hexahydro-5-methyl-2-trifluoromethyl-3-(phenylmethyl)-cyclopent[4,5]imidazo[2,1-b]purin-4(3H)-one;

(+/−)-6a,7,8,9,9a,10,11,11a-Octahydro-2,5-dimethyl-3-(phenylmethyl)-3H-pentaleno[6a',1':4,5]imidazo[2,1-b]purin-4(5H)-one;

(+)-6a,7,8,9,9a, 10,11,11a-Octahydro-2,5-dimethyl-3-phenylmethyl-3H-pentaleno[6a',1':4,5]imidazo[2,1-b]purin-4(5H)-one;

(−)-6a,7,8,9,9a,10,11,11a-Octahydro-2,5-dimethyl-3-phenylmethyl-3H-pentaleno[6a',1':4,5]Imidazo[2,1-b]purin-4(5H)-one;

(+/−) 6a,7,8,9,9a, 10,11,11a-Octahydro-2,5-dimethyl-3H-pentaleno[6a',1':4,5]-imidazo[2,1-b]purin-4(5H)-one;

(+)-6a,7,8,9,9a,10,11,11a-Octahydro-2,5-dimethyl-3H-pentaleno[6a',1':4,5]-imidazo[2,1-b]purin-4(5H)-one;

(−)-6a,7,8,9,9a, 10,11,11a-Octahydro-2,5-dimethyl-3H-pentaleno[6a',1':4,5]-imidazo[2,1-b]purin-4(5H)-one;

6a,7,8,9, 10,10a,11,12,13,13a-Decahydro-2,5-dimethyl-(3-phenylmethyl)-napth[1,8a-d]imidazo[2,1-b]purin-4(5H) one;

7(R)-Cyclohexyl-7,8-dihydro-2,5-dimethyl-3-(phenylmethyl)-3H-imidazo[2,1-b]purin-4(3H)-one;

7(R)-Cyclohexyl-7,8-dihydro-2,5-dimethyl-3H-imidazo[2,1-b]purin-4(5H)-one;

7(S)-Cyclohexyl-7,8-dihydro-2,5-dimethyl-3-(phenylmethyl)-3H-imidazo[2,1-b]purin-4(3H)-one;

7(S)-Cyclohexyl-7,8-dihydro-2,5-dimethyl-3H-imidazo[2,1-b]purin-4(5H)-one;

5,6a(R),7,8,9,9a(S)-Hexahydro-2,5-dimethyl-[3-(trimethylacetoxy)methyl]-cyclopent[4,5]imidazo[2,1-b]purin-4(3H)-one;

5,6a(R),7,8,9,9a(S)-Hexahydro-2,5-dimethyl-3-(4-pyridylmethyl)cyclopent[4,5]imidazo[2,1-b]purin-4(3H)-one;

5,6a(R),7,8,9,9a(S)-Hexahydro-2,5-dimethyl-3-[2-(4-morpholinyl)-ethyl]cyclopent[4,5]imidazo[2,1-b]purin-4(3H)-one;

5,6a(R),7,8,9,9a(S)-Hexahydro-2,5-dimethyl-3-[acetoxymethyl]cyclopent-[4,5]imidazo[2,1-b]purin-4(3H)-one;

5,6a,7,8,9,9a-Hexahydro-2,5,6a-trimethyl-3-(phenylmethyl)cyclopent-[4,5]imidazo[2,1-b]purin-4(3H)-one;

5,6a(R),7,8,9,9a(S)-Hexahydro-2,5,6a-trimethyl-3-(phenylmethyl)-cyclopent[4,5]imidazo[2,1-b]purin-4(3H)-one;

5,6a(S),7,8,9,9a(R)-Hexahydro-2,5,6a-trimethyl-3-(phenylmethyl)cyclopent[4,5]imidazo[2,1-b]purin-4(3H)-one;

cis-6a,7,8,9, 10,10a-Hexahydro-2,5,7-trimethyl-3-(phenylmethyl)-3H-benzimidazo[2,1-b]purin-4(5H)-one;

cis-5,6a,7,8,9,9a-Hexahydro-2,5,6a-trimethylcyclopent[4,5]imidazo[2,1-b]purin-4(3H)-one; or cis-[6a,7,8,9, 10,10a-Hexahydro-2,5,7-trimethyl-3H-benzimidazo[2,1-b]purin-4(5H)-one].

In another embodiment of the present invention, the PDE1 inhibitor is a compound of Formula XIX-a or XIX-b:

Formula XIX-a

Formula XIX-b or a pharmaceutically acceptable salt thereof, wherein,
(a) q=0 or 1;
(b) $R^1$ is H, cycloalkyl, alkyl, $R^{23}$-alkyl- or $R^{26}$.
(c) $R^a$, $R^b$ and $R^c$ are, independently of one another, each H, alkyl, cycloalkyl, aryl, $R^{22}$-aryl- or $R^{24}$-alkyl-; or
$R^a$ and $R^b$, together with the carbon to which they are both attached, form a 4- to 7-membered ring, and $R^c$ is H or alkyl; or
$R^a$ and $R^c$, together with the respective carbons to which they are attached, form a 4- to 7-membered ring, and $R^b$ is H or alkyl;
(d) for the group X—$R^2$,
  (i) X is a bond;
  Y is aryl-alkyl or $R^{22}$-aryl-alkyl-; and
  $R^2$ is monohaloalkyl, polyhaloalkyl, provided that it is not trifluoromethyl, azido, cyano, oximino, cycloalkenyl, heteroaryl, $R^{22}$-heteroaryl- or $R^{27}$-alkyl-; or
  (ii) X is a bond;
  Y is aryl-alkyl or $R^{22}$-aryl-alkyl-; and
  $R^2$ is H, halo, —CONH$R^6$, —CON$R^6R^7$, —CO$_2R^6$, monohaloalkyl, polyhaloalkyl, azido, cyano, —C═N—O$R^6$, cycloalkyl, cycloalkylalkyl, $R^{26}$, aminosulfonyl, alkyl or $R^{23}$-alkyl-; or
  (iii) X is —O— or —S—;
  Y is aryl-alkyl or $R^{22}$-aryl-alkyl-; and
  $R^2$ is $R^{26}$, cycloalkyl, cycloalkylalkyl, heterocloalkyl, cycloalkenyl or $R^{26}$-alkyl-; or
  (iv) X is —O— or —S—;
  Y is aryl-alkyl or $R^{22}$-aryl-alkyl-; and $R^2$ is alkyl, $R^{26}$, cycloalkyl, cycloalkylalkyl, heterocycloalkyl, cycloalkenyl or $R^{28}$-alkyl-; or
  (v) X is —SO— or —SO$_2$—;
  Y is aryl-alkyl or $R^{22}$-aryl-alkyl-; and
  $R^2$ is alkyl, $R^{26}$, cycloalkyl, cycloalkylalkyl, heterocycloalkyl, cycloalkenyl or $R^{28}$-alkyl-; or
  (vi) X is —N$R^8$—;
  Y is aryl-alkyl or $R^{22}$-aryl-alkyl-; and
  $R^2$ is $(R^{29})_p$-alkyl-, cycloalkyl, $(R^{30})_p$-cycloalkyl-, cycloalkenyl, $(R^{30})_p$-cycloalkenyl-, heterocycloalkyl or $(R^{30})_p$-heterocycloalkyl-; or
  (vii) X is —N$R^8$—;
  Y is aryl-alkyl or $R^{22}$-aryl-alkyl-; and
  $R^2$ is alkyl, $R^{26}$, cycloalkyl, cycloalkylalkyl, heterocycloalkyl, cycloalkenyl or $R^{31}$-alkyl-; or
  (viii) X is —C≡C—;
  Y is aryl-alkyl or $R^{22}$-aryl-alkyl-; and
  $R^2$ is alkyl, $R^{26}$, cycloalkyl, cycloalkylalkyl or $R^{23}$-alkyl-;
(e) wherein,
  $R^6$ is H or $R^7$;
  $R^7$ is alkyl, cycloalkyl or cycloalkylalkyl;
  $R^8$ is heterocycloalkyl or $R^6$;
  $R^{21}$ is 1-6 substituents each independently selected from the group consisting of halo, hydroxy, alkoxy, phenoxy, phenyl, nitro, aminosulfonyl, cyano, monohaloalkyl, polyhaloalkyl, thiol, alkylthio, cycloalkyl, cycloalkylalkyl, amino, alkylamino, acylamino, carboxyl, —C(O)O$R^{34}$, carboxamido, —OCF$_3$ and acyloxy;
  $R^{22}$ is 1-6 substituents each independently selected from the group consisting of alkyl and $R^{21}$;
  $R^{23}$ is cycloalkoxy, aryloxy, alkylthio, arylthio, cycloalkyl or $R^{28}$;
  $R^{24}$ is cycloalkyl or $R^{26}$;
  $R^{25}$ is hydroxy, alkoxy, amino, monoalkylamino, dialkylamino or $R^{26}$;
  $R^{26}$ is aryl, $R^{22}$-aryl-, heteroaryl or $R^{22}$-heteroaryl-;
  $R^{27}$ is cycloalkoxy, aryloxy, alkylthio, arylthio, heteroaryl, $R^{22}$-heteroaryl-, cycloalkyl, heterocycloalkyl, cycloalkenyl, cycloalkylamino or heterocycloalkylamino;
  $R^{28}$ is cycloalkylamino, heterocycloalkylamino or $R^{25}$;
  $R^{29}$ is alkoxy, cycloalkylamino, heterocycloalkylamino or $R^{26}$;
  $R^{30}$ is halo, hydroxy, alkoxy, amino, aminosulfonyl, cyano, monohaloalkyl, polyhaloalkyl, thiol, alkylthio, alkyl, cycloalkyl, cycloalkylalkyl or acyloxy;
  $R^{31}$ is cycloalkyl or $R^{28}$;
  $R^{34}$ is alkyl, aryl, aralkyl and heteroaryl; and
  p is 1 to 4.

In another embodiment of the present invention, the PDE1 inhibitor is a compound of Formula XIX-a or XIX-b, in free or salt form, selected from the following:

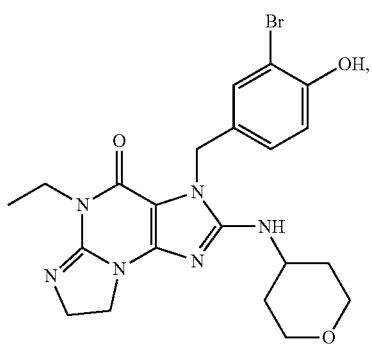
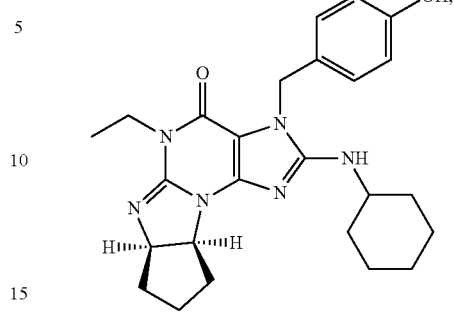
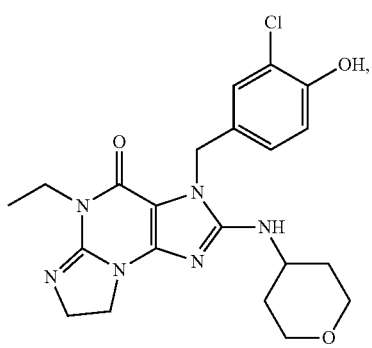
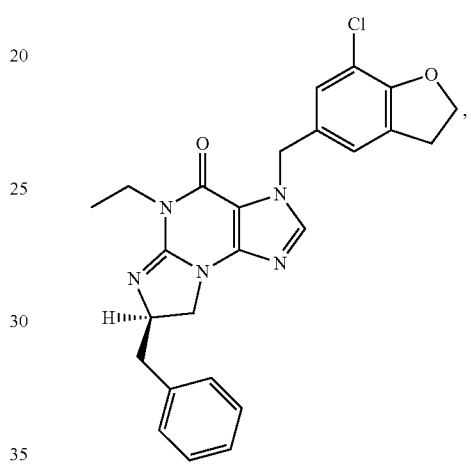
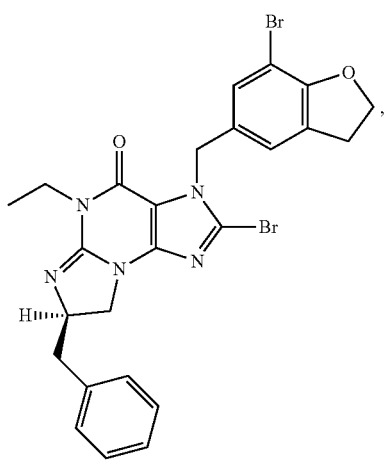
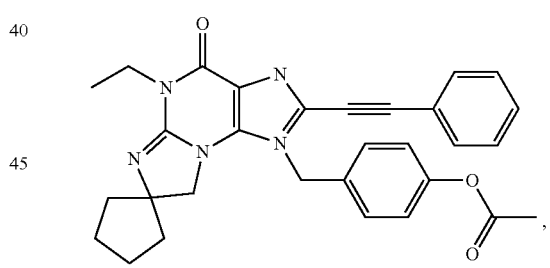
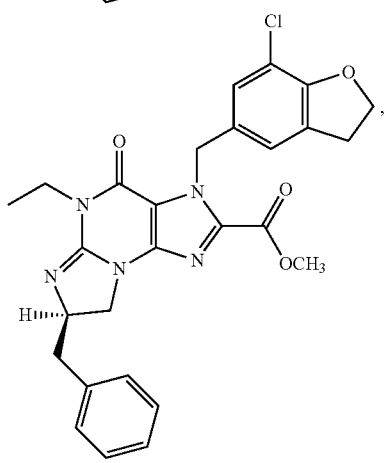
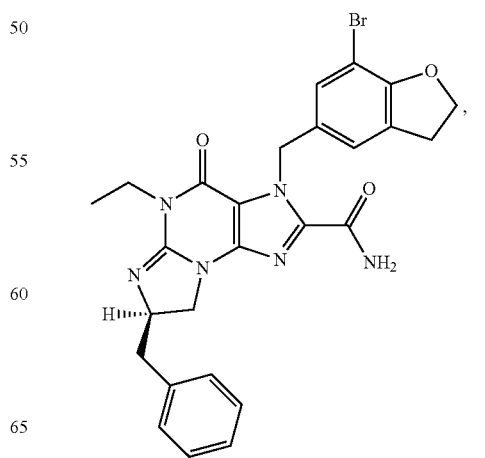

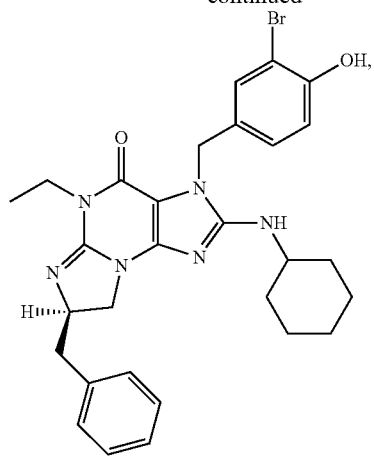
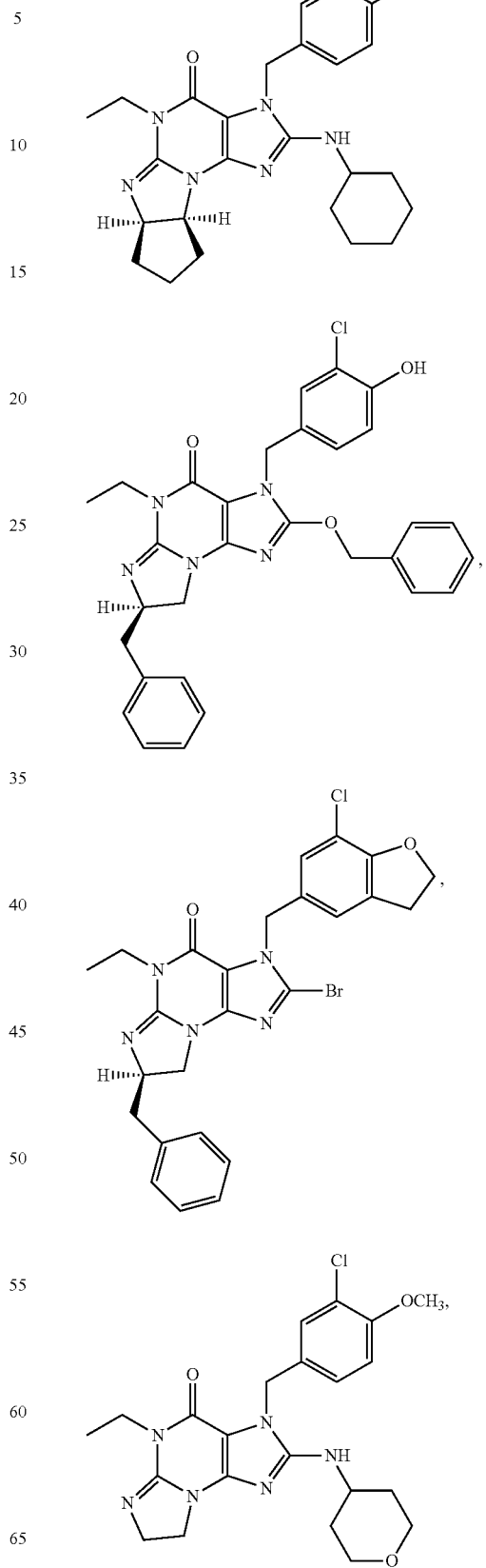

53
-continued
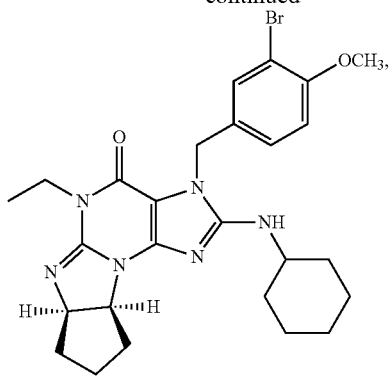
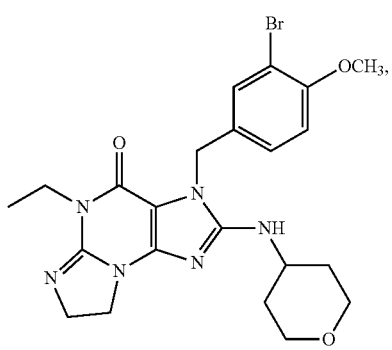
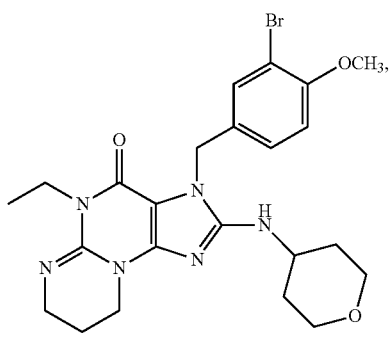
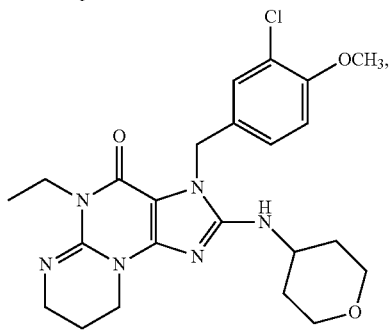
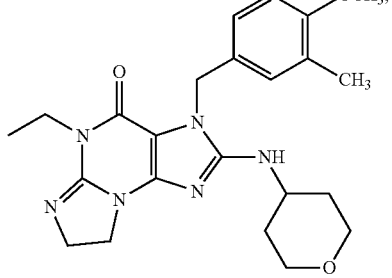
54
-continued
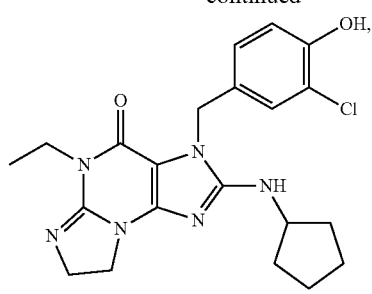
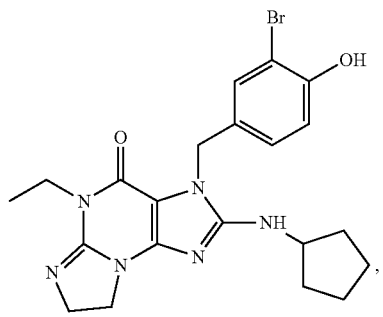
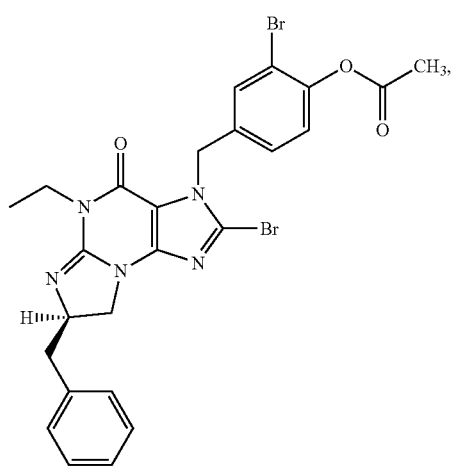
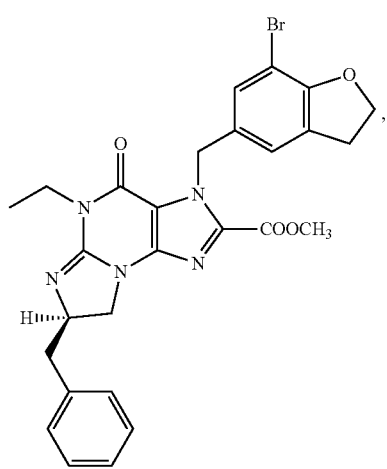

-continued

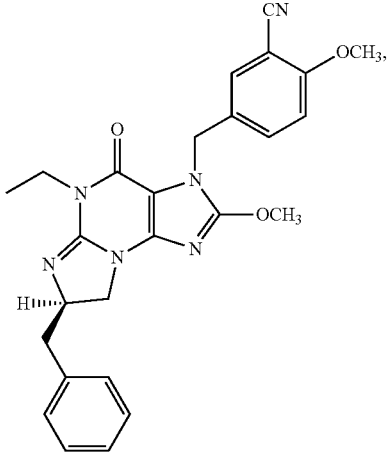

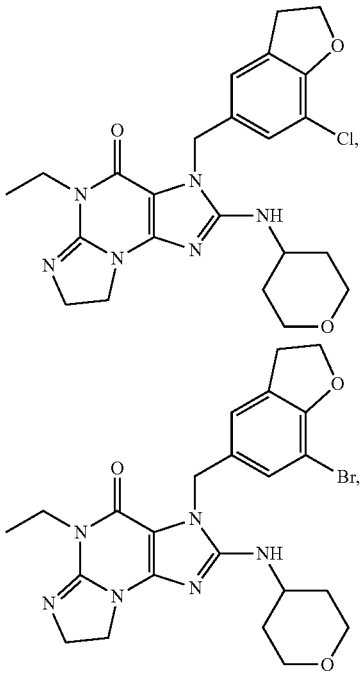

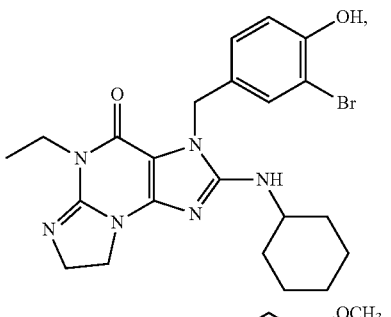

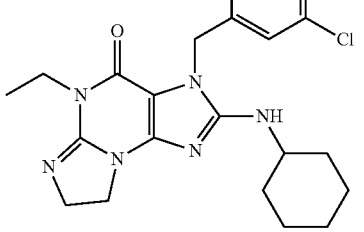 and

-continued

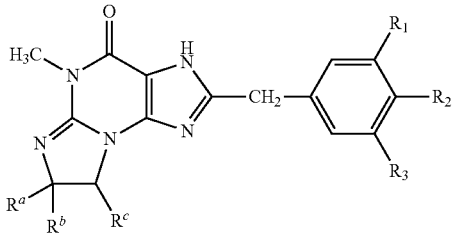

In another embodiment of the present invention, the PDE1 inhibitor is a compound of Formula XX:

$$\text{Formula XX}$$

in free or a pharmaceutically acceptable salt thereof, wherein:
(a) $R_1$, $R_2$ and $R_3$ are independently selected from the group consisting of hydrogen, lower alkyl, lower alkoxy, halogen, hydroxy, (di-lower alkyl)amino, 4-morpholinyl, 1-pyrrolidinyl, 1-pyrrolyl, —$CF_3$, —$OCF_3$, phenyl and methoxyphenyl;
or $R_1$ and $R_2$ together are methylenedioxy;
or $R_1$ and $R_2$ together with the carbon atoms to which they are attached form a benzene ring; and
(b) $R^a$ is hydrogen and $R^b$ and $R^c$, together with the carbon atoms to which they are attached, form a saturated ring of 5 carbons;
or $R^a$ is lower alkyl, $R^b$ is hydrogen or lower alkyl, and $R^c$ is hydrogen;
or $R^a$, $R^b$ and the carbon atom to which they are attached form a saturated ring of 5-7 carbons, and $R^c$ is hydrogen;
or $R^a$ is hydrogen, and $R^b$, $R^c$ and the carbon atoms to which they are attached form a tetrahydrofuran ring;
or $R^a$ and $R^b$, together with the carbon atom to which they are attached, and $R^b$ and $R^c$, together with the carbon atoms to which they are attached, each form a saturated ring of 5-7 carbons.

In another embodiment of the present invention, the PDE1 inhibitor a compound of Formula XX as follows:
7.1 Formula XX, wherein $R_1$, $R_2$ and $R_3$ are independently selected from the group consisting of hydrogen, lower alkyl, lower alkoxy, halogen, hydroxy, (di-lower alkyl)amino, 4-morpholinyl, 1-pyrrolidinyl, 1-pyrrolyl, —$CF_3$, —$OCF_3$, phenyl and methoxyphenyl; or $R_1$ and $R_2$ together are methylenedioxy; or $R_1$ and $R_2$ together with the carbon atoms to which they are attached form a benzene ring;
7.2 Formula XX or 7.1, wherein $R_1$ is H, methoxy or trifluoromethyl;

7.3 Formula XX or 7.1 or 7.2, wherein $R_1$ is H;

7.4 Formula XX or any of 7.1-7.3, wherein $R_2$ is selected from a group consisting of
H, halo (e.g., F, Cl), methoxy, methyl, trifluoromethyl, dimethylamino, phenyl, methoxyphenyl-, —$OCF_3$, 3,4-$OCH_2O$—, pyrolidin-1-yl, pyrol-1-yl and morpholin-4-yl;

7.5 Formula XX or any of 7.1-7.4, wherein $R_1$ and $R_2$ together with the carbon atoms to which they are attached forma a benzene ring;

7.6 Formula XX or any of 7.1-7.5, wherein $R_3$ is H or methoxy;

7.7 Formula XX or any of 7.1-7.6, wherein $R_3$ is H;

7.8 Formula XX or any of 7.1-7.7, wherein $R^a$ is hydrogen and R and $R^c$, together with the carbon atoms to which they are attached, form a saturated ring of 5 carbons; or $R^a$ is lower alkyl, $R^b$ is hydrogen or lower alkyl, and $R^c$ is hydrogen; or $R^a$, $R^b$ and the carbon atom to which they are attached form a saturated ring of 5-7 carbons, and $R^c$ is hydrogen; or $R^a$ is hydrogen, and $R^b$, $R^c$ and the carbon atoms to which they are attached form a tetrahydrofuran ring; or $R^a$ and $R^b$, together with the carbon atom to which they are attached, and $R^b$ and $R^c$, together with the carbon atoms to which they are attached, each form a saturated ring of 5-7 carbons;

7.9 Formula XX or any of 7.1-7.8, wherein $R^a$ is hydrogen and $R^b$ and $R^c$ together with the carbon atoms to which they are attached, form a saturated ring of 5 carbons, and wherein $R_1$, $R_2$ and $R_3$ are as defined in the following table

| $R_1$ | $R_2$ | $R_3$ |
|---|---|---|
| H | H | H |
| —$OCH_3$ | H | H |
| H | F | H |
| H | —$OCH_3$ | H |
| H | OH | H |
| H | —$CH_3$ | H |
| H | $(CH_3)_2N$— | H |
| —$OCH_3$ | —$OCH_3$ | —$OCH_3$ |
| —$OCH_3$ | —$OCH_3$ | H |
| —$CF_3$ | H | H |
| H | $C_2H_5$— | H |
| H | —$OCF_3$ | H |
| H | —N pyrrolidine | H |
| H | —N pyrrole | H |
| H | 3,4-$OCH_2O$— | H |
| H | —N morpholine | H |
| H | —phenyl-$OCH_3$ | H |
| $R_1$ and $R_2$, together with the carbon atoms to which they are attached form a benzene ring | | H |
| H | Cl | H |

7.10 Formula XX or any of 7.1-7.9, selected from a group consisting of:

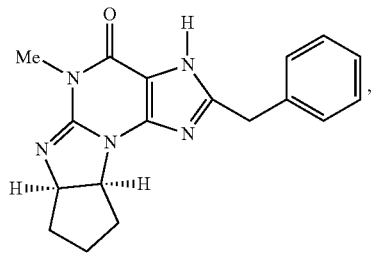

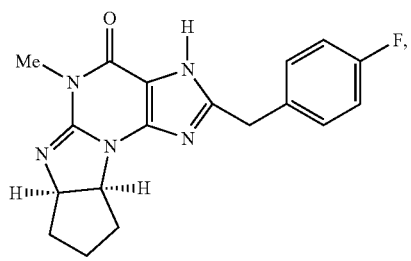

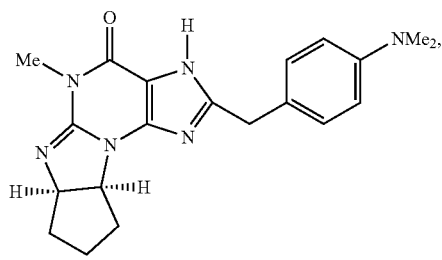

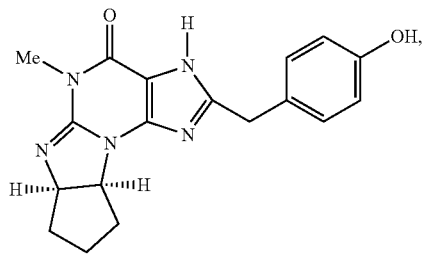

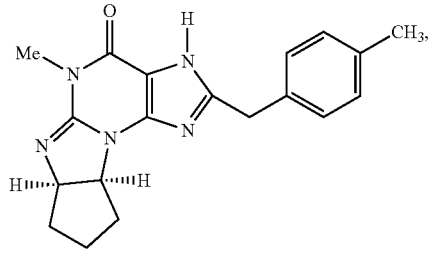

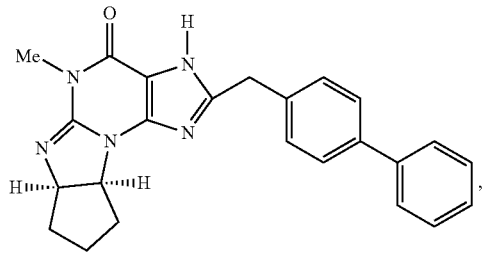

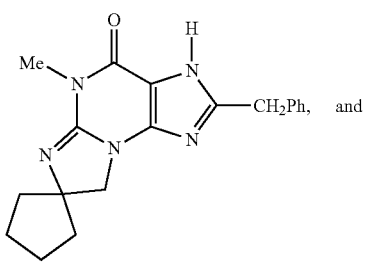

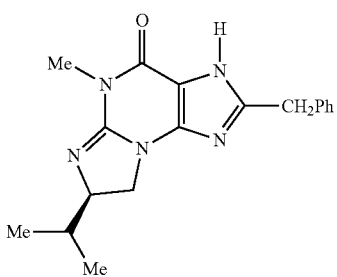

7.11 Formula XX or any of 7.1-7.9, selected from a group consisting of:

2¹-benzyl-5'-methyl-spiro[cyclopentane-1',7' (8'H)-[3'H]-imidazo[2,1-b]purin]-4'-(5'H)-one;

2'-benzyl-5,7,7-trimethyl-3H-imidazo[2,1-b]purin-4-(5H)-one;

(+)-2-benzyl-7,8-dihydro-5-methyl-7-(1-methylethyl)-1H-imidazo[2,1-b]-purin-4(5H)-one;

(+,−)-6a, 7, 8, 9, 9a, 10, 11, 11a-octahydro-5-methyl-2-(3,4-methylene-dioxyphenylmethyl)-3H-pentalen[6a,1:4,5]imidazo[2,1-b]purin-4(5H)-one; and (+)-cis-6a,7,9,9a-tetrahydro-5-methyl-2-[4-(trifluoromethyl)-phenylmethyl]-3H-furo[3',4':4,5]imidazo[2,1-b]purin-4(5H)-one, in free or salt form.

7.12 Formulae XX or 7.1-7.11, wherein the compounds inhibit phosphodiesterase-mediated (e.g., PDE1-mediated) hydrolysis of cGMP, e.g., with an IC$_{50}$ of less than 1 µM, preferably less than 25 nM.

In another embodiment of the present invention, the PDE1 inhibitor is a compound selected from the following:

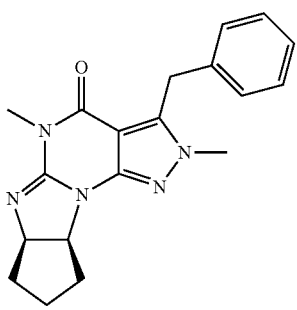

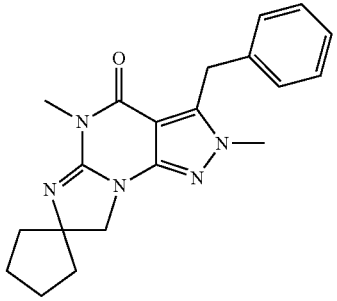

, and in free or salt form (Formula XXI).

In another embodiment of the present invention, the PDE1 inhibitor is a compound of Formula XXII:

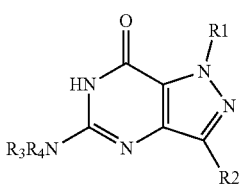

Formula XXII wherein,

R$^1$ represents a group selected from H, C$_1$-C$_6$ alkyl, C$_2$-C$_6$ alkenyl, C$_2$-C$_6$ alkynyl, cycloalkyl optionally substituted with one or more of OH, CF$_3$, CN, halogen or —CONH$_2$ or C$_1$-C$_6$ alkyl;

R$^2$ represents a group selected from H, C$_1$-C$_6$ alkyl, C$_2$-C$_6$ alkenyl, C$_2$-C$_6$ alkynyl, cycloalkyl optionally substituted with one or more of OH, CF$_3$, CN, halogen or —CONH$_2$ or C$_1$-C$_6$ alkyl;

R$^3$ represents
(i) alkyl (e.g., C$_1$-C$_6$ alkyl),
(ii) substituted or unsubstituted aryl or substituted or unsubstituted aralkyl (e.g., (CH$_2$)$_m$-aryl, wherein the aryl may be optionally substituted by one or more of halo, CF$_3$, OCH$_3$, heteroaryl, CH$_2$-heterocycloalkyl containing 2 or more heteroatoms, N-linked heterocycloalkyl optionally substituted with one more of C$_1$-C$_4$ alkyl, CF$_3$, halogen, or heteroaryl), or (iii) substituted or unsubstituted heteroaryl or substituted or unsubstituted heteroarylalkyl (e.g., $(CH_2)_n$-heteroaryl, wherein the heteroaryl may be optionally substituted by one or more aryl or two or more $C_1$-$C_4$ alkyl); or (iv) aryl optionally substituted by one or more halogen, where each "m" independently represents 0, 1 or 2, and each "n" independently represents 0 or 1;

$R^4$ represents H or alkyl (e.g., $C_1$-$C_6$ alkyl);

or $R^3$ and $R^4$ together with the N to which they are attached may form (i) heterocycloalkyl unsubstituted or substituted with alkyl, aralkyl, halo substituted aralkyl, heteroarylalkyl or halo substituted heteroarylalkyl (e.g., where the heterocycloalkyl is a 4-7 membered N-containing heterocycloalkyl, optionally substituted with $(CH_2)_n$-heteroaryl or $(CH_2)_n$-aryl optionally substituted with one or more halogen, where each "n" is independently 0 or 1); or (ii) 1,2,3,4-tetrahydroisoquinoline;

and wherein "aralkyl" or "arylalkyl" refers to a radical in which an aryl group is substituted for a hydrogen of an alkyl group; "heteroarylalkyl" refers to a radical in which a heteroaryl group is substituted for a hydrogen of an alkyl group; "aryl" refers to a monovalent aromatic hydrocarbon group derived by the removal of one hydrogen atom from a single carbon atom of a parent aromatic ring system, and may be monocyclic or a bicyclic fused ring structure where at least one of the rings is an aromatic ring structure; "heteroaryl" refers to a monovalent heteroaromatic group derived by the removal of one hydrogen atom from a single atom of a parent heteroaromatic ring system, and may be a monocyclic group or a bicyclic fused ring structure where at least one of the rings is an aromatic ring structure and at least one of the rings contains a heteroatom; "cycloalkyl" refers to a cyclic hydrocarbyl group having from 3 to 10 carbon atoms, a single cyclic ring or multiple condensed rings, including fused or bridged rings, which are optionally substituted with from 1 to 3 alkyl groups; "heterocycloalkyl" refers to a stable heterocyclic non-aromatic ring and fused rings containing one or more heteroatoms; "hetero" as used as a prefix refers to a structure wherein a carbon atom is replaced by a nitrogen, oxygen or sulfur atom; "heteroatom" refers to a nitrogen, oxygen, or sulfur atom; unless otherwise specified, "substituted" refers to a group in which one or more hydrogen atoms are each independently replaced with the same or different substituents (e.g., halogen, alkyl, aryl, heteroaryl, alkoxy, aryloxy, heteroaryloxy, oxo, hydroxy, thioalkyl, thioaryl, thioheteroaryl, thiol, thioxo, amino, N-alkylamino, N,N-dialkylamino, N-arylamino, N,N-diarylamino, N-heteroarylamino, N,N-diheteroarylamino, N-aryl-N-alkylamino, N-heteroaryl-N-alkylamino, N-aryl-N-heteroarylamino, haloalkyl, trifluoromethyl, cyano, azido, carboxy, alkylsulfonyl, arylsulfonyl, heteroarylsulfonyl, alkylcarbonyl, arylcarbonyl, heteroarylcarbonyl, esters, amides, sulfonamides, and ureas);

or a pharmaceutically acceptable salt, hydrate, solvate or prodrug thereof.

In another embodiment of the present invention, the PDE1 inhibitor is a compound of Formula XXII, selected from the following, in free or salt form:

5-(4-(2-chloro-6-fluorobenzyl)-1,4-diazepan-1-yl)-1-methyl-3-propyl-1H-pyrazolo[4,3-d]pyrimidin-7(6H)-one;

5-((3,4-dichlorobenzyl)(methyl)amino)-1-methyl-3-propyl-1H-pyrazolo[4,3-d]pyrimidin-7(6H)-one;

1-methyl-5-(methyl(4-(piperidin-1-yl)benzyl)amino)-3-propyl-1H-pyrazolo[4,3-d]pyrimidin-7(6H)-one;

5-(dipropylamino)-1-methyl-3-propyl-1H-pyrazolo[4,3-d]pyrimidin-7(6H)-one;

1-methyl-5-(methyl(3-(trifluoromethyl)benzyl)amino)-3-propyl-1H-pyrazolo[4,3-d]pyrimidin-7(6H)-one;

1-methyl-5-(4-(4-methylpiperazin-1-yl)benzylamino)-3-propyl-1H-pyrazolo[4,3-d]pyrimidin-7(6H)-one;

5-(1H-indazol-5-ylamino)-1-methyl-3-propyl-1H-pyrazolo[4,3-d]pyrimidin-7(6H)-one;

5-(3,4-dihydroisoquinolin-2(1H)-yl)-1-methyl-3-propyl-1H-pyrazolo[4,3-d]pyrimidin-7(6H)-one;

5-((4-methoxybenzyl)(methyl)amino)-1-methyl-3-propyl-1H-pyrazolo[4,3-d]pyrimidin-7 (6H)-one;

1-methyl-5-(methyl(3-morpholinobenzyl)amino)-3-propyl-1H-pyrazolo[4,3-d]pyrimidin-7(6H)-one;

1-methyl-5-(3-(piperidin-1-yl)benzylamino)-3-propyl-1H-pyrazolo[4,3-d]pyrimidin-7(6H)-one;

1-methyl-5-(methyl(3-(pyrimidin-5-yl)benzyl)amino)-3-propyl-1H-pyrazolo[4,3-d]pyrimidin-7(6H)-one;

1-methyl-5-(methyl(4-(pyrimidin-5-yl)benzyl)amino)-3-propyl-1H-pyrazolo[4,3-d]pyrimidin-7(6H)-one;

5-(((1,5-dimethyl-1H-pyrazol-3-yl)methyl)(methyl)amino)-1-methyl-3-propyl-1H-pyrazolo[4,3-d]pyrimidin-7 (6H)-one;

5-((3-chlorobenzyl)(methyl)amino)-1-methyl-3-propyl-1H-pyrazolo[4,3-d]pyrimidin-7(6H)-one;

1-methyl-5-(methyl(4-(trifluoromethyl)benzyl)amino)-3-propyl-1H-pyrazolo[4,3-d]pyrimidin-7(6H)-one;

5-((4-chlorobenzyl)(methyl)amino)-1-methyl-3-propyl-1H-pyrazolo[4,3-d]pyrimidin-7(6H)-one;

5-(3-fluorobenzylamino)-1-methyl-3-propyl-1H-pyrazolo[4,3-d]pyrimidin-7(6H)-one;

5-(isopentylamino)-1-methyl-3-propyl-1H-pyrazolo[4,3-d]pyrimidin-7(6H)-one;

5-((3,4-dimethoxyphenethyl)(methyl)amino)-1-methyl-3-propyl-1H-pyrazolo[4,3-d]pyrimidin-7(6H)-one;

5-((4-fluorobenzyl)(methyl)amino)-1-methyl-3-propyl-1H-pyrazolo[4,3-d]pyrimidin-7(6H)-one;

1-methyl-5-(methyl(phenethyl)amino)-3-propyl-1H-pyrazolo[4,3-d]pyrimidin-7(6H)-one;

5-(4-fluorobenzylamino)-1-methyl-3-propyl-1H-pyrazolo[4,3-d]pyrimidin-7(6H)-one;

5-((2-chlorobenzyl)(methyl)amino)-1-methyl-3-propyl-1H-pyrazolo[4,3-d]pyrimidin-7(6H)-one;

1-methyl-5-(methyl((5-phenylisoxazol-3-yl)methyl)amino)-3-propyl-1H-pyrazolo[4,3-d]pyrimidin-7(6H)-one;

1-methyl-3-propyl-5-(3-(pyrrolidin-1-yl)benzylamino)-1H-pyrazolo[4,3-d]pyrimidin-7(6H)-one;

1-methyl-5-(4-(morpholinomethyl)benzylamino)-3-propyl-1H-pyrazolo[4,3-d]pyrimidin-7(6H)-one;

5-(benzyl(isopropyl)amino)-1-methyl-3-propyl-1H-pyrazolo[4,3-d]pyrimidin-7(6H)-one;

5-(diisobutylamino)-1-methyl-3-propyl-1H-pyrazolo[4,3-d]pyrimidin-7(6H)-one;

1-methyl-5-(methyl(propyl)amino)-3-propyl-1H-pyrazolo[4,3-d]pyrimidin-7(6H)-one;

5-(3,5-bis(trifluoromethyl)benzylamino)-1-methyl-3-propyl-1H-pyrazolo[4,3-d]pyrimidin-7(6H)-one;

5-(3,4-dichlorobenzylamino)-1-methyl-3-propyl-1H-pyrazolo[4,3-d]pyrimidin-7(6H)-one;

5-(benzyl(methyl)amino)-1-methyl-3-propyl-1H-pyrazolo[4,3-d]pyrimidin-7(6H)-one;

5-(6-fluoro-3,4-dihydroisoquinolin-2(1H)-yl)-1-methyl-3-propyl-1H-pyrazolo[4,3-d]pyrimidin-7(6H)-one;

1-methyl-5-(methyl((1-methyl-1H-indazol-3-yl)methyl)amino)-3-propyl-1H-pyrazolo[4,3-d]pyrimidin-7(6H)-one;

1-methyl-5-(methyl(thieno[2,3-b]pyridin-2-ylmethyl)amino)-3-propyl-1H-pyrazolo[4,3-d]pyrimidin-7(6H)-one;

5-(6,7-dimethoxy-1-methyl-3,4-dihydroisoquinolin-2(1H)-yl)-1-methyl-3-propyl-1H-pyrazolo[4,3-d]pyrimidin-7(6H)-one;

1-methyl-5-(methyl((1-methyl-3-phenyl-1H-pyrazol-5-yl)methyl)amino)-3-propyl-1H-pyrazolo[4,3-d]pyrimidin-7(6H)-one;

1-methyl-5-(methyl((2-(4-(trifluoromethyl)phenyl)thiazol-4-yl)methyl)amino)-3-propyl-1H-pyrazolo[4,3-d]pyrimidin-7(6H)-one;

1-methyl-5-(methyl(4-(pyridin-4-yl)benzyl)amino)-3-propyl-1H-pyrazolo[4,3-d]pyrimidin-7(6H)-one;

1-methyl-5-(methyl((2-(pyrrolidin-1-yl)pyridin-4-yl)methyl)amino)-3-propyl-1H-pyrazolo[4,3-d]pyrimidin-7(6H)-one;

1-methyl-5-(methyl((6-morpholinopyridin-2-yl)methyl)amino)-3-propyl-1H-pyrazolo[4,3-d]pyrimidin-7(6H)-one;

1-methyl-5-(methyl(3-(pyridin-4-yl)benzyl)amino)-3-propyl-1H-pyrazolo[4,3-d]pyrimidin-7(6H)-one;

1-methyl-5-(methyl(4-(pyridin-2-yl)benzyl)amino)-3-propyl-1H-pyrazolo[4,3-d]pyrimidin-7(6H)-one;

5-((3,4-dichlorobenzyl)(isopentyl)amino)-1-methyl-3-propyl-1H-pyrazolo[4,3-d]pyrimidin-7(6H)-one;

5-(butyl(3,4-dichlorobenzyl)amino)-1-methyl-3-propyl-1H-pyrazolo[4,3-d]pyrimidin-7(6H)-one;

1-methyl-5-(methyl((4-methyl-2-phenylthiazol-5-yl)methyl)amino)-3-propyl-1H-pyrazolo[4,3-d]pyrimidin-7(6H)-one;

1-methyl-5-(methyl(3-(2-morpholinoethoxy)benzyl)amino)-3-propyl-1H-pyrazolo[4,3-d]pyrimidin-7(6H)-one;

1-methyl-5-(methyl(4-(2-morpholinoethoxy)benzyl)amino)-3-propyl-1H-pyrazolo[4,3-d]pyrimidin-7(6H)-one;

1-methyl-5-(2-(2-morpholinoethoxy)benzylamino)-3-propyl-1H-pyrazolo[4,3-d]pyrimidin-7(6H)-one;

1-methyl-5-(((5-methyl-3-phenylisoxazol-4-yl)methyl)amino)-3-propyl-1H-pyrazolo[4,3-d]pyrimidin-7(6H)-one;

1-methyl-5-(((5-methyl-2-phenyl-2H-1,2,3-triazol-4-yl)methylamino)-3-propyl-1H-pyrazolo[4,3-d]pyrimidin-7(6H)-one;

1-methyl-5-(3-(morpholinomethyl)benzylamino)-3-propyl-1H-pyrazolo[4,3-d]pyrimidin-7 (6H)-one;

1-methyl-5-((2-morpholinopyridin-4-yl)methylamino)-3-propyl-1H-pyrazolo[4,3-d]pyrimidin-7 (6H)-one;

1-methyl-5-(3-(2-morpholinoethoxy)benzylamino)-3-propyl-1H-pyrazolo[4,3-d]pyrimidin-7 (6H)-one;

1-methyl-5-(3-morpholinobenzylamino)-3-propyl-1H-pyrazolo[4,3-d]pyrimidin-7(6H)-one;

1-methyl-5-((1-phenyl-1H-pyrazol-3-yl)methylamino)-3-propyl-1H-pyrazolo[4,3-d]pyrimidin-7 (6H)-one;

1-methyl-5-(methyl(naphthalen-1-ylmethyl)amino)-3-propyl-1H-pyrazolo[4,3-d]pyrimidin-7 (6H)-one;

5-(4-(2,2-diphenylacetoyl)piperazin-1-yl)-1-methyl-3-propyl-1H-pyrazolo[4,3-d]pyrimidin-7 (6H)-one;

1-methyl-3-propyl-5-(4-(trifluoromethyl)piperidin-1-yl)-1H-pyrazolo[4,3-d]pyrimidin-7 (6H)-one;

1-methyl-5-(methyl(4-morpholinobenzyl)amino)-3-propyl-1H-pyrazolo[4,3-d]pyrimidin-7(6H)-one;

5-((2,3-dihydrobenzofuran-5-yl)methylamino)-1-methyl-3-propyl-1H-pyrazolo[4,3-d]pyrimidin-7(6H)-one;

5-(1H-pyrazol-1-yl)benzylamino)-1-methyl-3-propyl-1H-pyrazolo[4,3-d]pyrimidin-7(6H)-one;

5-(1H-pyrrol-1-yl)benzylamino)-1-methyl-3-propyl-1H-pyrazolo[4,3-d]pyrimidin-7(6H)-one;

1-methyl-5-(methyl(3-(2-methylthiazol-4-yl)benzyl)amino)-3-propyl-1H-pyrazolo[4,3-d]pyrimidin-7(6H)-one;

1-methyl-5-((1-methyl-3-phenyl-1H-pyrazol-5-yl)methylamino)-3-propyl-1H-pyrazolo[4,3-d]pyrimidin-7(6H)-one;

1-methyl-5-(methyl-1H-pyrazol-3-yl)benzylamino)-3-propyl-1H-pyrazolo[4,3-d]pyrimidin-7 (6H)-one;

1-methyl-5-((1-methyl-1H-indol-5-yl)methylamino)-3-propyl-1H-pyrazolo[4,3-d]pyrimidin-7(6H)-one;

1-methyl-5-((1-methyl-1H-indol-6-yl)methylamino)-3-propyl-1H-pyrazolo[4,3-d]pyrimidin-7(6H)-one;

3-cyclopentyl-5-((4-fluorobenzyl)(methyl)amino)-1-methyl-1H-pyrazolo[4,3-d]pyrimidin-7 (6H)-one;

5-((4-chlorobenzyl)(methyl)amino)-3-cyclopentyl-1-methyl-1H-pyrazolo[4,3-d]pyrimidin-7 (6H)-one;

1-methyl-5-((4-methyl-2-phenylthiazol-5-yl)methylamino)-3-propyl-1H-pyrazolo[4,3-d]pyrimidin-7(6H)-one;

5-(1H-1,2,4-triazol-1-yl)benzylamino)-1-methyl-3-propyl-1H-pyrazolo[4,3-d]pyrimidin-7 (6H)-one;

5-(isobutyl(3-morpholinobenzyl)amino)-1-methyl-3-propyl-1H-pyrazolo[4,3-d]pyrimidin-7(6H)-one;

5-((4-chlorophenethyl)(propyl)amino)-1-methyl-3-propyl-1H-pyrazolo[4,3-d]pyrimidin-7(6H)-one;

3-cyclopentyl-5-(3,4-dichlorobenzylamino)-1-methyl-1H-pyrazolo[4,3-d]pyrimidin-7 (6H)-one;

3-cyclopentyl-5-((3,4-dichlorobenzyl)(methyl)amino)-1-methyl-1H-pyrazolo[4,3-d]pyrimidin-7 (6H)-one;

3-cyclopentyl-5-(dipropylamino)-1-methyl-1H-pyrazolo[4,3-d]pyrimidin-7(6H)-one;

5-(4-chlorophenethylamino)-1-methyl-3-propyl-1H-pyrazolo[4,3-d]pyrimidin-7(6H)-one;

3-tert-butyl-1-methyl-5-(methyl((4-methyl-2-phenylthiazol-5-yl)methyl)amino)-1H-pyrazolo[4,3-d]pyrimidin-7 (6H)-one;

3-tert-butyl-1-methyl-5-(methyl((1-methyl-3-phenyl-1H-pyrazol-5-yl)methyl)amino)-1H-pyrazolo[4,3-d]pyrimidin-7(6H)-one;

5-(3,4-diethoxyphenethylamino)-1-methyl-3-propyl-1H-pyrazolo[4,3-d]pyrimidin-7(6H)-one;

5-([1,2,4]triazolo[4,3-a]pyridin-3-ylmethylamino)-1-methyl-3-propyl-1H-pyrazolo[4,3-d]pyrimidin-7(6H)-one;

3-cyclopentyl-1-methyl-5-(2-methylpiperidin-1-yl)-1H-pyrazolo[4,3-d]pyrimidin-7(6H)-one;

3-cyclopentyl-1-methyl-5-(piperidin-1-yl)-1H-pyrazolo[4,3-d]pyrimidin-7(6H)-one;

3-cyclopentyl-1-methyl-5-(2-phenylpyrrolidin-1-yl)-1H-pyrazolo[4,3-d]pyrimidin-7(6H)-one;

5-(4-fluorophenethylamino)-1-methyl-3-propyl-1H-pyrazolo[4,3-d]pyrimidin-7(6H)-one;

1-methyl-5-(2-(1-phenyl-1H-pyrazol-4-yl)ethylamino)-3-propyl-1H-pyrazolo[4,3-d]pyrimidin-7(6H)-one;

3-tert-butyl-5-(dipropylamino)-1-methyl-1H-pyrazolo[4,3-d]pyrimidin-7(6H)-one;

3-tert-butyl-1-methyl-5-(methyl(3-(2-methylthiazol-4-yl)benzyl)amino)-1H-pyrazolo[4,3-d]pyrimidin-7(6H)-one;

5-((1-benzyl-3,5-dimethyl-1H-pyrazol-4-yl)methylamino)-1-methyl-3-propyl-1H-pyrazolo[4,3-d]pyrimidin-7(6H)-one;

3-tert-butyl-1-methyl-5-(3-(4-methylpiperazin-1-yl)benzylamino)-1H-pyrazolo[4,3-d]pyrimidin-7 (6H)-one;
5-((1H-pyrazol-1-yl)benzyl)(isobutyl)amino)-3-tert-butyl-1-methyl-1H-pyrazolo[4,3-d]pyrimidin-7(6H)-one;
5-((1H-pyrazol-1-yl)benzyl)(isobutyl)amino)-1-methyl-3-propyl-1H-pyrazolo[4,3-d]pyrimidin-7 (6H)-one;
5-((1H-1,2,4-triazol-1-yl)benzyl)(isobutyl)amino)-3-tert-butyl-1-methyl-1H-pyrazolo[4,3-d]pyrimidin-7(6H)-one;
5-((1H-1,2,4-triazol-1-yl)benzyl)(isobutyl)amino)-1-methyl-3-propyl-1H-pyrazolo[4,3-d]pyrimidin-7(6H)-one;
3-tert-butyl-5-((4-fluorobenzyl)(isobutyl)amino)-1-methyl-1H-pyrazolo[4,3-d]pyrimidin-7 (6H)-one;
5-((4-fluorobenzyl)(isobutyl)amino)-1-methyl-3-propyl-1H-pyrazolo[4,3-d]pyrimidin-7 (6H)-one;
3-tert-butyl-5-(isobutyl(methyl)amino)-1-methyl-1H-pyrazolo[4,3-d]pyrimidin-7(6H)-one;
5-((1H-pyrrol-1-yl)benzyl)(isobutyl)amino)-3-tert-butyl-1-methyl-1H-pyrazolo[4,3-d]pyrimidin-7 (6H)-one;
5-((1H-pyrrol-1-yl)benzyl)(isobutyl)amino)-1-methyl-3-propyl-1H-pyrazolo[4,3-d]pyrimidin-7(6H)-one;
5-(isobutyl(3-(4-methylpiperazin-1-yl)benzyl)amino)-1-methyl-3-propyl-1H-pyrazolo[4,3-d]pyrimidin-7(6H)-one;
3-tert-butyl-5-((3,3-dimethylbutyl)(3-morpholinobenzyl)amino)-1-methyl-1H-pyrazolo[4,3-d]pyrimidin-7(6H)-one;
3-tert-butyl-1-methyl-5-((2-methylpentyl)(3-morpholinobenzyl)amino)-1H-pyrazolo[4,3-d]pyrimidin-7 (6H)-one;
3-tert-butyl-5-((2-ethylbutyl)(methyl)amino)-1-methyl-1H-pyrazolo[4,3-d]pyrimidin-7 (6H)-one;
5-((1H-pyrazol-1-yl)benzyl)(isopentyl)amino)-1-methyl-3-propyl-1H-pyrazolo[4,3-d]pyrimidin-7 (6H)-one;
5-((1H-pyrazol-1-yl)benzyl)(2-ethylbutyl)amino)-1-methyl-3-propyl-1H-pyrazolo[4,3-d]pyrimidin-7(6H)-one;
5-((3,3-dimethylbutyl)(3-morpholinobenzyl)amino)-1-methyl-3-propyl-1H-pyrazolo[4,3-d]pyrimidin-7(6H)-one;
3-tert-butyl-5-((2-ethylbutyl)(3-morpholinobenzyl)amino)-1-methyl-1H-pyrazolo[4,3-d]pyrimidin-7(6H)-one;
5-((3,3-dimethylbutyl)(methyl)amino)-1-methyl-3-propyl-1H-pyrazolo[4,3-d]pyrimidin-7 (6H)-one;
3-tert-butyl-5-((3,3-dimethylbutyl)(methyl)amino)-1-methyl-1H-pyrazolo[4,3-d]pyrimidin-7 (6H)-one;
1-methyl-5-(methyl(2-methylbutyl)amino)-3-propyl-1H-pyrazolo[4,3-d]pyrimidin-7(6H)-one;
1-methyl-5-((2-methylpentyl)(3-morpholinobenzyl)amino)-3-propyl-1H-pyrazolo[4,3-d]pyrimidin-7(6H)-one;
1-methyl-5-((2-methylbutyl)(3-morpholinobenzyl)amino)-3-propyl-1H-pyrazolo[4,3-d]pyrimidin-7(6H)-one;
3-tert-butyl-1-methyl-5-(methyl(2-methylpentyl)amino)-1H-pyrazolo[4,3-d]pyrimidin-7 (6H)-one;
5-((1H-1,2,4-triazol-1-yl)benzyl)(2-methylbutyl)amino)-1-methyl-3-propyl-1H-pyrazolo[4,3-d]pyrimidin-7(6H)-one;
3-tert-butyl-1-methyl-5-((2-methylbutyl)(3-morpholinobenzyl)amino)-1H-pyrazolo[4,3-d]pyrimidin-7(6H)-one;
5-((1H-1,2,4-triazol-1-yl)benzyl)(2-methylbutyl)amino)-3-tert-butyl-1-methyl-1H-pyrazolo[4,3-d]pyrimidin-7(6H)-one;
5-((1H-pyrazol-1-yl)benzyl)(neopentyl)amino)-1-methyl-3-propyl-1H-pyrazolo[4,3-d]pyrimidin-7(6H)-one;
4-((1-methyl-7-oxo-3-propyl-6,7-dihydro-1H-pyrazolo[4,3-d]pyrimidin-5-ylamino)methyl)benzenesulfonamide;
5-((1H-pyrazol-1-yl)benzyl)(2-ethylbutyl)amino)-3-tert-butyl-1-methyl-1H-pyrazolo[4,3-d]pyrimidin-7(6H)-one;
5-((1H-pyrazol-1-yl)benzyl)(2-methylpentyl)amino)-3-tert-butyl-1-methyl-1H-pyrazolo[4,3-d]pyrimidin-7(6H)-one;
1-methyl-5-(methyl(2-methylpentyl)amino)-3-propyl-1H-pyrazolo[4,3-d]pyrimidin-7(6H)-one;
3-tert-butyl-1-ethyl-5-(isobutyl(3-morpholinobenzyl)amino)-1H-pyrazolo[4,3-d]pyrimidin-7(6H)-one; and
3-cyclopropyl-5-(dipropylamino)-1-methyl-1H-pyrazolo[4,3-d]pyrimidin-7 (6H)-one.

In another embodiment of the present invention, the PDE1 inhibitor is a compound of Formula XXIII:

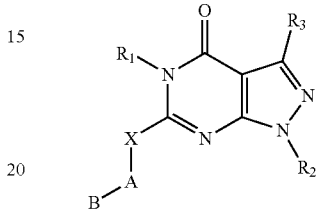

Formula XXIII wherein,
A represents a bond, —(CH$_2$)$_n$—, —CO, —CONR$^4$—, —CSNR$^4$—, —C(=N—CN)NR$^4$—, C(=CH—NO$_2$)NR$^4$, —COO—, —SO$_2$—, or —SO$_2$NR$^4$—, aryl or heteroaryl, optionally substituted with one or more groups selected from halogen, CF$_3$, C$_1$-C$_6$ alkyl, C$_1$-C$_6$ alkyl-cycloalkyl, cycloalkyl, heterocycloalkyl —SO$_2$R$^4$— and C$_1$-C$_6$ alkyl-heterocycloalkyl, where A is linked to X via a nitrogen atom within the X group;
B represents bond, C$_1$-C$_6$ alkyl, (CH$_2$)$_m$-cycloalkyl, —(CH$_2$)$_m$-heterocycloalkyl, (CH$_2$)$_m$-aryl or (CH$_2$)$_m$-heteroaryl optionally substituted with one or more groups selected from halogen, CN, CF$_3$, NR$^4$R$^5$, NR$^5$COR$^4$, CONR$^4$R$^5$, NR$^5$SO2R$^4$, SO$_2$NR$^4$R$^5$, C$_1$-C$_6$ alkyl, (CH$_2$)$_n$-heterocycloalkyl (optionally substituted by C$_1$-C$_6$ alkyl), N$_2$, OR$^4$, COR$^4$, CO$_2$R$^4$, or SO$_2$R$^4$
X represents a carbon-carbon bonded nitrogen-containing heterocycloalkyl group;
R$^1$ represents H, C$_1$-C$_6$ alkyl, (CH$_2$)$_n$-aryl, cycloalkyl or —C$_1$-C$_6$ alkyl-cycloalkyl group, each of which may optionally be substituted with one or more groups selected from halogen, CN, CF$_3$, NR$^4$R$^5$, NHCOR$^4$, CONH$_2$, NHSO$_2$R$^4$, SO$_2$NHR$^4$, C$_1$-C$_6$ alkyl, C$_1$-C$_6$ alkoxy, COR$^4$, CO$_2$R$^4$, or SO$_2$R$^4$;
R$^2$ represents H, C$_1$-C$_6$ alkyl, cycloalkyl, heterocycloalkyl, (CH$_2$)$_n$-aryl, or a (CH$_2$)$_n$-heteroaryl group, each of which may optionally be substituted with one or more groups selected from halogen, CN, CF$_3$, NR$^4$R$^5$, NHCOR$^4$, CONH$_2$, NHSO$_2$R$^4$, SO$_2$NHR$^4$, SO$_2$R$^4$, C$_1$-C$_6$ alkyl, OR$^4$, COR$^4$, CO$_2$R$^4$, or SO$_2$R$^4$;
R$^3$ represents H, halogen, C$_1$-C$_6$ alkyl, cycloalkyl, (CH$_2$)$_n$-aryl, aryl, or a heteroaryl group, each of which may optionally be substituted with one or more groups selected from halogen, CN, CF$_3$, NR$^4$R$^5$, NHCOR$^4$, CONH$_2$, NHSO$_2$R$^4$, SO$_2$NHR$^4$, SO$_2$R$^4$, C$_1$-C$_6$ alkyl, C$_1$-C$_6$ alkoxy, COR$^4$, CO$_2$R$^4$, or SO$_2$R$^4$;
each R$^4$ independently represents H, C$_1$-C$_6$ alkyl, cycloalkyl, heterocycloalkyl, CF$_3$ or CHF$_2$;
R$^5$ represents H, C$_1$-C$_6$ alkyl, or cycloalkyl;
each "n" independently represents 0,1, 2 or 3;
each "m" represents 0, 1, 2, 3, 4, 5 or 6;

and wherein the term "aralkyl" or "arylalkyl" refers to a radical in which an aryl group is substituted for a hydrogen of an alkyl group; "heteroarylalkyl" refers to a radical in which a heteroaryl group is substituted for a hydrogen of an alkyl group; "aryl" refers to a monovalent aromatic hydrocarbon group derived by the removal of one hydrogen atom from a single carbon atom of a parent aromatic ring system, and may be monocyclic or a bicyclic fused ring structure where at least one of the rings is an aromatic ring structure; "heteroaryl" refers to a monovalent heteroaromatic group derived by the removal of one hydrogen atom from a single atom of a parent heteroaromatic ring system, and may be a monocyclic group or a bicyclic fused ring structure where at least one of the rings is an aromatic ring structure and at least one of the rings contains a heteroatom; "cycloalkyl refers to a cyclic hydrocarbyl group having from 3 to 10 carbon atoms, a single cyclic ring or multiple condensed rings, including fused or bridged rings, which are optionally substituted with from 1 to 3 alkyl groups; "heterocycloalkyl" refers to a stable heterocyclic non-aromatic ring and fused rings containing one or more heteroatoms; "hetero" as used as a prefix refers to a structure wherein a carbon atom is replaced by a nitrogen, oxygen or sulfur atom; "heteroatom" refers to a nitrogen, oxygen, or sulfur atom; unless otherwise specified, "substituted" refers to a group in which one or more hydrogen atoms are each independently replaced with the same or different substituents (e.g., halogen, alkyl, aryl, heteroaryl, alkoxy, aryloxy, heteroaryloxy, oxo, hydroxy, thioalkyl, thioaryl, thioheteroaryl, thiol, thioxo, amino, N-alkylamino, N,N-dialkylamino, N-arylamino, N,N-diarylamino, N-heteroarylamino, N,N-diheteroarylamino, N-aryl-N-alkylamino, N-heteroaryl-N-alkylamino, N-aryl-N-heteroarylamino, haloalkyl, trifluoromethyl, cyano, azido, carboxy, alkylsulfonyl, arylsulfonyl, heteroarylsulfonyl, alkylcarbonyl, arylcarbonyl, heteroarylcarbonyl, esters, amides, sulfonamides, and ureas);

in free form or as a pharmaceutically acceptable salt, hydrate, solvate or prodrug thereof.

In another embodiment of the present invention, the PDE1 inhibitor is a compound of Formula XXIII selected from:

N-(benzo[d][1,3]dioxol-5-yl)-3-(1-tert-butyl-3-methyl-4-oxo-4,5-dihydro-1H-pyrazolo[3,4-d]pyrimidin-6-yl)azetidine-1-carboxamide;
3-(1-cyclohexyl-4-oxo-4,5-dihydro-1H-pyrazolo[3,4-d]pyrimidin-6-yl)-N-(4-(4-isopropylpiperazin-1-yl)phenyl)azetidine-1-carboxamide;
3-(1-cyclohexyl-4-oxo-4,5-dihydro-1H-pyrazolo[3,4-d]pyrimidin-6-yl)-N-(4-(4-methylpiperazin-1-yl)phenyl)azetidine-1-carboxamide;
3-(1-cyclohexyl-4-oxo-4,5-dihydro-1H-pyrazolo[3,4-d]pyrimidin-6-yl)-N-(3,4-dimethylphenyl)azetidine-1-carboxamide;
3-(1-cyclohexyl-4-oxo-4,5-dihydro-1H-pyrazolo[3,4-d]pyrimidin-6-yl)-N-(cyclohexylmethyl)azetidine-1-carboxamide;
3-(1-tert-butyl-3-methyl-4-oxo-4,5-dihydro-1H-pyrazolo[3,4-d]pyrimidin-6-yl)-N-phenylazetidine-1-carboxamide;
3-(1-cyclohexyl-4-oxo-4,5-dihydro-1H-pyrazolo[3,4-d]pyrimidin-6-yl)-N-(3-(dimethylamino)phenyl)azetidine-1-carboxamide;
N-(3-chlorophenyl)-3-(1-cyclohexyl-4-oxo-4,5-dihydro-1H-pyrazolo[3,4-d]pyrimidin-6-yl)azetidine-1-carboxamide;
3-(1-cyclohexyl-4-oxo-4,5-dihydro-1H-pyrazolo[3,4-d]pyrimidin-6-yl)-N-(4-(dimethylamino)phenyl)azetidine-1-carboxamide;
3-(1-cyclohexyl-4-oxo-4,5-dihydro-1H-pyrazolo[3,4-d]pyrimidin-6-yl)-N-(4-morpholinophenyl)azetidine-1-carboxamide;
3-(1-cyclohexyl-4-oxo-4,5-dihydro-1H-pyrazolo[3,4-d]pyrimidin-6-yl)-N-phenylazetidine-1-carboxamide;
3-(1-tert-butyl-3-methyl-4-oxo-4,5-dihydro-1H-pyrazolo[3,4-d]pyrimidin-6-yl)-N-(4-fluorophenyl)azetidine-1-carboxamide;
3-(1-cyclohexyl-4-oxo-4,5-dihydro-1H-pyrazolo[3,4-d]pyrimidin-6-yl)-N-(4-methoxyphenyl)azetidine-1-carboxamide;
3-(1-cyclohexyl-3-methyl-4-oxo-4,5-dihydro-1H-pyrazolo[3,4-d]pyrimidin-6-yl)-N-phenylazetidine-1-carboxamide;
3-(1-tert-butyl-3-methyl-4-oxo-4,5-dihydro-1H-pyrazolo[3,4-d]pyrimidin-6-yl)-N-cyclohexylazetidine-1-carboxamide;
3-(1-tert-butyl-4-oxo-4,5-dihydro-1H-pyrazolo[3,4-d]pyrimidin-6-yl)-N-(4-fluorophenyl)azetidine-1-carboxamide;
3-(1-tert-butyl-3-methyl-4-oxo-4,5-dihydro-1H-pyrazolo[3,4-d]pyrimidin-6-yl)-N-(4-fluorobenzyl)azetidine-1-carboxamide;
3-(1-cyclohexyl-4-oxo-4,5-dihydro-1H-pyrazolo[3,4-d]pyrimidin-6-yl)-N-(4-isopropylphenyl)azetidine-1-carboxamide;
3-(1-cyclohexyl-4-oxo-4,5-dihydro-1H-pyrazolo[3,4-d]pyrimidin-6-yl)-N-(4-fluorophenyl)azetidine-1-carboxamide;
3-(1-cyclohexyl-4-oxo-4,5-dihydro-1H-pyrazolo[3,4-d]pyrimidin-6-yl)-N-(3,4-difluorophenyl)azetidine-1-carboxamide;
3-(1-cyclohexyl-3-methyl-4-oxo-4,5-dihydro-1H-pyrazolo[3,4-d]pyrimidin-6-yl)-N-(4-fluorophenyl)azetidine-1-carboxamide;
N-benzyl-3-(1-tert-butyl-3-methyl-4-oxo-4,5-dihydro-1H-pyrazolo[3,4-d]pyrimidin-6-yl)azetidine-1-carboxamide;
N-cyclohexyl-3-(1-cyclohexyl-4-oxo-4,5-dihydro-1H-pyrazolo[3,4-d]pyrimidin-6-yl)azetidine-1-carboxamide;
N-benzyl-3-(1-cyclohexyl-3-methyl-4-oxo-4,5-dihydro-1H-pyrazolo[3,4-d]pyrimidin-6-yl)azetidine-1-carboxamide;
3-(1-cyclohexyl-4-oxo-4,5-dihydro-1H-pyrazolo[3,4-d]pyrimidin-6-yl)-N-(4-(trifluoromethoxy)phenyl)azetidine-1-carboxamide;
tert-butyl 3-(3-(1-cyclohexyl-4-oxo-4,5-dihydro-1H-pyrazolo[3,4-d]pyrimidin-6-yl)azetidine-1-carboxamido)piperidine-1-carboxylate;
3-(1-cyclohexyl-3-methyl-4-oxo-4,5-dihydro-1H-pyrazolo[3,4-d]pyrimidin-6-yl)-N-(4-fluorobenzyl)azetidine-1-carboxamide;
3-(1-cyclohexyl-3-methyl-4-oxo-4,5-dihydro-1H-pyrazolo[3,4-d]pyrimidin-6-yl)-N-(4-methoxybenzyl)azetidine-1-carboxamide;
N-(2-(difluoromethoxy)phenyl)-3-(1-(4-fluorophenyl)-3-methyl-4-oxo-4,5-dihydro-1H-pyrazolo[3,4-d]pyrimidin-6-yl)azetidine-1-carboxamide;
3-(1-cyclohexyl-4-oxo-4,5-dihydro-1H-pyrazolo[3,4-d]pyrimidin-6-yl)-N-(4-fluorobenzyl)azetidine-1-carboxamide;
N-benzyl-3-(1-cyclohexyl-4-oxo-4,5-dihydro-1H-pyrazolo[3,4-d]pyrimidin-6-yl)azetidine-1-carboxamide;

3-(1-cyclohexyl-4-oxo-4,5-dihydro-1H-pyrazolo[3,4-d]pyrimidin-6-yl)-N-cyclopentylazetidine-1-carboxamide;
N-(4-cyanophenyl)-3-(1-cyclohexyl-4-oxo-4,5-dihydro-1H-pyrazolo[3,4-d]pyrimidin-6-yl)azetidine-1-carboxamide;
N-butyl-3-(1-cyclohexyl-4-oxo-4,5-dihydro-1H-pyrazolo[3,4-d]pyrimidin-6-yl)azetidine-1-carboxamide;
3-(1-cyclohexyl-4-oxo-4,5-dihydro-1H-pyrazolo[3,4-d]pyrimidin-6-yl)-N-(4-(trifluoromethyl)phenyl)azetidine-1-carboxamide;
3-(1-cyclohexyl-4-oxo-4,5-dihydro-1H-pyrazolo[3,4-d]pyrimidin-6-yl)-N-(3,4-dichlorobenzyl)azetidine-1-carboxamide;
N-tert-butyl-3-(1-cyclohexyl-4-oxo-4,5-dihydro-1H-pyrazolo[3,4-d]pyrimidin-6-yl)azetidine-1-carboxamide;
3-(1-cyclohexyl-3-methyl-4-oxo-4,5-dihydro-1H-pyrazolo[3,4-d]pyrimidin-6-yl)-N-(3,4-dichlorobenzyl)azetidine-1-carboxamide;
3-(1-cyclohexyl-4-oxo-4,5-dihydro-1H-pyrazolo[3,4-d]pyrimidin-6-yl)-N-(1-(methylsulfonyl)piperidin-4-yl)azetidine-1-carboxamide;
tert-butyl 4-(3-(1-cyclohexyl-4-oxo-4,5-dihydro-1H-pyrazolo[3,4-d]pyrimidin-6-yl)azetidine-1-carboxamido)piperidine-1-carboxylate;
(S)-3-(1-cyclohexyl-3-methyl-4-oxo-4,5-dihydro-1H-pyrazolo[3,4-d]pyrimidin-6-yl)-N-(1-phenylethyl)azetidine-1-carboxamide;
3-(1-cyclohexyl-4-oxo-4,5-dihydro-1H-pyrazolo[3,4-d]pyrimidin-6-yl)-N-(3,3,3-trifluoropropyl)azetidine-1-carboxamide;
1-cyclohexyl-6-(1-(3,4-dimethoxyphenylsulfonyl)piperidin-3-yl)-1H-pyrazolo[3,4-d]pyrimidin-4(5H)-one;
4-(4-isopropylpiperazin-1-yl)phenyl 3-(1-tert-butyl-4-oxo-4,5-dihydro-1H-pyrazolo[3,4-d]pyrimidin-6-yl)azetidine-1-carboxylate;
cyclohexylmethyl 3-(1-tert-butyl-4-oxo-4,5-dihydro-1H-pyrazolo[3,4-d]pyrimidin-6-yl)azetidine-1-carboxylate;
3-chlorophenyl 3-(1-tert-butyl-4-oxo-4,5-dihydro-1H-pyrazolo[3,4-d]pyrimidin-6-yl)azetidine-1-carboxylate;
benzo[d][1,3]dioxol-5-yl 3-(1-tert-butyl-4-oxo-4,5-dihydro-1H-pyrazolo[3,4-d]pyrimidin-6-yl)azetidine-1-carboxylate;
cyclohexylmethyl 3-(1-cyclohexyl-4-oxo-4,5-dihydro-1H-pyrazolo[3,4-d]pyrimidin-6-yl)azetidine-1-carboxylate;
4-fluorophenyl 3-(1-cyclohexyl-4-oxo-4,5-dihydro-1H-pyrazolo[3,4-d]pyrimidin-6-yl)azetidine-1-carboxylate;
6-(1-(1H-benzo[d]imidazol-2-yl)azetidin-3-yl)-1-cyclohexyl-1H-pyrazolo[3,4-d]pyrimidin-4(5H)-one;
6-(1-(6-bromo-1H-benzo[d]imidazol-2-yl)azetidin-3-yl)-1-tert-butyl-1H-pyrazolo[3,4-d]pyrimidin-4(5H)-one;
1-tert-butyl-6-(1-(5-(trifluoromethyl)-1H-benzo[d]imidazol-2-yl)azetidin-3-yl)-1H-pyrazolo[3,4-d]pyrimidin-4(5H)-one;
6-(1-(1H-benzo[d]imidazol-2-yl)azetidin-3-yl)-1-tert-butyl-1H-pyrazolo[3,4-d]pyrimidin-4(5H)-one;
1-cyclohexyl-6-(1-(4-phenyloxazol-2-yl)azetidin-3-yl)-1H-pyrazolo[3,4-d]pyrimidin-4(5H)-one;
1-cyclohexyl-6-(1-(4-(morpholinosulfonyl)phenyl)azetidin-3-yl)-1H-pyrazolo[3,4-d]pyrimidin-4(5H)-one;
6-(1-(3-amino-4-nitrophenyl)azetidin-3-yl)-1-cyclohexyl-1H-pyrazolo[3,4-d]pyrimidin-4(5H)-one;
6-(1-(4-acetylphenyl)azetidin-3-yl)-1-cyclohexyl-1H-pyrazolo[3,4-d]pyrimidin-4(5H)-one;
4-(3-(1-cyclohexyl-4-oxo-4,5-dihydro-1H-pyrazolo[3,4-d]pyrimidin-6-yl)azetidin-1-yl)benzonitrile;
1-cyclohexyl-6-(1-(3-methyl-4-nitrophenyl)azetidin-3-yl)-1H-pyrazolo[3,4-d]pyrimidin-4(5H)-one;
1-cyclohexyl-6-(1-(4-(morpholinomethyl)phenyl)azetidin-3-yl)-1H-pyrazolo[3,4-d]pyrimidin-4(5H)-one;
1-cyclohexyl-6-(1-(5-phenyl-4H-1,2,4-triazol-3-yl)azetidin-3-yl)-1H-pyrazolo[3,4-d]pyrimidin-4(5H)-one;
1-cyclohexyl-6-(1-(4-phenylthiazol-2-yl)azetidin-3-yl)-1H-pyrazolo[3,4-d]pyrimidin-4(5H)-one;
1-cyclohexyl-6-(1-(4-(4-(4-isopropylpiperazin-1-yl)phenyl)thiazol-2-yl)azetidin-3-yl)-1H-pyrazolo[3,4-d]pyrimidin-4(5H)-one;
1-cyclohexyl-6-(1-(5-(morpholinomethyl)-4-phenylthiazol-2-yl)azetidin-3-yl)-1H-pyrazolo[3,4-d]pyrimidin-4(5H)-one;
1-tert-butyl-6-(1-(4-(morpholinomethyl)phenyl)azetidin-3-yl)-1H-pyrazolo[3,4-d]pyrimidin-4(5H)-one;
(Z)-N'-cyano-3-(1-cyclohexyl-4-oxo-4,5-dihydro-1H-pyrazolo[3,4-d]pyrimidin-6-yl)-N-(4-fluorophenyl)azetidine-1-carboximidamide;
(Z)-N'-cyano-3-(1-cyclohexyl-4-oxo-4,5-dihydro-1H-pyrazolo[3,4-d]pyrimidin-6-yl)-N-(cyclohexylmethyl)azetidine-1-carboximidamide; and
(Z)-3-(1-tert-butyl-4-oxo-4,5-dihydro-1H-pyrazolo[3,4-d]pyrimidin-6-yl)-N'-cyano-N-(4-fluorophenyl)azetidine-1-carboximidamide;
or a pharmaceutically acceptable salts thereof.

NEP Inhibitors

In one embodiment, the NEP inhibitors for use in the current invention are selective NEP inhibitors. In a further embodiment, the NEP inhibitors for use in the current invention are inhibitors with at least 300-fold selectivity for NEP inhibition over ACE inhibition. In a further embodiment, the NEP inhibitors for use in the current invention are inhibitors with at least 100-fold selectivity for NEP inhibition over ECE (Endothelin Converting Enzyme) inhibition. In yet another embodiment, the NEP inhibitors for use in the current invention are inhibitors with at least 300-fold selectivity for NEP inhibition over ACE inhibition and 100-fold selectivity for NEP inhibition over ECE inhibition.

In another embodiment, the NEP inhibitors for use in the current invention are the NEP inhibitors disclosed in the following patents, patent applications or non-patent publications: EP-1097719 B1, EP-509442A, U.S. Pat. No. 4,929,641, EP-599444B, US-798684, *J. Med. Chem.* (1993) 3821, EP-136883, U.S. Pat. No. 4,722,810, *Curr. Pharm. Design* (1996) 443, *J. Med. Chem.* (1993) 87, EP-830863, EP-733642, WO 9614293, WO 9415908, WO 9309101, WO 9109840, EP-519738, EP-690070, *Bioorg. Med. Chem. Lett.* (1996) 65, EP-A-0274234, *Biochem. Biophys. Res. Comm.* (1989) 58, *Perspect. Med. Chem.* (1993) 45, or EP-358398-B. The contents of these patents and publications are hereby incorporated by reference in their entirety herein. In another embodiment, the NEP inhibitors for use in the current invention are the NEP inhibitors Phosphoramidon, Thiorphan, Candoxatrilat, Candoxatril, or the compound of the Chemical Abstract Service (CAS) Number 115406-23-0.

In another embodiment, the NEP inhibitors for use in the current invention are the NEP inhibitors disclosed in US 2006/0041014 A1, the contents of which are hereby incorporated by reference in their entirety herein.

In another embodiment, the NEP inhibitors for use in the current invention are the NEP inhibitors disclosed in U.S. Pat. No. 5,217,996, the contents of which are hereby incorporated by reference in their entirety herein.

In another embodiment, the NEP inhibitors for use in the current invention are the NEP inhibitors disclosed in U.S. Pat. No. 8,513,244, the contents of which are hereby incorporated by reference in their entirety herein.

In another embodiment, the NEP inhibitors for use in the current invention are the NEP inhibitors disclosed in U.S. Pat. No. 5,217,996, the contents of which are hereby incorporated by reference in their entirety herein.

In another embodiment, the NEP inhibitors for use in the current invention are the NEP inhibitors disclosed in US patent application publication 2013/0330365, the contents of which are hereby incorporated by reference in their entirety herein.

In another embodiment, the NEP inhibitor for use in the current invention is 3-[{1S, 3R}-1-biphenyl-4-ylmethyl-3-ethoxycarbonyl-1-butylcarbamoyl]propionic acid,

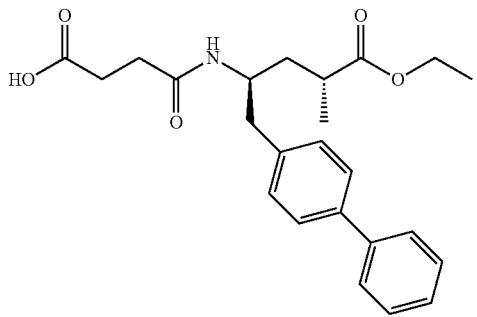 [SMILES: CCOC(=O)[C@H](C)C[C@@H](Cc1ccc(-c2ccccc2)cc1)NC(=O)CCC(=O)O]

also known as AHU-377, or a pharmaceutically acceptable salt or prodrug, thereof, and in a preferred embodiment thereof, the sodium salt.

In another embodiment, the NEP inhibitor for use in the current invention is 3-[{1S, 3R}-1-biphenyl-4ylmethyl-3-carboxy-1-butylcarbamoyl]propionic acid,

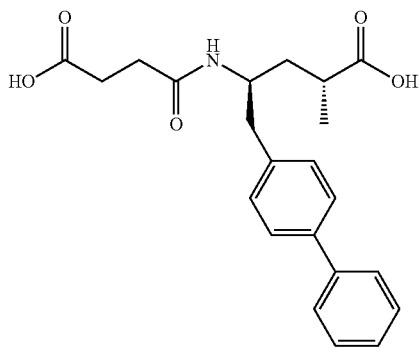 [SMILES: C[C@H](C[C@@H](Cc1ccc(-c2ccccc2)cc1)NC(=O)CCC(=O)O)C(=O)O]

also known as LBQ-657, or any pharmaceutically acceptable ester, salt or prodrug thereof.

In another embodiment, the NEP inhibitor for use in the current invention is selected from among the following, in free or pharmaceutically acceptable salt form or in prodrug form thereof: sampatrilat, fasidotril, Z13752A, MDL 100240, BMS 189921, LBQ657, AHU-377, or mixanpril, in free or pharmaceutically acceptable salt form or in prodrug form thereof.

In another embodiment, the NEP inhibitor for use in the current invention is selected from among the following, in free or pharmaceutically acceptable salt form or in prodrug form thereof:

SQ 28,603;
N-[N-[(1S)-carboxy-3-phenylpropyl]-(S)-phenylalanyl]-(S)-isoserine;
N-[N-[((1S)-carboxy-2-phenyl)ethyl]-(S)-phenylalanyl]-beta-alanine;
N-[(2S)-mercaptomethyl-3-(2-methylphenyl)-propionyl] methionine;
(cis-4-[[[1-[2-carboxy-3-(2-methoxy-ethoxy)propyl]-cyclopentyl]carbonyl]amino]cyclohexanecarboxylic acid);
thiorphan; retro-thiorphan; phosphoramidon; SQ 29072;
N-(3-carboxy-1-oxopropyl)-(4S)-p-phenylphenylmethyl)-4-amino-2R-methylbutanoic acid ethyl ester;
(S)-cis-4-[1-[2-(5-indanyloxycarbonyl)-3-(2-methoxy-ethoxy)propyl]-1-cyclopentanecarboxamido]-1-cyclohexanecarboxylic acid;
3-(1-[6-endo-hydroxymethylbicyclo[2,2,1]heptane-2-exo-carbamoyl]cyclopentyl)-2-(2-methoxyethyl)propanoic acid;
N-(1-(3-(N-t-butoxycarbonyl-(S)-prolylamino)-2(S)-t-butoxy-carbonylpropyl) cyclopentanecarbonyl)-O-benzyl-(S)-serine methyl ester;
4-[[2-(mercaptomethyl)-1-oxo-3-phenylpropyl]amino]benzoic acid;
3-[1-(cis-4-carboxycarbonyl-cis-3-butylcyclohexyl-r-1-carbamoyl)cyclopentyl]-2S-(2-methoxyethoxymethyl)propanoic acid;
N-((2S)-2-(4-biphenylmethyl)-4-carboxy-5-phenoxyvaleryl)glycine;
N-(1-(N-hydroxycarbamoylmethyl)-1-cyclopentanecarbonyl)-L-phenylalanine;
(S)-(2-biphenyl-4-yl)-1-(1H-tetrazol-5-yl)ethylamino)methylphosphonic acid;
(S)-5-(N-(2-(phosphonomethylamino)-3-(4-biphenyl)propionyl)-2-aminoethyl)tetrazole;
beta-alanine;
3-[1,1'-biphenyl]-4-yl-N-[diphenoxyphosphinyl)methyl]-L-alanyl;
N-(2-carboxy-4-thienyl)-3-mercapto-2-benzylpropanamide;
2-(2-mercaptomethyl-3-phenylpropionamido)thiazol-4-yl-carboxylic acid;
(L)-(1-((2,2-dimethyl-1,3-dioxolan-4-yl)methoxy)carbonyl)-2-phenylethyl)-L-phenylalanyl)-beta-alanine;
N-[N-[(L)-[1-[(2,2-dimethyl-1,3-dioxolan-4-yl)-methoxy]carbonyl]-2-phenylethyl]-L-phenylalanyl]-(R)-alanine;
N-[N-[(L)-1-carboxy-2-phenylethyl]-Lphenylalanyl]-(R)-alanine;
N-[2-acetylthiomethyl-3-(2-methyl-phenyl)propionyl]-methionine ethyl ester;
N-[2-mercaptomethyl-3-(2-methylphenyl)propionyl]-methionine;
N-[(2S)-mercaptomethyl-3-(2-methylphenyl)propanoyl]-(S)-isoserine;
N-(S)-[3-mercapto-2-(2-methylphenyl)propionyl]-(S)-2-methoxy-(R)-alanine;
N-[1-[[(1S)-benzyloxy-carbonyl-3-phenylpropyl]amino]cyclopentylcarbonyl]-(S) isoserine;
N-[1-[[(1S)-carbonyl-3-phenylpropyl]amino]cyclopentyl-carbonyl]-(S)-isoserine;
1,1'-[dithiobis-[(2S)-(2-methylbenzyl)-1-oxo-3,1-propanediyl]]-bis-(S)-isoserine;
1,1'-[dithiobis-[(2S)-(2-methylbenzyl)-1-oxo-3,1-propanediyl]]-bis-(S)-methionine;
N-(3-phenyl-2-(mercaptomethyl)-propionyl)-(S)-4-(methylmercapto)methionine;
N-[2-acetylthiomethyl-3-phenyl-propionyl]-3-aminobenzoic acid;
N-[2-mercaptomethyl-3-phenyl-propionyl]-3-aminobenzoic acid;
N-[1-(2-carboxy-4-phenylbutyl)-cyclopentane-carbonyl]-(S)-isoserine;

N-[1-(acetylthiomethyl)cyclopentane-carbonyl]-(S)-methionine ethyl ester;

3(S)-[2-(acetylthiomethyl)-3-phenyl-propionyl]amino-epsilon-caprolactam;

N-(2-acetylthiomethyl-3-(2-methylphenyl)propionyl)-methionine ethyl ester.

If not otherwise specified or clear from context, the following terms herein have the following meanings:

(a) "Selective PDE1 inhibitor" as used herein refers to a PDE1 inhibitor with at least 100-fold selectivity for PDE1 inhibition over inhibition of any other PDE isoform.

(b) "Selective NEP inhibitor" as used herein refers to an NEP inhibitor with at least 100-fold selectivity for NEP inhibition over ACE inhibition.

(c) "Alkyl" as used herein is a saturated or unsaturated hydrocarbon moiety, preferably saturated, preferably having one to six carbon atoms, which may be linear or branched, and may be optionally mono-, di- or tri-substituted, e.g., with halogen (e.g., chloro or fluoro), hydroxy, or carboxy.

(d) "Cycloalkyl" as used herein is a saturated or unsaturated nonaromatic hydrocarbon moiety, preferably saturated, preferably comprising three to nine carbon atoms, at least some of which form a nonaromatic mono- or bicyclic, or bridged cyclic structure, and which may be optionally substituted, e.g., with halogen (e.g., chloro or fluoro), hydroxy, or carboxy. Wherein the cycloalkyl optionally contains one or more atoms selected from N and O and/or S, said cycloalkyl may also be a heterocycloalkyl.

(e) "Heterocycloalkyl" is, unless otherwise indicated, saturated or unsaturated nonaromatic hydrocarbon moiety, preferably saturated, preferably comprising three to nine carbon atoms, at least some of which form a nonaromatic mono- or bicyclic, or bridged cyclic structure, wherein at least one carbon atom is replaced with N, O or S, which heterocycloalkyl may be optionally substituted, e.g., with halogen (e.g., chloro or fluoro), hydroxy, or carboxy.

(f) "Aryl" as used herein is a mono or bicyclic aromatic hydrocarbon, preferably phenyl, optionally substituted, e.g., with alkyl (e.g., methyl), halogen (e.g., chloro or fluoro), haloalkyl (e.g., trifluoromethyl), hydroxy, carboxy, or an additional aryl or heteroaryl (e.g., biphenyl or pyridylphenyl).

(g) "Heteroaryl" as used herein is an aromatic moiety wherein one or more of the atoms making up the aromatic ring is sulfur or nitrogen rather than carbon, e.g., pyridyl or thiadiazolyl, which may be optionally substituted, e.g., with alkyl, halogen, haloalkyl, hydroxy or carboxy.

Compounds of the Invention, e.g., PDE1 inhibitors and NEP inhibitors as described herein, may exist in free or salt form, e.g., as acid addition salts. In this specification unless otherwise indicated, language such as "Compounds of the Invention" is to be understood as embracing the compounds in any form, for example free or acid addition salt form, or where the compounds contain acidic substituents, in base addition salt form. The Compounds of the Invention are intended for use as pharmaceuticals, therefore pharmaceutically acceptable salts are preferred. Salts which are unsuitable for pharmaceutical uses may be useful, for example, for the isolation or purification of free Compounds of the Invention or their pharmaceutically acceptable salts, are therefore also included.

Compounds of the Invention may in some cases also exist in prodrug form. A prodrug form is compound which converts in the body to a Compound of the Invention. For example when the Compounds of the Invention contain hydroxy or carboxy substituents, these substituents may form physiologically hydrolysable and acceptable esters. As used herein, "physiologically hydrolysable and acceptable ester" means esters of Compounds of the Invention which are hydrolysable under physiological conditions to yield acids (in the case of Compounds of the Invention which have hydroxy substituents) or alcohols (in the case of Compounds of the Invention which have carboxy substituents) which are themselves physiologically tolerable at doses to be administered. Therefore, wherein the Compound of the Invention contains a hydroxy group, for example, Compound-OH, the acyl ester prodrug of such compound, i.e., Compound-O—C(O)—$C_{1-4}$alkyl, can hydrolyze in the body to form physiologically hydrolysable alcohol (Compound-OH) on the one hand and acid on the other (e.g., HOC(O)—$C_{1-4}$ alkyl). Alternatively, wherein the Compound of the Invention contains a carboxylic acid, for example, Compound-C(O)OH, the acid ester prodrug of such compound, Compound-C(O) O—$C_{1-4}$ alkyl can hydrolyze to form Compound-C(O)OH and HO—$C_{1-4}$alkyl. As will be appreciated the term thus embraces conventional pharmaceutical prodrug forms.

In another embodiment, the invention further provides a pharmaceutical composition comprising a PDE1 inhibitor in combination with an NEP inhibitor, each in free or pharmaceutically acceptable salt form, in admixture with a pharmaceutically acceptable carrier. The term "combination", as used herein, embraces simultaneous, sequential, or contemporaneous administration of the PDE1 inhibitor and the NEP inhibitor. In another embodiment, the invention provides a pharmaceutically composition comprising a PDE1 inhibitor in non-covalent association or complex with an NEP inhibitor. For example, wherein a PDE1 inhibitor containing a basic nitrogen is formed into an acid-base salt with an NEP inhibitor containing an acidic proton. In still another embodiment, the invention provides a compound wherein a PDE1 inhibitor is reversibly covalently bound to an NEP inhibitor. For example, wherein a PDE1 inhibitor containing a free hydroxy group is esterified to the free carboxylic acid of an NEP inhibitor, which resulting ester compound is a pro-drug of both the PDE1 inhibitor and the NEP inhibitor. In another embodiment, the invention provides a pharmaceutical composition containing such a compound. In some embodiments, the combination of the PDE1 inhibitor and the NEP inhibitor allows each to be administered in a dosage lower than would be effective for either agent administered as sole monotherapy.

Methods of Making Compounds of the Invention

The PDE1 inhibitors of the Invention of Formulas I to XI and their pharmaceutically acceptable salts may be made using the methods as described and exemplified in U.S. Pat. No. 8,273,750, US 2006/0173878, U.S. Pat. No. 8,273,751, US 2010/0273753, U.S. Pat. Nos. 8,697,710, 8,664,207, 8,633,180, 8,536,159, US 2012/0136013, US 2011/0281832, US 2013/0085123, US 2013/0324565, US 2013/0338124, US 2013/0331363, WO 2012/171016, and WO 2013/192556, and by methods similar thereto and by methods known in the chemical art. Such methods include, but not limited to, those described below. If not commercially available, starting materials for these processes may be made by procedures, which are selected from the chemical art using techniques which are similar or analogous to the synthesis of known compounds.

The PDE1 inhibitors of the invention of Formulas XV to XXI and their pharmaceutically acceptable salts, and novel intermediates for the preparation thereof, may be made using the methods as described and exemplified in EP 0201188 (or U.S. Pat. No. 4,666,908) and EP 091 1333 (or U.S. Pat. No. 6,235,742); PCT/US2006/022066; PCT/US2006/033179; WO 03/042216 (U.S. Pat. No. 6,943,171); U.S. Pat. Nos. 6,969,719; 5,939,419; EP 0 538 332 (U.S. Pat. No. 5,393, 755); Xia et al., *J Med. Chem.* (1997), 40, 4372-4377 and Ahn et al., *J Med. Chem.* (1997), 40, 2196-2210, US 2008/0242661, WO 2008/055959, and US 2009/0137549, the contents of each of which are incorporated herein by reference by their entirety.

Various PDE1 inhibitors and starting materials therefor may be prepared using methods described in US 2008-0188492 A1, US 2010-0173878 A1, US 2010-0273754 A1, US 2010-0273753 A1, WO 2010/065153, WO 2010/065151, WO 2010/065151, WO 2010/065149, WO 2010/065147, WO 2010/065152, WO 2011/153129, WO 2011/133224, WO 2011/153135, WO 2011/153136, WO 2011/153138. All references cited herein are hereby incorporated by reference in their entirety.

The NEP inhibitors of the Invention and their pharmaceutically acceptable salts may be made using the methods as described and exemplified herein and by methods similar thereto and by methods known in the chemical art. Such methods include, but not limited to, those described below. If not commercially available, starting materials for these processes may be made by procedures, which are selected from the chemical art using techniques which are similar or analogous to the synthesis of known compounds.

Various NEP inhibitors and starting materials therefor may be prepared using methods described in US 2006-0041014 A1, EP 1097719 A1, U.S. Pat. No. 8,513,244, and US 2013-0330365 A1. All references cited herein are hereby incorporated by reference in their entirety.

The Compounds of the Invention include their enantiomers, diastereomers and racemates, as well as their polymorphs, hydrates, solvates and complexes. Some individual compounds within the scope of this invention may contain double bonds. Representations of double bonds in this invention are meant to include both the E and the Z isomer of the double bond. In addition, some compounds within the scope of this invention may contain one or more asymmetric centers. This invention includes the use of any of the optically pure stereoisomers as well as any combination of stereoisomers.

It is also intended that the Compounds of the Invention encompass their stable and unstable isotopes. Stable isotopes are nonradioactive isotopes which contain one additional neutron compared to the abundant nuclides of the same species (i.e., element). It is expected that the activity of compounds comprising such isotopes would be retained, and such compound would also have utility for measuring pharmacokinetics of the non-isotopic analogs. For example, the hydrogen atom at a certain position on the Compounds of the Invention may be replaced with deuterium (a stable isotope which is non-radioactive). Examples of known stable isotopes include, but not limited to, deuterium, $^{13}C$, $^{15}N$, $^{18}O$. Alternatively, unstable isotopes, which are radioactive isotopes which contain additional neutrons compared to the abundant nuclides of the same species (i.e., element), e.g., $^{123}I$, $^{131}I$, $^{125}I$, $^{18}F$, may replace the corresponding abundant species of I, C and F. Another example of useful isotope of the compound of the invention is the $^{11}C$ isotope. These radio isotopes are useful for radio-imaging and/or pharmacokinetic studies of the compounds of the invention.

Melting points are uncorrected and (dec) indicates decomposition. Temperature are given in degrees Celsius (° C.); unless otherwise stated, operations are carried out at room or ambient temperature, that is, at a temperature in the range of 18-25° C. Chromatography means flash chromatography on silica gel; thin layer chromatography (TLC) is carried out on silica gel plates. NMR data is in the delta values of major diagnostic protons, given in parts per million (ppm) relative to tetramethylsilane (TMS) as an internal standard. Conventional abbreviations for signal shape are used. Coupling constants (J) are given in Hz. For mass spectra (MS), the lowest mass major ion is reported for molecules where isotope splitting results in multiple mass spectral peaks Solvent mixture compositions are given as volume percentages or volume ratios. In cases where the NMR spectra are complex, only diagnostic signals are reported.

Methods of Using Compounds of the Invention

The Compounds of the Invention are useful in the treatment of cardiovascular diseases characterized by increased to cGMP/PKG mediated pathways, e.g., as a result of increased expression of PDE1 or decreased expression of cGMP/PKG activity due to inhibition or reduced levels of inducers of cyclic nucleotide synthesis, such as dopamine and nitric oxide (NO). It is believed that by inhibiting PDE1A, PDE1B and/or PDE1C, for example, that this action could reverse or prevent the attenuation of cGMP/PKG signaling (e.g., enhance cGMP) and that this action could modulate cardiac hypertrophy. Therefore, administration of a preferred PDE1 inhibitor as described herein, e.g., a PDE1 inhibitor as hereinbefore described, e.g., a Compound of Formula Ia, Ib, IIa, IIb, III, IV, V, VI, VII, VIII, IX, X, XI, could provide a potential means to regulate cardiac hypertrophy (e.g., prevent and/or reverse cardiac hypertrophy), and in certain embodiments provide a treatment for various cardiovascular diseases and disorders.

Diseases and disorders that may be prevented or ameliorated by the enhancement of cGMP/PKG signaling (e.g., cardiovascular disease) include, but are not limited to: angina, stroke, renal failure, essential hypertension, pulmonary hypertension, secondary hypertension, isolated systolic hypertension, hypertension associated with diabetes, hypertension associated with atherosclerosis, renovascular hypertension, congestive heart failure, myocardial infarction, hypertension and cardiac hypertrophy.

In another embodiment, the invention further provides for the treatment or prevention of cardiovascular disease or disorder associated with: Duchenne muscular dystrophy, Becker muscular dystrophy, limb-girdle muscular dystrophy, myotonic dystrophy, and Emery-Dreifuss muscular dystrophy. In one embodiment, the Compounds of the Invention are useful in treating cardiac dysfunction associated with aforementioned types of muscular dystrophy. In another embodiment, the Compounds of the Invention may potentially reduce or reverse the cardiac hypertrophy that may be associated with these aforementioned types of muscular dystrophy.

The phrase "Compounds of the Invention" refers to the combination of a PDE1 inhibitor and an NEP inhibitor as each is described herein.

The words "treatment" and "treating" are to be understood accordingly as embracing treatment or amelioration of symptoms of disease as well as treatment of the cause of the disease.

For methods of treatment, the word "effective amount" is intended to encompass a therapeutically effective amount to treat a specific disease or disorder.

The term "patient" include human or non-human (i.e., animal) patient. In particular embodiment, the invention encompasses both human and nonhuman. In another embodiment, the invention encompasses nonhuman. In other embodiment, the term encompasses human.

The term "comprising" as used in this disclosure is intended to be open-ended and does not exclude additional, un-recited elements or method steps.

Dosages employed in practicing the present invention will of course vary depending, e.g. on the particular disease or condition to be treated, the particular Compounds of the Invention used, the mode of administration, and the therapy desired. Compounds of the Invention may be administered by any suitable route, including orally, parenterally, transdermally, or by inhalation, but are preferably administered orally. In general, satisfactory results, e.g. for the treatment of diseases as hereinbefore set forth are indicated to be obtained on oral administration at dosages of the order from about 0.01 to 2.0 mg/kg. In larger mammals, for example humans, an indicated daily dosage for oral administration of both the PDE1 inhibitor and the NEP inhibitor will accordingly be in the range of from about 0.50 to 300 mg, conveniently administered once, or in divided doses 2 to 4 times, daily or in sustained release form. Unit dosage forms for oral administration thus for example may comprise from about 0.2 to 150 or 300 mg, e.g. from about 0.2 or 2.0 to 10, 25, 50, 75 100, 150, or 200 mg of a Compound of the Invention, together with a pharmaceutically acceptable diluent or carrier therefor.

Compounds of the Invention may be administered by any satisfactory route, including orally, parenterally (intravenously, intramuscular or subcutaneous) or transdermally, but are preferably administered orally. In certain embodiments, the Compounds of the Invention, e.g., in depot formulation, is preferably administered parenterally, e.g., by injection.

The Compounds of the Invention and the Pharmaceutical Compositions of the Invention of the Invention may be used in combination with one or more additional therapeutic agents, particularly at lower dosages than when the individual agents are used as a monotherapy so as to enhance the therapeutic activities of the combined agents without causing the undesirable side effects commonly occur in conventional monotherapy. Therefore, the Compounds of the Invention may be simultaneously, separately, sequentially, or contemporaneously administered with other agents useful in treating disease. In another example, side effects may be reduced or minimized by administering a Compound of the Invention in combination with one or more additional therapeutic agents in free or salt form, wherein the dosages of (i) the second therapeutic agent(s) or (ii) both Compound of the Invention and the second therapeutic agent, are lower than if the agent/compound are administered as a monotherapy. By way of non-limiting example, such additional therapeutic agents may include ACE inhibitors, Angiotensin II receptor antagonists, calcium channel blockers, etc.

The term "simultaneously" when referring to a therapeutic use means administration of two or more active ingredients at or about the same time by the same route of administration.

The term "separately" when referring to a therapeutic use means administration of two or more active ingredients at or about the same time by different route of administration.

Pharmaceutical compositions comprising Compounds of the Invention may be prepared using conventional diluents or excipients and techniques known in the galenic art. Thus oral dosage forms may include tablets, capsules, solutions, suspensions and the like.

EXAMPLES

Example 1: Measurement of PDEI Inhibition In Vitro Using IMAP Phosphodiesterase Assay Kit Phosphodiesterase I (including PDE1A, PDEIB and PDE1C) is a calcium/calmodulin dependent phosphodiesterase enzyme that converts cyclic guanosine monophosphate (cGMP) to 5'-guanosine monophosphate (5'-GMP). PDEI can also convert a modified cGMP substrate, such as the fluorescent molecule cGMP-fluorescein, to the corresponding GMP-fluorescein. The generation of GMP-fluorescein from cGMP-fluorescein can be quantitated, using, for example, the IMAP (Molecular Devices, Sunnyvale, Calif.) immobilized-metal affinity particle reagent.

Briefly, the IMAP reagent binds with high affinity to the free 5'-phosphate that is found in GMP-fluorescein and not in cGMP-fluorescein. The resulting GMP-fluorescein-IMAP complex is large relative to cGMP-fluorescein. Small fluorophores that are bound up in a large, slowly tumbling, complex can be distinguished from unbound fluorophores, because the photons emitted as they fluoresce retain the same polarity as the photons used to excite the fluorescence.

In the phosphodiesterase assay, cGMP-fluorescein, which cannot be bound to IMAP, and therefore retains little fluorescence polarization, is converted to GMP-fluorescein, which, when bound to IMAP, yields a large increase in fluorescence polarization ($\Delta$mp). Inhibition of phosphodiesterase, therefore, is detected as a decrease in Amp.

Phosphodiesterase Enzyme Inhibition Assay

Materials: All chemicals are available from Sigma-Aldrich (St. Louis, Mo.) except for IMAP reagents (reaction buffer, binding buffer, FL-GMP and IMAP beads), which are available from Molecular Devices (Sunnyvale, Calif.).

Assay: Phosphodiesterase enzymes that may be used include: 3',5'-cyclic-nucleotide-specific bovine brain phosphodiesterase (Sigma, St. Louis, Mo.) (predominantly PDE1B, but also containing PDE1A and 1C) and recombinant full length human PDE1 A, PDE1 B and PDE1B which may be produced e.g., in HEK or SF9 cells by one skilled in the art. The PDE1 enzyme is reconstituted with 50% glycerol to 2.5 U/ml. One unit of enzyme will hydrolyze 1.0 µmol of 3',5'-cAMP to 5'-AMP per min at pH 7.5 at 30° C. One part enzyme is added to 1999 parts reaction buffer (30 µM $CaCl_2$, 10 U/ml of calmodulin (Sigma P2277), 10 mM Tris-HCl pH 7.2, 10 mM $MgCl_2$, 0.1% BSA, 0.05% $NaN_3$) to yield a final concentration of 1.25 mU/ml. 99 µl of diluted enzyme solution is added into each well in a flat bottom 96-well polystyrene plate to which 1 µl of test compound dissolved in 100% DMSO is added. The compounds are mixed and pre-incubated with the enzyme for 10 min at room temperature. [0084] The FL-GMP conversion reaction is initiated by combining 4 parts enzyme and inhibitor mix with 1 part substrate solution (0.225 µM) in a 384-well microtiter plate. The reaction is incubated in dark at room temperature for 15 min. The reaction is halted by addition of 60 µl of binding reagent (1:400 dilution of IMAP beads in binding buffer supplemented with 1:1800 dilution of antifoam) to each well of the 384-well plate. The plate is incubated at room temperature for 1 hour to allow IMAP binding to proceed to completion, and then placed in an Envision multimode microplate reader (PerkinElmer, Shelton, Conn.) to measure the fluorescence polarization ($\Delta$mp).

A decrease in GMP concentration, measured as decreased $\Delta$mp, is indicative of inhibition of PDE activity. $IC_{50}$ values are determined by measuring enzyme activity in the presence of 8 to 16 concentrations of compound ranging from 0.0037 nM to 80,000 nM and then plotting drug concentration versus Δmp, which allows $IC_{50}$ values to be estimated using nonlinear regression software (XLFit; IDBS, Cambridge, Mass.).

The PDE1 inhibitory activity of Compounds of the Invention are tested in an assay as described or similarly described herein for PDE1 inhibitory activity. For example, the PDE1 inhibitor disclosed in U.S. Pat. No. 8,273,751 on Column 23, line 29-38, has a PDE1A $IC_{50}$ value of 0.70 nM.

Example 2: Neutral Endopeptidase Enzyme Inhibition Assay

Recombinant human NEP can be obtained commercially from, for example, R&D Systems, Minneapolis, Minn. (Catalog number 1182-ZN). The fluorogenic peptide substrate Mca-D-Arg-Arg-Leu-Dap-(Dnp)-OH (Medeiros et al. (1997) *Braz. J. Med. Biol. Res.* 30:1157-62; Anaspec, San Jose, Calif.) can be used in the NEP assay. The assay can be performed in a 384-well white opaque plate at 37° C. using the fluorogenic peptide substrate at a concentration of 10 µM in Assay Buffer (50 mM HEPES, pH 7.5, 100 mM NaCl, 0.01% polyethylene glycol sorbitan monolaurate (Tween 20), 10 µM zinc sulfate. The enzyme can be used in a concentration that results in quantitative proteolysis of 1 µM of substrate after 20 minutes at 37° C. Test compounds can be assayed over the range of concentrations from 10 µM to 20 pM. Test compounds are added to the enzyme and incubated for 30 minutes at 37° C. prior to initiating the reaction by the addition of substrate. Reactions are terminated after 20 minutes incubation at 37° C. by the addition of glacial acetic acid to a final concentration of 3.6% v/v. Plates are then read on a fluorometer with excitation and emission wavelengths set to 320 nm and 405 nm, respectively. Inhibition constants can be obtained by nonlinear regression of the data using the equation $v=v_0/[1+I/K']$, where v is the reaction rate, $v_0$ is the uninhibited reaction rate, I is the inhibitor concentration and K' is the apparent inhibition constant.

Example 3: Human Cardiomyocyte Cellular Screening Assay Method for PDE1

The following screening assay is used to measure the potency of inhibitors of PDE1 in intact cells using a human cardiomyocyte (hCM) cell line developed by Promocell (Heidelberg, Germany). Promocell has devised a proprietary method for the isolation of cardiomyocytes from donated human cardiac tissue. Levels of cGMP can be measured using a competitive enzyme immunoassay (EIA) based system. Acetylcholinesterase-linked cGMP molecules compete with tissue derived cGMP for binding to cGMP-specific antibodies. The amount of antibody bound and acetylcholinesterase-linked cGMP that remains attached to an IgG-coated plate is measured by the acetylcholinesterase activity level. Specifically, acetylthiocholine is converted to thiocholine by the acetylcholinesterase enzyme, and the thiocholine then reacts with the detection reagent 2-nitrobenzoic acid to form 5-thio-2-nitrobenzoic acid, which is yellow. The 412 nm yellow wavelength can be detected and quantified spectrophotometrically.

Inhibition of PDE1 under conditions that stimulate cGMP production cause a further increase of cGMP production. Atrial natriuretic peptide (ANP) causes cGMP production via binding to the natriuretic peptide receptor A (NPRA) which activates the receptor's guanylyl cyclase domain. The Promocell hCMs respond to ANP in a dose dependent manner as measured by intracellular cGMP rise. PDE1 inhibition is found to augment this ANP-induced rise in cGMP, whereas PDE1 inhibition has little effect on basal cGMP levels (in the absence of ANP stimulation). This method has been adapted by Applicants to develop a cell-based assay for testing the potency of PDE1 inhibitors The hCM provided by Promocell (Catalog # C-12810) have been isolated from the ventricles of the adult human heart as reported by Li, et al., (Human Cell Culture Vol V, "Primary Mesenchymal Cells"; 2001, page 103-124; Luwer Academic Publishers). The epicardium and endocardium are removed and the tissue is mechanically and enzymatically digested. The cell suspension is then plated to remove the easily adherent fibroblasts. The unplated cells, primarily cardiac myocytes and endothelial cells, are plated in a fresh dish. Only the spherical hCM adhere while the rod-shaped hCM are washed away. Further purification steps using anti-CD90 antibody and anti-CD31 antibody coated beads are carried out during subculture. The hCM obtained from Promocell are sub-cultured in specialized myocyte growth media and used at passages 4 to 9 (media from Promocell, # C-22070+C-39275). Cells are defrosted according to package instructions and plated in tissue culture flasks. The cells adhere most predictably when plated at a density of at least 10,000 cells per square centimeter. The cells are passaged at 80-90% confluency. To passage, cells are rinsed once with HBSS (Gibco, Life Technologies Corp., #14170) at 100 µL/cm² of flask surface, incubated in TrypLE (Gibco, Life Technologies Corp., #12605) at 100 µL/cm² until rounded, then gently dislodged by rapping the side of the flask (e.g., as by a sharp blow or knock). An equal volume of media is added and the cells are transferred to a conical tube, centrifuged at about 200 g for 4 minutes and then resuspended in fresh media and plated. At least 96,000 cells are plated per 35 mm tissue culture dish and grown to confluency for use in the assay. Typically, the cells are incubated for about 5 days after passaging before reaching confluency.

Stock compounds are dissolved in either DMSO or 0.02N aqueous HCl at concentrations of 10 mM or 100 mM. A single compound is tested at 8 half-log dilutions in each experiment (final DMSO concentration less than 1%). The dilutions are prepared in aqueous media and warmed to 37° C. The range of concentrations chosen for the 8-point dilution are based on the $IC_{50}$ value from the biochemical assays. ANP (Tocris Bioscience, #1906) is made into a 100 mM stock solution in water and stored at −80° C. All reagents for the cGMP assay are from Cayman Chemical Co., Ann Arbor, Mich. (Cyclic GMP EIA Kit #581021).

Once the cells are grown to confluency, each dish is pretreated with either vehicle or compound for 30 minutes. Then, the cells are stimulated with 100 nM ANP or vehicle for 5 minutes. In each experiment, all 8 concentrations of compound are tested in duplicate and paired with ANP stimulation, while the controls, ANP alone and compound at the highest concentration alone, are tested once. Following treatment, the media is removed, replaced with 5% trichloroacetic acid (TCA), and the cells are placed on ice. The cells are immediately scraped in the TCA, transferred to Eppendorf tubes, sonicated and returned to ice. The precipitated protein is separated by centrifuging at 15,000 g for 20 minutes at 4° C. Cyclic nucleotides are retained in the supernatant. The TCA is removed from the supernatant using ether extraction (three washes with ethyl ether at 5× volume). The cleaned supernatants are dried in a vacuum centrifuge at room temperature and resuspended in 100 µL of ELISA assay buffer. Both the samples and the cGMP serial diluted standards are acetylated using 0.64M potassium hydroxide and 4% acetic anhydride to increase affinity of the cGMP antibody. Each of the 18 samples is tested in duplicate in the pre-coated assay plate alongside the 8-point cGMP standard dilutions. In addition, blank, maximum binding ($B_0$) and non-specific binding wells are included. To all wells containing 50 µL sample or standard, equal volumes of acetylcholinesterase-linked cGMP and cGMP antibody are added. The plate is incubated at 4° C. for 18 hours. The wells are then washed five times with wash buffer. Detection reagent containing acetylthiocholine and 2-nitrobenzoic acid is added and the plate is incubated at room temperature until the OD of the $B_0$ wells is at least 0.6 as recorded by the SoftMax 4.8 software (Molecular Devices, Sunnyvale, Calif.).

Each data point is converted to % $B/B_0$ (100*[(sample or standard OD−average non-specific binding)/(average $B_0$—average non-specific binding)]). The standards are plotted and fit to a 4-parameter logistic equation, and the concentrations of the samples are interpolated from the standard curve using Microsoft Excel and GraphPad Prizm. Values of cGMP levels are plotted against the logarithm of the concentration of compound, and the plot is fitted with a 4-parameter logistic equation (Y=Min+(Max−Min)/(1+10^((Log EC50−X)*HillSlope))). The Min value is constrained to the value of the ANP response in the absence of compound.

Figure 3:
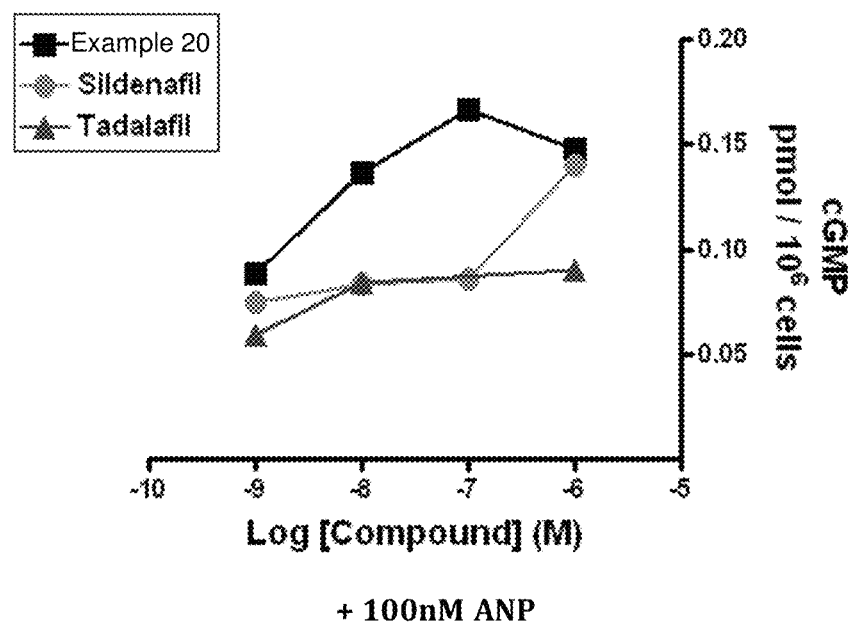
FIG. 3 shows comparative PDE1 inhibition assay results for the compound of Example 20 of U.S. Pat. No. 8,273,750, obtained using the cellular screening assay method described herein with human cardiomyocytes, compared to the PDE5 inhibitors Sildenafil and Tadalafil.

Selected PDE1 inhibitory compounds embraced by the Invention show activity in the assay described. For example, the compound disclosed as Example 20 of U.S. Pat. No. 8,273,750 shows considerable augmentation of the cGMP response to ANP, as shown in FIG. 1. In addition, as shown in FIG. 3, the cGMP response resulting from Example 20 of U.S. Pat. No. 8,273,750 is considerably greater than the response resulting from the PDE5 inhibitors Sildenafil and Tadalafil.

Example 4: Macrophage Cellular Inhibition Assay Method for PDE1

Additional experiments conducted using selected PDE1 inhibitors in an HL60 macrophage cell line (American Type Culture Collection) show that there is a synergistic effect between ANP and PDE1 inhibition. HL60 cells were grown, differentiated and harvested as described previously (see Bender, A T, and Beavo, J A, 2006, *PNAS* 103, 460-465). The cells were grown in HEPES buffered RPMI 1640 medium with penicillin, streptomycin, and 10% fetal bovine serum. Phorbol-12-myristate-13-acetate (PMA), at 100 nM for 3 days, was used to differentiate the HL60 cells into macrophage-like cells. Following differentiation, the cells were incubated with a PDE1 inhibitor or vehicle (DMSO) beginning at time 0. At 40 minutes, 5 µM ionomycin was added. At 50 minutes, 100 nM ANP was added. At 60 minutes, the cells were harvested. Total cGMP levels were measured using a competitive ELISA (Bender and Beavo, 2006).

Figure 2:
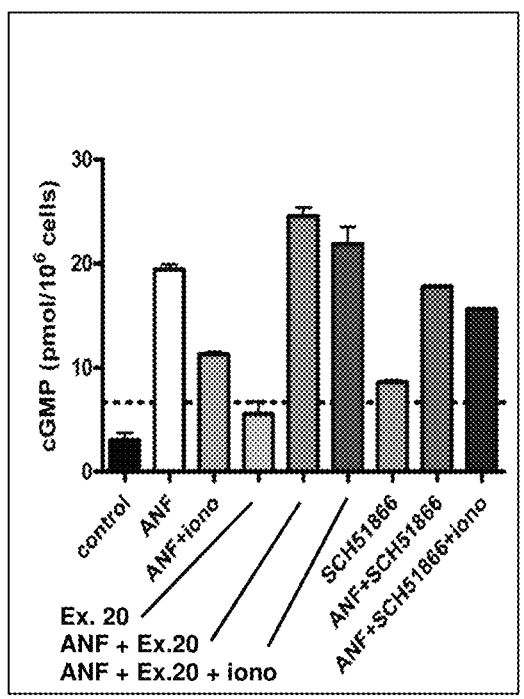
FIG. 2 shows comparative PDE1 inhibition assay results for the compound of Example 20 of U.S. Pat. No. 8,273,750, obtained using the cellular screening assay method described herein with an HL60 macrophage cell line. The results compare the PDE1 inhibitory activity of various combinations of Example 20, ANP, ionomycin (a calcium ionophore) and SCH 51866 (a dual PDE1/PDE5 inhibitor).

Using the PDE1 inhibitor disclosed as Example 20 of U.S. Pat. No. 8,273,750, it is found that the cGMP level induced in the HL60 cells by treatment with 100 nM ANP in combination with 100 nM of the PDE1 inhibitor is greater than that induced by either the ANP alone or the PDE1 inhibitor alone, as shown in FIG. 2. In addition, it can be seen that the cGMP level attained by co-treatment with ANP and the compound of Example 20 is much greater than that obtained by co-treatment with ANP and the mixed PDE1/PDE5 inhibitor SCH 51866 (used at 5 µM). In this experiment, the calcium ionophore ionomycin (used at 5 µM) was used to raise the intracellular calcium level and to counteract the cGMP rise induced by ANP. The decreasing cGMP signal caused by the activation of PDE1 by ionomycin is synergistically prevented by the combination of a PDE1 inhibitor and sub-optimal levels of ANP. Addition of ionomycin had only a weak cGMP lowering effect when combined with ANP and Example 20 treatment.

Example 5: Pharmacokinetic Analysis (Blood/Plasma Ratio)

Animals: Male, C57BL/6 mice (Jackson Labs, 25-30 g in body weight) are provided by Jackson Laboratories. Up to five mice are housed per cage and are maintained under a 12 hour light/dark cycle with access to food and water ad libitum. All procedures for the handling and use of animals follow the guidelines of the Institutional Animal Care and Use Committee (IACUC) of Columbia University, in accordance with NIH guidelines. Eight week-old mice (N=3/dose level or treatment group) are used in the experiments.

Experimental Treatment: Compounds: Selected compounds are evaluated in the present study. Formulation/Vehicle: 3% 1N HCl, 5% Labrasol and 92% of 5% TPGS in 0.05M Citrate buffer (CB, pH 4.0). The test compound(s) are prepared as solution in vehicle and are dosed in a volume of 8 ml/kg.

Compound Preparation: Powdered stocks of the test compound(s) are measured and dissolved in 3% 1N HCl, 5% Labrasol and 92% of 5% TPGS in 0.05M Citrate buffer (CB, pH 4.0). Two or three layers of 3 mm glass beads are added to the bottom of the 10 ml glass tube to promote mixing. The tube is mixed using a benchtop vortex mixer then sonicated using a VWR sonicator (model 750) for about 5 min until the drug powder is totally dissolved in into a vehicle solution.

Treatment of Animals: Mice (N=3 mice/dose/time point) receive a 10 mg/kg oral (PO) dose of the test compound(s) at time 0. Groups of mice are killed at a specified time point, either 0.25, 0.5, 1, or 2 h after drug administration. Brain tissue is collected and frozen at −80° C., until analysis. Blood is collected from the mice by puncture of the retro-orbital vein using a Pasteur pipette (VWR, Cat#53283-911), then deposited into silicon-coated blood collection tubes containing 0.105M sodium citrate solution (BD Vacutainer, #366392, Franklin Lakes, N.J.). Blood samples are centrifuged at the speed of 8000 g for 40 minutes in 4° C. (TOMY, refrigerated benchtop microcentrifuge, Fremont, Calif. 94583) and plasma decanted into Eppendorf tubes and frozen at −80° C. until analysis. Plasma and brain tissue samples are processed and analyzed by the analytical group using LC-MS/MS methods, as described below.

Sample Preparation: Samples of plasma are prepared for analysis as follows: 50 µL of the plasma samples is transferred into a 500 µl polypropylene microtube (Eppendorf Cat#022363611) as follows:

| Standards | Samples |
| --- | --- |
| 50 µL control (blank) plasma | 50 µL test sample plasma |
| 10 µL standard working solution in 1:1 Methanol:Water | 10 µL 1:1 Methanol:Water |
| 150 µL 0.1 µM Reference Compound in Methanol | 150 µL 0.1 µM Reference Compound in Methanol |

Each tube is vortex mixed, then centrifuged for 20 min at 15000 rpm. The supernatant is collected and 100 µL of each is then transferred into a 96-well polypropylene Elisa plate for mass spectrometric analysis.

Samples of brain homogenate were prepared for analysis as follows: Approximately 0.5 g of brain tissue is weighed and homogenized with 1 mL Milli-Q water. Then 60 µL of the resulting homogenate is then transferred into a clean 500 µL polypropylene microtube (Eppendorf Cat#022363611) and treated as shown below:

| Standards | Samples |
|---|---|
| 60 µL control (blank) brain homogenate | 60 µL test sample brain homogenate |
| 20 µL standard working solution in 1:1 Methanol:Water | 20 µL 1:1 Methanol:Water |
| 180 µL 0.1 µM Reference Compound in Methanol | 180 µL 0.1 µM Reference Compound in Methanol |

Each tube is vortexed, then centrifuged for 20 min at 15,000 rpm using a Tomy benchtop centrifuge at 4° C. 150 µL of each supernatant is then transferred into a 96-well plate for mass spectrometric analysis. Any remaining plasma or homogenate is stored at approximately −20° C. pending any necessary repeat analysis. For each test sample, a calibration curve is prepared covering the range of 0.5-500 ng/mL.

HPLC and Mass Spectrometric Analysis: Analysis to quantify the concentration of each compound in plasma and brain homogenate is carried out using reverse phase HPLC followed by mass spectrometric detection using the parameters listed:

| HPLC: Waters Alliance 2795 HT | |
|---|---|
| Mobile phase A: | 0.1% Formic acid in water |
| Mobile phase B: | 0.1% Formic acid in methanol |
| Column: | Phenomenex Synergi 4µ Fusion-RP 50 × 2 mm |
| Column Temperature: | 40° C. |

| Time (min) | Solvent A (%) | Solvent B (%) | Flow Rate (mL/min) |
|---|---|---|---|
| 0 | 80 | 20 | 0.6 |
| 2 | 0 | 100 | 0.6 |
| 4 | 0 | 100 | 0.6 |

| | |
|---|---|
| Waters Alliance 2795 LC rapid equilibration flow (mL/min): | 5 |
| Waters Alliance 2795 LC rapid equilibration time (min): | 0.25 |
| Re-equilibration time (min): | 1 |
| Injection volume (µl): | 10 |

Each compound is detected and quantified using Multiple Reaction Monitoring (MRM) of positive electrospray mode with a Waters QuattroMicro™ mass spectrometry system.

RESULTS: Plasma and Brain Analysis: Standard curves are established prior to the analysis of the samples and proved linear over the range of 0.5-1500 ng/mL in plasma and 0.5-500 ng/mL in brain. Plasma and brain levels of each compound are determined and expressed as means±standard deviation for each compound at each time point. Brain and plasma $C_{max}$ and $T_{max}$ values are estimated for each compound by visual inspection of the data. A ratio of brain/plasma concentration (B/P) is also calculated for each compound by dividing Brain $AUC_{(0-2h)}$/Plasma $AUC_{(0-2h)}$.

What is claimed is:

1. A method of treatment or prophylaxis of a cardiovascular disease or disorder selected from the group consisting of: angina, renal failure, hypertension, essential hypertension, pulmonary hypertension, secondary hypertension, isolated systolic hypertension, hypertension associated with diabetes, hypertension associated with atherosclerosis, renovascular hypertension, congestive heart failure, cardiac hypertrophy, myocardial infarction, or cardiovascular disease associated with a muscular dystrophy, comprising administration of a PDE1 inhibitor in combination with an NEP inhibitor to a patient in need thereof, wherein the PDE1 inhibitor is a compound of (A) Formula VII:

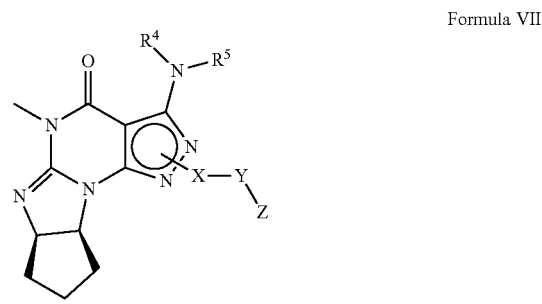

Formula VII (i) X is methylene;
(ii) Y is phenylene;
(iii) Z is heteroaryl, halo, haloC$_{1-6}$alkyl, or —C(O)—R$^1$ optionally containing at least one atom selected from a group consisting of N or O, wherein said Z is optionally substituted with halo;
(iv) R$^1$ is C$_{1-6}$alkyl, haloC$_{1-6}$alkyl, —OH or —OC$_{1-6}$alkyl;
(v) R$^4$ is H and R$^5$ is phenyl optionally substituted with one or more halo;
in free or pharmaceutically acceptable salt form;
and wherein the NEP inhibitor is selected from sampatrilat, fasidotril, Z13752A, MDL 100240, BMS 189921, LBQ657, AHU-377, and mixanpril, in free or pharmaceutically acceptable salt form.

2. The method of claim 1, wherein the PDE1 inhibitor is a selective PDE1 inhibitor.

3. The method of claim 1, wherein the NEP inhibitor is a selective NEP inhibitor.

4. The method of claim 1, wherein the PDE1 inhibitor is selected from any of the following

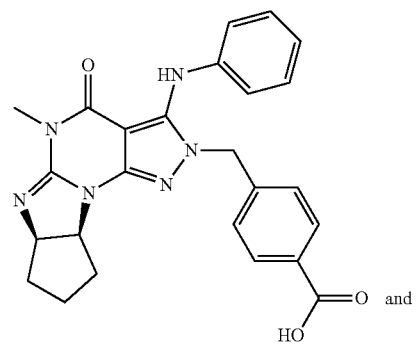

and

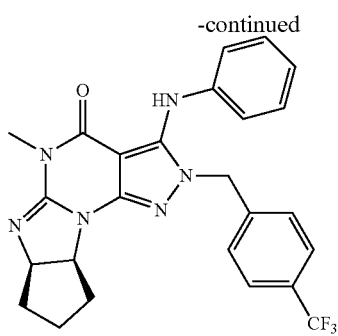

in free or pharmaceutically acceptable salt form.

5. The method of claim 1 wherein the NEP inhibitor is 3-[{1S,3R}-1-biphenyl-4-ylmethyl-3-ethoxycarbonyl-1-butylcarbamoyl]propionic acid,

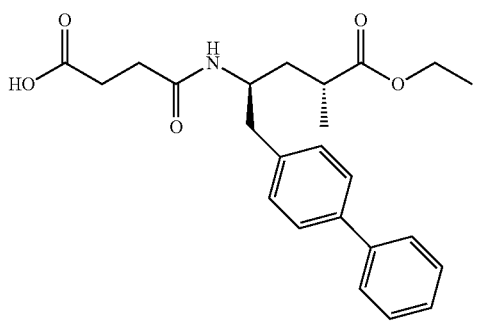 [SMILES: CCOC(=O)[C@H](C)C[C@@H](Cc1ccc(-c2ccccc2)cc1)NC(=O)CCC(=O)O]

in free or pharmaceutically acceptable salt form, preferably in the form of the sodium salt.

6. The method of claim 1 wherein the NEP inhibitor is 3-[{1S,3R}-1-biphenyl-4ylmethyl-3-carboxy-1-butylcarbamoyl]propionic acid,

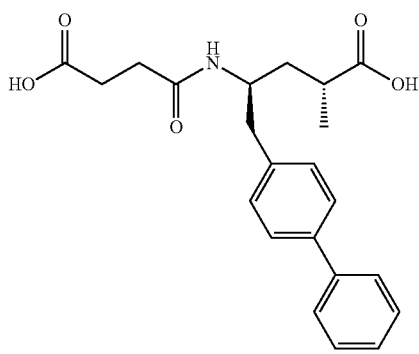 [SMILES: C[C@H](C[C@@H](Cc1ccc(-c2ccccc2)cc1)NC(=O)CCC(=O)O)C(=O)O]

in free form or in the form of any pharmaceutically acceptable ester or salt.

7. The method of claim 1 wherein the combination inhibits phosphodiesterase mediated hydrolysis of cGMP/PKG and increases plasma or serum natriuretic peptides concentration, and wherein such effects together prevent or treat cardiac hypertrophy.

8. The method of claim 1 wherein the PDE1 inhibitor is a PDE1A or PDE1C inhibitor.

9. The method of claim 1 wherein the PDE1 inhibitor is a PDE1B inhibitor.

10. The method of claim 1 wherein the disease or disorder is selected from the group consisting of: angina, hypertension, essential hypertension, pulmonary hypertension, secondary hypertension, isolated systolic hypertension, renovascular hypertension, congestive heart failure, cardiac hypertrophy, and myocardial infarction.

11. The method according to claim 10, wherein the disease or disorder is cardiac hypertrophy.

12. The method according to claim 10, wherein the disease or disorder is a cardiovascular disease associated with a muscular dystrophy.

13. The method according to claim 12, wherein muscular dystrophy is selected from the group consisting of: Duchenne muscular dystrophy, Becker muscular dystrophy, limb-girdle muscular dystrophy, myotonic dystrophy, and Emery-Dreifuss muscular dystrophy.

14. The method of claim 1, wherein R5 is unsubstituted phenyl.

15. The method of claim 14, wherein the PDE1 inhibitor is selected from

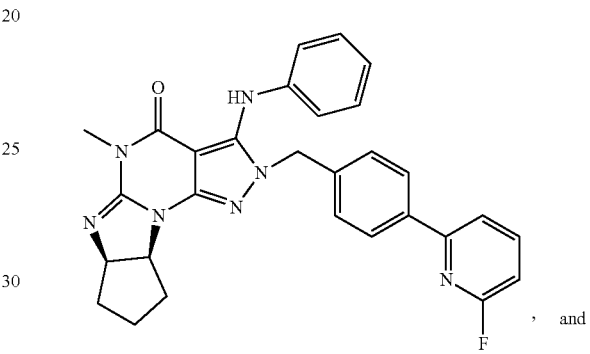

, and

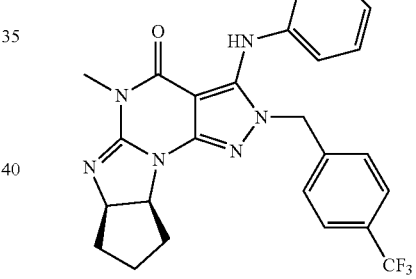

in free or pharmaceutically acceptable salt form.

16. The method of claim 15, wherein the NEP inhibitor is 3-[{1S,3R}-1-biphenyl-4-ylmethyl-3-ethoxycarbonyl-1-butylcarbamoyl]propionic acid,

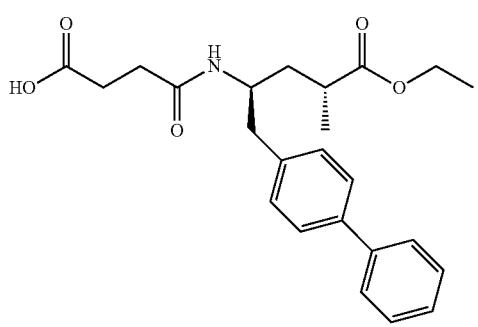 [SMILES: CCOC(=O)[C@H](C)C[C@@H](Cc1ccc(-c2ccccc2)cc1)NC(=O)CCC(=O)O]

in free or pharmaceutically acceptable salt form.

* * * * *